US010336788B2

(12) United States Patent
Lander et al.

(10) Patent No.: US 10,336,788 B2
(45) Date of Patent: Jul. 2, 2019

(54) INHIBITION OF CARDIAC FIBROSIS IN MYOCARDIAL INFARCTION

(71) Applicant: Moerae Matrix, Inc., Morristown, NJ (US)

(72) Inventors: Cynthia Lander, Mendham, NJ (US); Colleen Brophy, Nashville, TN (US); Cam Patterson, Chapel Hill, NC (US)

(73) Assignee: MOERAE MATRIX, INC., Morristown, NJ (US)

( * ) Notice: Subject to any disclaimer, the term of this patent is extended or adjusted under 35 U.S.C. 154(b) by 0 days.

(21) Appl. No.: 14/255,643

(22) Filed: Apr. 17, 2014

(65) Prior Publication Data

US 2015/0299264 A1    Oct. 22, 2015

(51) Int. Cl.

| C07K 7/06 | (2006.01) |
| C07K 7/08 | (2006.01) |
| A61K 38/08 | (2019.01) |
| A61K 38/10 | (2006.01) |
| A61K 38/17 | (2006.01) |

(52) U.S. Cl.
CPC .............. *C07K 7/06* (2013.01); *A61K 38/08* (2013.01); *A61K 38/10* (2013.01); *A61K 38/1709* (2013.01); *C07K 7/08* (2013.01); *C07K 2319/10* (2013.01)

(58) Field of Classification Search
None
See application file for complete search history.

(56) References Cited

U.S. PATENT DOCUMENTS

| 4,105,027 A | 8/1978 | Lundquist |
| 4,192,309 A | 3/1980 | Poulsen |
| 4,227,522 A | 10/1980 | Carris |
| 4,627,432 A | 12/1986 | Newell |
| 4,778,054 A | 10/1988 | Newell |
| 4,811,731 A | 3/1989 | Newell |
| 5,035,237 A | 7/1991 | Newell |
| 5,352,461 A | 10/1994 | Feldstein et al. |
| 6,071,497 A | 6/2000 | Steiner et al. |
| 6,331,318 B1 | 12/2001 | Milstein et al. |
| 6,428,771 B1 | 8/2002 | Steiner et al. |
| 6,440,463 B1 | 8/2002 | Feldstein et al. |
| 6,444,226 B1 | 9/2002 | Steiner et al. |
| 6,652,885 B2 | 11/2003 | Steiner et al. |
| 6,921,527 B2 | 7/2005 | Platz et al. |
| 7,799,344 B2 | 9/2010 | Oberg et al. |
| 7,803,404 B2 | 9/2010 | Hokenson et al. |
| 2006/0040953 A1 | 2/2006 | Leone Bay |
| 2006/0099269 A1 | 5/2006 | Cheatham et al. |
| 2012/0263680 A1* | 10/2012 | Lander et al. .............. 424/85.5 |

FOREIGN PATENT DOCUMENTS

| WO |  | 9116038 A1 | 10/1991 |
| WO | WO 2008-085191 | * | 7/2008 |

OTHER PUBLICATIONS

See et al. (Fibrosis as a Therapeutic Target Post-Myocardial Infarction; Current Pharmaceutical Design, 2005, 11, 477-487).*
Santini et al. ("Surviving acute myocardial infarction: surviv expression in viable cardiomyocytes after infarction" J Clin Pathol 2004;57:1321-1324).*
Pearson, W.R. et al., "Improved tools for biological sequence comparison." Proc Natl Acad Sci USA. 1988; vol. 85 (8), pp. 2444-2448.
Corpet, F. "Multiple sequence alignment with hierarchical clustering." Nucleic Acids Res. 1998; vol. 16(22), pp. 10881-10890.
Altschul, S.F. "Gapped BLAST and PSI-BLAST: a new generation of protein database search programs." Nucleic Acids Res. 1997; vol. 25(17), pp. 3389-3402.
Heinkoff, S. "Amino acid substitution matrices from protein blocks." Proc Natl. Acad. Sci USA; vol. 89(22), pp. 10915-10919.
Ward, B. et al., "Design of a bioactive cell-penetrating peptide: when a transduction domain does more than transduce." J Pept. Sci. 2009; vol. 15(10), pp. 668-674.
Maejima, Y. et al., Mst1 inhibits autophagy by promoting the interaction between Beclin1 and Bcl-2. Nature Medicine. 2013; vol. 19(11, pp. 1478-1488.
Qian L. et al. "In vivo reprogramming of murine cardiac fibroblasts into induced cardiomyocytes." Nature. 2012; vol. 485(7400), pp. 593-598.
Oakley, R.H. et al., "Essential role of stress hormone signaling in cardiomyocytes for the prevention of heart disease." Proc Natl Acad Sci USA. 2013; vol. 110(42), pp. 17035-17040.
Willis, M.S. et al., "Functional redundancy of SWI/SNF catalytic subunits in maintaining vascular endothelial cells in the adult heart." Circ Res. 2012; vol. 111(5), pp. 111-122.
Willis, M.S. et al., "Cardiac muscle ring finger-1 increases susceptibility to heart failure in vivo." Circ Res. 2009; vol. 105(1), pp. 80-88.

(Continued)

*Primary Examiner* — James H Alstrum-Acevedo
*Assistant Examiner* — Tara L Martinez
(74) *Attorney, Agent, or Firm* — Cooley LLP; Ivor Elrifi

(57) ABSTRACT

The described invention provides a method for treating myocardial infarction (MI) in a subject comprising administering to the subject a therapeutic amount of a pharmaceutical composition comprising a polypeptide of amino sequence YARAAARQARAKALARQLGVAA (SEQ ID NO: 1) or a functional equivalent thereof made from a fusion between a first polypeptide that is a cell permeable protein (CPP) selected from the group consisting of a polypeptide of amino acid sequence YARAAARQARA (SEQ ID NO: 2), WLRRIKAWLRRIKA (SEQ ID NO: 21), WLRRIKA (SEQ ID NO: 22), YGRKKRRQRRR (SEQ ID NO: 23), FAK-LAARLYR (SEQ ID NO: 25), and KAFAKLAARLYR (SEQ ID NO: 26), and a second polypeptide that is a therapeutic domain (TD), and a pharmaceutically acceptable carrier. The described invention also provides a kit comprising a composition comprising at least one MK2 inhibitor peptide; a means for administering the composition; and a packaging material.

14 Claims, 23 Drawing Sheets

Specification includes a Sequence Listing.

(56) References Cited

OTHER PUBLICATIONS

Claycomb, W.C. et al., "HL-1 cells: a cardiac muscle cell line that contracts and retains phenotypic characteristics of the adult cardiomyocyte." Proc Natl Acad Sci USA. 1998; vol. 95(6), pp. 2979-2984.

White, S.M. et al., "Cardiac physiology at the cellular level: use of cultured HL-1 cardiomyocytes for studies of cardiac muscle cell structure and function." Am J Physiol Heart Circ Physiol. 2004; vol. 286(3), pp. 823-829.

Laframboise, W.A. et al., "Cardiac fibroblasts influence cardiomyocyte phenotype in vitro." Am J Physiol Cell Physiol. 2007; vol. 292(5) pp. 1799-1808.

Bujak, M. et al., "The role of TGF-beta signaling in myocardial infarction and cardiac remodeling." Cardiovasc Res. 2007; vol. 74(2), pp. 184-195.

Sun, J. et al., "Ginsenoside RK3 Prevents Hypoxia-Reoxygenation Induced Apoptosis in H9c2 Cardiomyocytes via AKT and MAPK Pathway." Evid Based Complement Alternat Med. 2013; 690190, pp. 1-12.

Zhang, C. et al. "Resveratrol, a polyphenol phytoalexin, protects cardiomyocytes against anoxia/reoxygenation injury via the TLR4/NF-κB signaling pathway." Int J Mol Med. 2012; vol. 557-563.

Bukowska, A. et al., "Dronedarone prevents microcirculatory abnormalities in the left ventricle during atrial tachypacing in pigs." Br J Pharmacol. 2012; vol. 166(3), pp. 964-980.

Sangeetha, M. et al., "NF-κB inhibition compromises cardiac fibroblast viability under hypoxia." Exp Cell Res. 2011; vol. 317(7), pp. 899-909.

Leicht, M. et al., "Serum depletion induces cell loss of rat cardiac fibroblasts and increased expression of extracellular matrix proteins in surviving cells." Cardiovasc Res. 2001; vol. 52(3), pp. 429-437.

Cleutjens, J.P. et al., "Collagen remodeling after myocardial infarction in the rat heart." Am J Pathol. 1995; vol. 147 (2), pp. 325-338.

Cleutjens, J.P. et al., "The infarcted myocardium: simply dead tissue, or a lively target for therapeutic interventions." Cardiovasc Res. 1999; vol. 44(2), pp. 232-241.

Desmouliere, A. et al., "Transforming growth factor-beta 1 induces alpha-smooth muscle actin expression in granulation tissue myofibroblasts and in quiescent and growing cultured fibroblasts." J Cell Biol. 1993; vol. 122(1), pp. 103-111.

Thompson, S.A., et al., "Mechanical coupling between myofibroblasts and cardiomyocytes slows electric conduction in fibrotic cell monolayers" Circulation. 2011; vol. 123(19), pp. 2083-2093.

Rosker, C. et al., "Abolishing myofibroblast arrhythmogeneicity by pharmacological ablation of α-smooth muscle actin containing stress fibers." Circ Res. 2011; vol. 109(10), pp. 1120-1131.

Caprano, M. et al., "Bax translocates to mitochondria of heart cells during simulated ischaemia: involvement of AMP-activated and p38 mitogen-activated protein kinases." Biochem J. 2006; vol. 395(1), pp. 57-64.

Aleshin, A. et al., "Myocardial protective effect of FR167653; a novel cytokine inhibitor in ischemic-reperfused rat heart." Eur J. Cardiothorac Surg. 2004; vol. 26(5), pp. 974-980.

Gorog, D.A. et al., "Inhibition of p38 MAPK activity fails to attenuate contractile dysfunction in a mouse model of low-flow ischemia." Cardiovasc Res. 2004; vol. 61(1), pp. 123-131.

Dobaczewski, M. et al., "The extracellular matrix as a modulator of the inflammatory and reparative response following myocardial infarction." J Mol Cell Cardiol. 2010; vol. 48(3), pp. 504-511.

Brower, G.L. et al., "Cause and effect relationship between myocardial mast cell number and matrix metalloproteinase activity." Am J Physiol Heart Circ Physiol. 2002; vol. 283(2), pp. 518-525.

Chancey, A.L. et al., "Cardiac mast cell-mediated activation of gelatinase and alteration of ventricular diastolic function." Am J Physiol Heart Circ Physiol. 2002; vol. 282(6), pp. 2152-2158.

Raffetto, J.D. et al., "Matrix metalloproteinases and their inhibitors in vascular remodeling and vascular disease." Biochem Pharmacol. 2008; vol. 75(2), pp. 346-359.

Visse, R. et al., "Matrix metalloproteinases and tissue inhibitors of metalloproteinases: structure, function, and biochemistry" Circ Res. 2003; vol. 92(8), pp. 827-839.

Sun, Y. et all., "Infarct scar: a dynamic tissue." Cardiovasc Res. 2000; vol. 46(2), pp. 250-256.

Bauersachs, J. et al., "Improvement of left ventricular remodeling and function by hydroxymethylglutaryl coenzyme a reductase inhibition with cerivastatin in rats with heart failure after myocardial infarction." 2001; vol. 104(9), pp. 982-985.

Fraccarollo, D. et al., "Novel therapeutic approaches to post-infarction remodelling." Cardiovasc Res. 2012; vol. 94(2), pp. 293-303.

Kim, S.I. et al., "TGF-beta-activated kinase 1 and TAK1-binding protein 1 cooperate to mediate TGF-beta1-induced MKK3-p38 MAPK activation and stimulation of type I collagen." Am J Physiol Renal Physiol. 2007; vol. 292(5), pp. 1471-1478.

Engel, K. et al., "Leptomycin B-sensitive nuclear export of MAPKAP kinase 2 is regulated by phosphorylation." EMBO. 1998; vol. 17(12), pp. 3363-3371.

Wang, Y. "Mitogen-activated protein kinases in heart development and diseases." Circulation. 2007; vol. 116(12), pp. 1413-1423.

Marber. M.S. et al., "The p38 mitogen-activated protein kinase pathway—a potential target for intervention in infarction, hypertrophy, and heart failure." J Mol Cell Cardiol. 2011; vol. 51(4), pp. 485-490.

Sack, M.N., et al., "Tumor necrosis factor in myocardial hypertrophy and ischaemia—an anti-apoptotic perspective." Cardiovasc Res. 2000; vol. 45(3), pp. 688-695.

Tanno, M. et al. "Diverse mechanisms of myocardial p38 mitogen-activated protein kinase activation: evidence for MKK-independent activation by a TAB1-associated mechanism contributing to injury during myocardial ischemia." Circ Res. 2003; vol. 93(3), pp. 254-261.

Sanada, S. et al., "Role of phasic dynamism of p38 mitogen-activated protein kinase activation in ischemic preconditioning of the canine heart." Circ. Res. 2001; vol. 88(2), pp. 175-180.

Matsumoto-Ida M et al. "Activation of TGF-beta1-TAK1-p38 MAPK pathway in spared cardiomyocytes is involved in left ventricular remodeling after myocardial infarction in rats." Am J Physiol Heart Circ Physiol. 2005; vol. 290(2), pp. 709-715.

Hsu, P.L., "Extracellular matrix protein CCN1 regulates cardiomyocyte apoptosis in mice with stress-induced cardiac injury." Cardiovasc Res. 2013; vol. 98(1), pp. 64-72.

Muto A. et al., "Inhibition of Mitogen Activated Protein Kinase Activated Protein Kinase II with MMI-0100 reduces intimal hyperplasia ex vivo and in vivo." Vascul Pharmacol. 2012; vol. 56(1), pp. 47-55.

Vittal, R. et al., "Peptide-mediated inhibition of mitogen-activated protein kinase-activated protein kinase-2 ameliorates bleomycin-induced pulmonary fibrosis." Am J Respir Cell Mol Biol. 2013; vol. 49(1), pp. 47-57.

Ward, B.C. et al., "Peptide inhibitors of MK2 show promise for inhibition of abdominal adhesions." J Surg Res. 2011; vol. 169(1), pp. 27-36.

Loberg, R.D. et al., "Enhanced glycogen synthase kinase-3beta activity mediates hypoxia-induced apoptosis of vascular smooth muscle cells and is prevented by glucose transport and metabolism." J Biol Chem. 2002; vol. 277 (44), pp. 41667-41673.

Desai-Mehta, A. et al., "Hyperexpression of CD40 ligand by B and T cells in human lupus and its role in pathogenic autoantibody production." J Clin Invest. 1996; vol. 97(9), pp. 2063-2073.

Battaglia, M. et al., "Rapamycin promotes expansion of functional CD4+CD25+FOXP3+ regulatory T cells of both healthy subjects and type 1 diabetic patients." J Immunol. 2006; vol. 177(12), pp. 8338-8347.

Frangogiannis N.G., "The immune system and cardiac repair", Pharmacol. Res, 2008, pp. 88-11, vol. 58, National Institute of Health.

Frangogiannis. N.G., "The immune system and cardiac repair." Pharmacol Res. 2008; vol. 58(2), pp. 88-111.

Dean, R.G. et al., "Connective tissue growth factor and cardiac fibrosis after myocardial infarction." J Histochem Cytochem. 2005; vol. 53(10), pp. 1245-1256.

(56) References Cited

OTHER PUBLICATIONS

Bassols, A., et al., "Transforming growth factor beta regulates the expression and structure of extracellular matrix chondroitin/dermatan sulfate proteoglycans." J Biol Chem. 1988; vol. 263(6), pp. 3039-3045.
Ikeuchi, M. et al., "Inhibition of TGF-beta signaling exacerbates early cardiac dysfunction but prevents late remodeling after infarction." Cardiovasc Res. 2004; vol. 64(3), pp. 526-535.
Okada, H. et al., "Postinfarction gene therapy against transforming growth factor-beta signal modulates infarct tissue dynamics and attenuates left ventricular remodeling and heart failure." Circulation. 2005; vol. 111(19), pp. 2430-2437.
Dinarello, C.A., "Biologic basis for interleukin-1 in disease." Blood. 1996; vol. 87(6), pp. 2095-2147.
Bujak, M. et al., "Interleukin-1 receptor type I signaling critically regulates infarct healing and cardiac remodeling." Am J Pathol. 2008; vol. 173(1), pp. 57-67.
de Waal Malefyt. et al. "Interleukin 10(IL-10) inhibits cytokine synthesis by human monocytes: an autoregulatory role of IL-10 produced by monocytes." J Exp Med. 1991; vol. 174(5), pp. 1209-1220.
Lacraz S., et al., "IL-10 inhibits metalloproteinase and stimulates TIMP-1 production in human mononuclear phagocytes." J Clin Invest. 1995; vol. 96(5), pp. 2304-2310.
Zymek, P. "Interleukin-10 is not a critical regulator of infarct healing and left ventricular remodeling." Cardiovasc Res. 2007; vol. 74(2); pp. 313-322.
Huebener, P. et al., "CD44 is critically involved in infarct healing by regulating the inflammatory and fibrotic response" J Immunol. 2008; vol. 180(4), pp. 2625-2633.
Creemers, E. et al., "Disruption of the plasminogen gene in mice abolishes wound healing after myocardial infarction." Am J Pathol. 2000; vol. 156(6), pp. 1865-1873.
Lu, I. et al., "Matrix metalloproteinases and collagen ultrastructure in moderate myocardial ischemia and reperfusion in vivo." Am J Physiol Heart Circ Physiol. 2000; vol. 279(2), pp. 601-609.
Rohde, L.E. et al., "Matrix metalloproteinase inhibition attenuates early left ventricular enlargement after experimental myocardial infarction in mice." Circulation. 1999; vol. 99(23), pp. 3063-3070.
Ducharme, A. et al., "Targeted deletion of matrix metalloproteinase-9 attenuates left ventricular enlargement and collagen accumulation after experimental myocardial infarction." J. Clin Invest. 2000; vol. 106(1), pp. 55-62.
Jugdutt, B.I., "Ventricular remodeling after infarction and the extracellular collagen matrix: when is enough enough?" Circulation. 2003; vol. 108(11), pp. 1395-1403.
Banerjee, I. et al., "Determination of cell types and numbers during cardiac development in the neonatal and adult rat and mouse." Am J Physiol Heart Circ Physiol. 2007; vol. 293(3), pp. 1883-1891.
Willems, I.E. et al., "The alpha-smooth muscle actin-positive cells in healing human myocardial scars." Am J Pathol. 1994; vol. 4, pp. 868-875.
Gabbiani, G., "Evolution and clinical implications of the myofibroblast concept." Cardiovasc Res. 1998; vol. 38(3), pp. 545-548.
Roger, V.L. et al., "Executive summary: heart disease and stroke statistics—2012 update: a report from the American Heart Association." Circulation. 2012; vol. 125(1), pp. 1881-1897.
Pfeffer, M.A. et al., Ventricular remodeling after myocardial infarction. Experimental observations and clinical implications. Circulation. 1990; vol. 81(4), pp. 1161-1172.
Kloner, R.A. et al., "Consequences of brief ischemia: stunning, preconditioning, and their clinical implications: part 1." Circulation. 2001; vol. 104(24), pp. 2981-2989.
Heusch, G. et al. "Myocardial hibernation: a delicate balance." Am J Physiol Heart Circ Physiol. 2004; vol. 283(3), pp. 984-999.
Braunwald, E. et al., "Congestive heart failure: fifty years of progress." Circulation. 2000; vol. 102(20), pp. 14-23.
Ren, G et al. "Morphological characteristics of the microvasculature in healing myocardial infarcts." J Histochem Cytochem. 2002; vol. 50(1), pp. 71-79.

Hirai, T. et al. "Importance of collateral circulation for prevention of left ventricular aneurysm formation in acute myocardial infarction." Circulation. 1989; vol. 79(4), pp. 791-796.
Frangogiannis, N.G. et al., "The inflammatory response in myocardial infarction", Cardiovasc Res; vol. 53(1), pp. 31-47.
Frangogiannis, N.G. et al., "Resident cardiac mast cells degranulate and release preformed TNF-alpha, initiating the cytokine cascade in experimental canine myocardial ischemia/reperfusion", Circulation. 1998; vol. 98(7), pp. 699-710.
Kurrelmeyer., K.M.et al., "Endogenous tumor necrosis factor protects the adult cardiac myocyte against ischemic-induced apoptosis in a murine model of acute myocardial infarction.", Proc Natl Acad Sci. 2000; vol. 97(10), pp. 5456-5461.
Ma, X.L, et al., "Monoclonal antibody to L-selectin attenuates neutrophil accumulation and protects ischemic reperfused cat myocardium", Circulation. 1993; vol. 88(2), pp. 649-658.
Entman, M.L. et al., "Neutrophil induced oxidative injury of cardiac myocytes. A compartmented system requiring CD11b/CD18-ICAM-1 adherence", J Clin Invest. 1992; vol. 90(4), pp. 1335-1345.
Frangogiannis, M.G. et al., "Induction and suppression of interferon-inducible protein 10 in reperfused myocardial infarcts may regulate angiogenesis.", Faseb J. 2001; vol. 15(8), pp. 1428-1430.
Frangogiannis, M.G. et al., "IL-10 is induced in the reperfused myocardium and may modulate the reaction to injury", J. Immunol. 2000; vol. 165 (5), pp. 2798-2808.
Frangogiannis. N.G. et al., "Stem cell factor induction is associated with mast cell accumulation after canine myocardial ischemia and reperfusion", Circulation. 1998; vol. 98(7), pp. 687-698.
Fang, K.C. et al., "Mast cell expression of gelatinases A and B is regulated by kit ligand and TGF-beta", J Immunol. 1999; vol. 162(9), pp. 5528-5535.
Hill, J.H. et al., "The phlogistic role of C3 leukotactic fragments in myocardial infarcts of rats." J Exp Med. 1971; vol. 133(4), pp. 885-900.
Pinckard, R.N. et al., "Consumption of classical complement components by heart subcellular membranes in vitro and in patients after acute myocardial infarction." J Clin Invest. 1975; vol. 56(3), pp. 740-750.
Rossen, R.D., et al. "Cardiolipin-protein complexes and initiation of complement activation after coronary artery occlusion." Circ Res. 1994; vol. 75(3), pp. 546-555.
Vakeva, A.P., et al., "Myocardial infarction and apoptosis after myocardial ischemia and reperfusion: role of the terminal complement components and inhibition by anti-C5 therapy" Circulation. 1998; vol. 97(22), pp. 2259-2267.
Yasojima, K. "Complement gene expression by rabbit heart: upregulation by ischemia and reperfusion." Circ Res. 1998; vol. 82(11), pp. 1224-1230.
Dreyer, W.J. et al., "Kinetics of C5a release in cardiac lymph of dogs experiencing coronary artery ischemia-reperfusion injury." Circ Res. 1992; vol. 71(6), pp. 1518-1524.
Dallah, N.S., "Status of myocardial antioxidants in ischemia-reperfusion injury." Cardiovasc Res. 2000; vol. 47(3), pp. 446-456.
Granger, D.N. "Role of xanthine oxidase and granulocytes in ischemia-reperfusion injury." Am J Physiol. 1988; vol. 255(6), pp. 1269-1275.
Shingu, M., "Chemotactic activity generated in human serum from the fifth component of complement by hydrogen peroxide." Am J Pathol. 1984; vol. 117(2), pp. 201-206.
Akgur, F.M., "Role of superoxide in hemorrhagic shock-induced P-selectin expression." Am J Physiol Heart Circ Physiol. 2000; vol. 279(2), pp. 791-797.
Patel, K.D., "Oxygen radicals induce human endothelial cells to express GMP-140 and bind neutrophils." J Cell Biol. 1991; vol. 112(4), pp. 749-759.
Lakshminarayanan, V. et al., "H2O2 and tumor necrosis factor-alpha induce differential binding of the redox-responsive transcription factors AP-1 and NF-kappaB to the interleukin-8 promoter in endothelial and epithelial cells." J Biol Chem. 1998; vol. 273(49), pp. 32670-32678.

(56) References Cited

OTHER PUBLICATIONS

Lakshminarayanan, V. et al., "Differential regulation of interleukin-8 and intercellular adhesion molecule-1 by H2O2 and tumor necrosis factor-alpha in endothelial and epithelial cells." J Biol Chem. 1997; vol. 272(52), pp. 32910-32918.

Sellak, H. et al., "Reactive oxygen species rapidly increase endothelial ICAM-1 ability to bind neutrophils without detectable upregulation." 1994; vol. 83(9), pp. 2669-2677.

Jolly, S.R. et al., "Canine myocardial reperfusion injury. Its reduction by the combined administration of superoxide dismutase and catalase." Circ Res. 1984; vol. 54(3), pp. 277-285.

Uraizee, A., "Failure of superoxide dismutase to limit size of myocardial infarction after 40 minutes of ischemia and 4 days of reperfusion in dogs." Circulation. 1987; vol. 75(6), pp. 1237-1248.

Gallagher, K.P., "Failure of superoxide dismutase and catalase to alter size of infarction in conscious dogs after 3 hours of occlusion followed by reperfusion." Circulation. 1986; vol. 73(5), pp. 1065-1076.

Richard, V.J., "Therapy to reduce free radicals during early reperfusion does not limit the size of myocardial infarcts caused by 90 minutes of ischemia in dogs." Circulation. 1988; vol. 78(2), pp. 473-480.

Wang, P., et al., "Overexpression of human copper, zinc-superoxide dismutase (SOD1) prevents postischemic injury." Proc Natl Acad Sci USA. 1998; vol. 95(8), pp. 4556-4560.

Flaherty, J.T. et al., "Recombinant human superoxide dismutase (h-SOD) fails to improve recovery of ventricular function in patients undergoing coronary angioplasty for acute myocardial infarction." Circulation. 1994; vol. 89(5), pp. 1982-1991.

Irwin, M.W. et al., "Tissue expression and immunolocalization of tumor necrosis factor-alpha in postinfarction dysfunctional myocardium." Circulation. 1999; vol. 99(11), pp. 1492-1498.

Siwik, D.A. et al., "Interleukin-1beta and tumor necrosis factor-alpha decrease collagen synthesis and increase matrix metalloproteinase activity in cardiac fibroblasts in vitro." Circ. Res. 2000;vol. 86(12), pp. 1259-1265.

Frangiogannis, N.G. "Chemokines in ischemia and reperfusion." Thrombosis and haemostasis. 2007; vol. 97, pp. 738-747.

Belosjorow S. et al., "Endotoxin and ischemic preconditioning: TNF-alpha concentration and myocardial infarct development in rabbits." Am J Physiol. 1999; vol. 277(6), pp. 2470-2475.

Birdsall, H.H. et al., "Complement C5a, TGF-beta 1, and MCP-1, in sequence, induce migration of monocytes into Ischemic canine myocardium within the first one to five hours after reperfusion." Circulation. 1997; vol. 95(3), pp. 684-692.

Gwechenberger, M. et al., "Cardiac myocytes produce interleukin-6 in culture and in viable border zone of reperfused infarctions." Circulation. 1999; vol. 99(4), pp. 546-551.

Nah, D.Y. et al. "The inflammatory response and cardiac repair after myocardial infarction." Korean Circ J. 2009; vol. 39(10), pp. 393-398.

Romson, J.L. et al., "Reduction of the extent of ischemic myocardial injury by neutrophil depletion in the dog." Circulation. 1983; vol. 67(5), pp. 1016-1023.

Jordan, J.E. et al., "The role of neutrophils in myocardial ischemia-reperfusion injury". Cardiovasc Res. 1999; vol. 43(4), pp. 860-878.

Jaeshcke, H. et al., "Mechanisms of neutrophil-induced parenchymal cell injury." J Leukoc Biol. 1997; vol. 61(6), pp. 647-653.

Jones, S.P., "Myocardial ischemia-reperfusion injury is exacerbated in absence of endothelial cell nitric oxide synthase." Am J Physiol. 1999; vol. 275(5), pp. 1567-1573.

Palazzo, A.J., et al., "Coronary endothelial P-selectin in pathogenesis of myocardial ischemia-reperfusion injury." Am. J. Physiol. 1998; vol. 275(5), pp. 1865-1872.

Dewald, O. et al. "CCL2/Monocyte Chemoattractant Protein-1 regulates inflammatory responses critical to healing myocardial infarcts." Circ Res. 96(8), pp. 881-889.

* cited by examiner

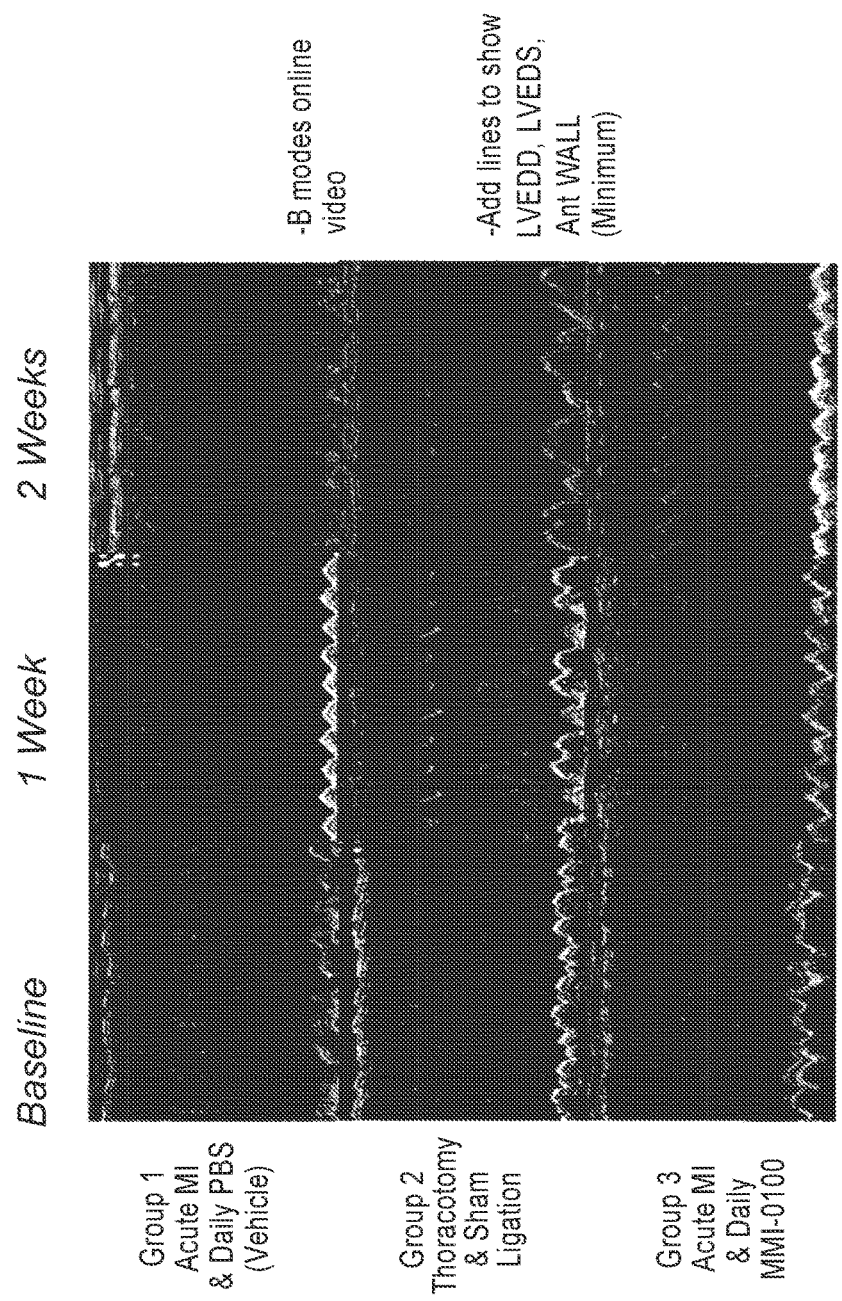

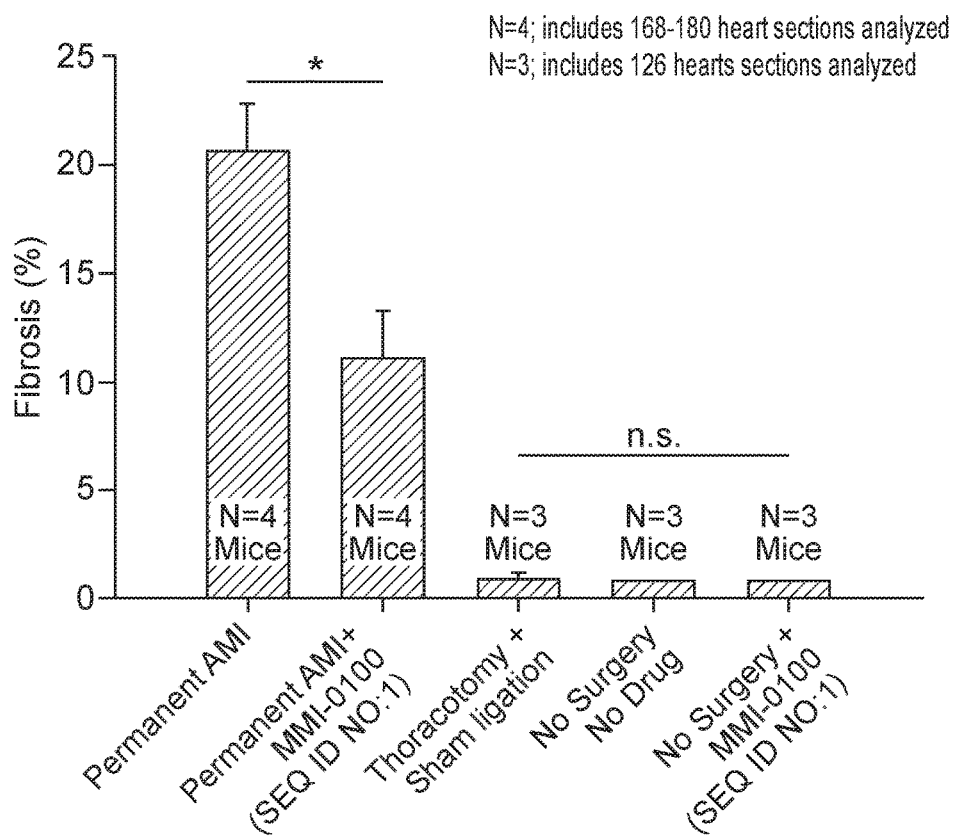

FIG. 2C
Permanent AMI + PBS (~21% Fibrosis)
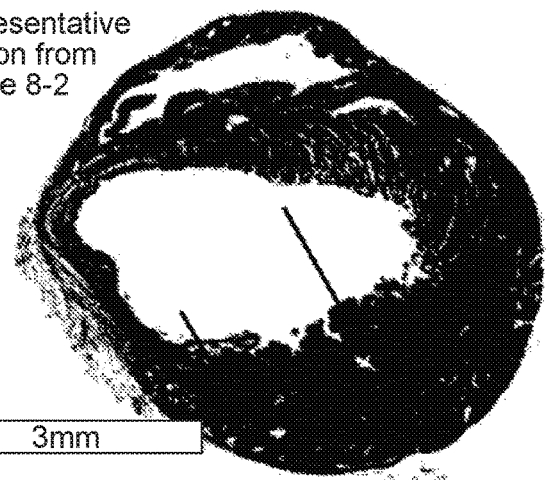
Representative Section from Mouse 8-2
3mm
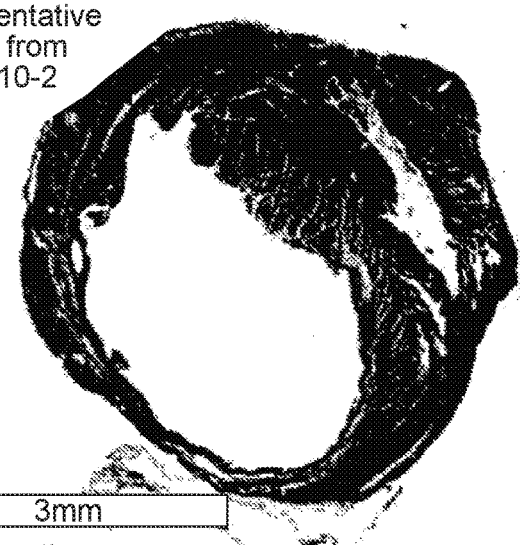
Representative Section from Mouse 10-2
3mm
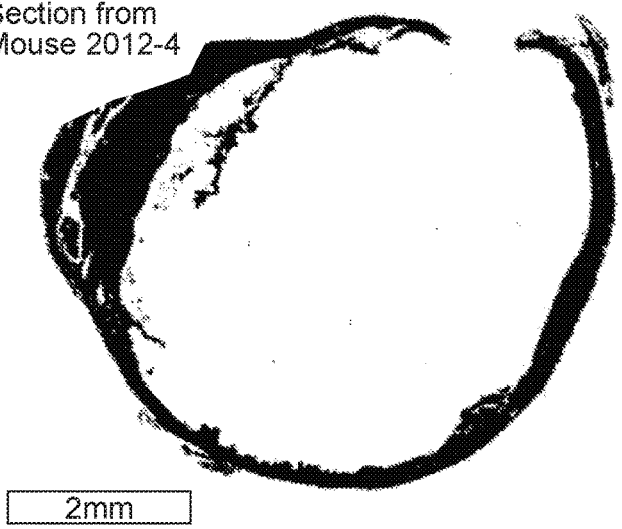
Representative Section from Mouse 2012-4
2mm FIG. 2D
Permanent AMI + MMI-0100 (~11% Fibrosis) (SEQ ID NO:1)
Representative Section from Mouse 2012-22
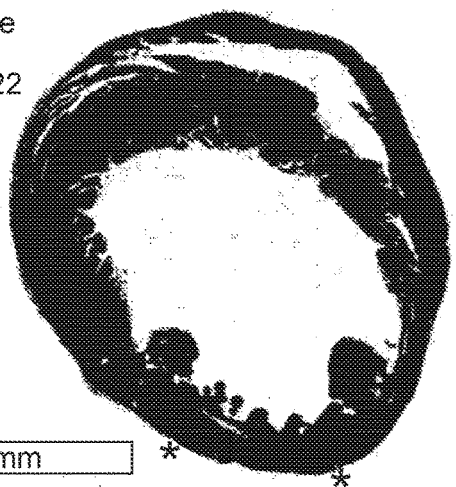
3mm
Representative Section from Mouse 7-2
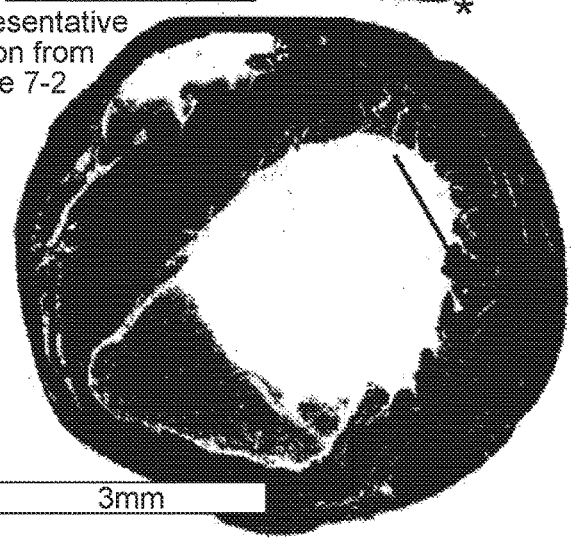
3mm
Representative Section from Mouse 5-2
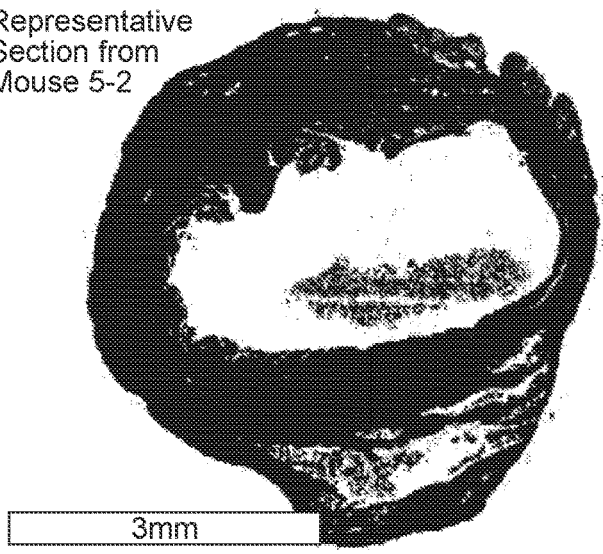
3mm FIG. 2E  Controls
Representative Section from Mouse 15
Thoracotomy + Sham ligation
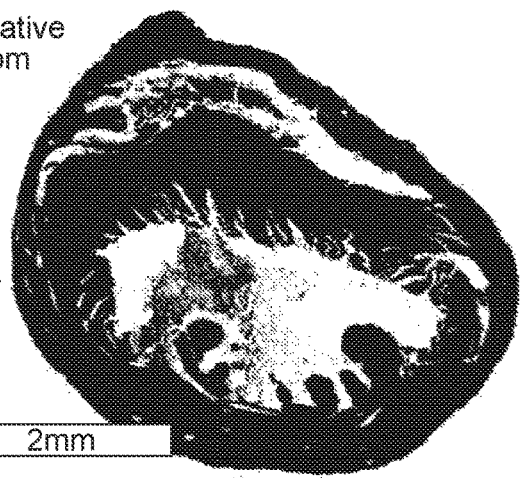
2mm
Representative Section from Mouse 3-4
No Surgery No Drug
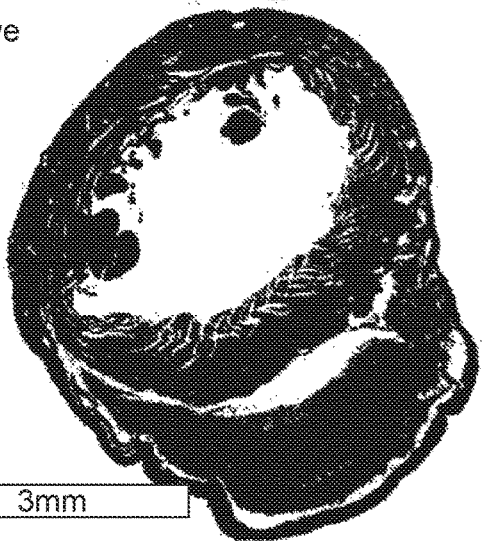
3mm
Representative Section from Mouse 3-3
No Surgery + MMI-0100 (SEQ ID NO:1)
2mm

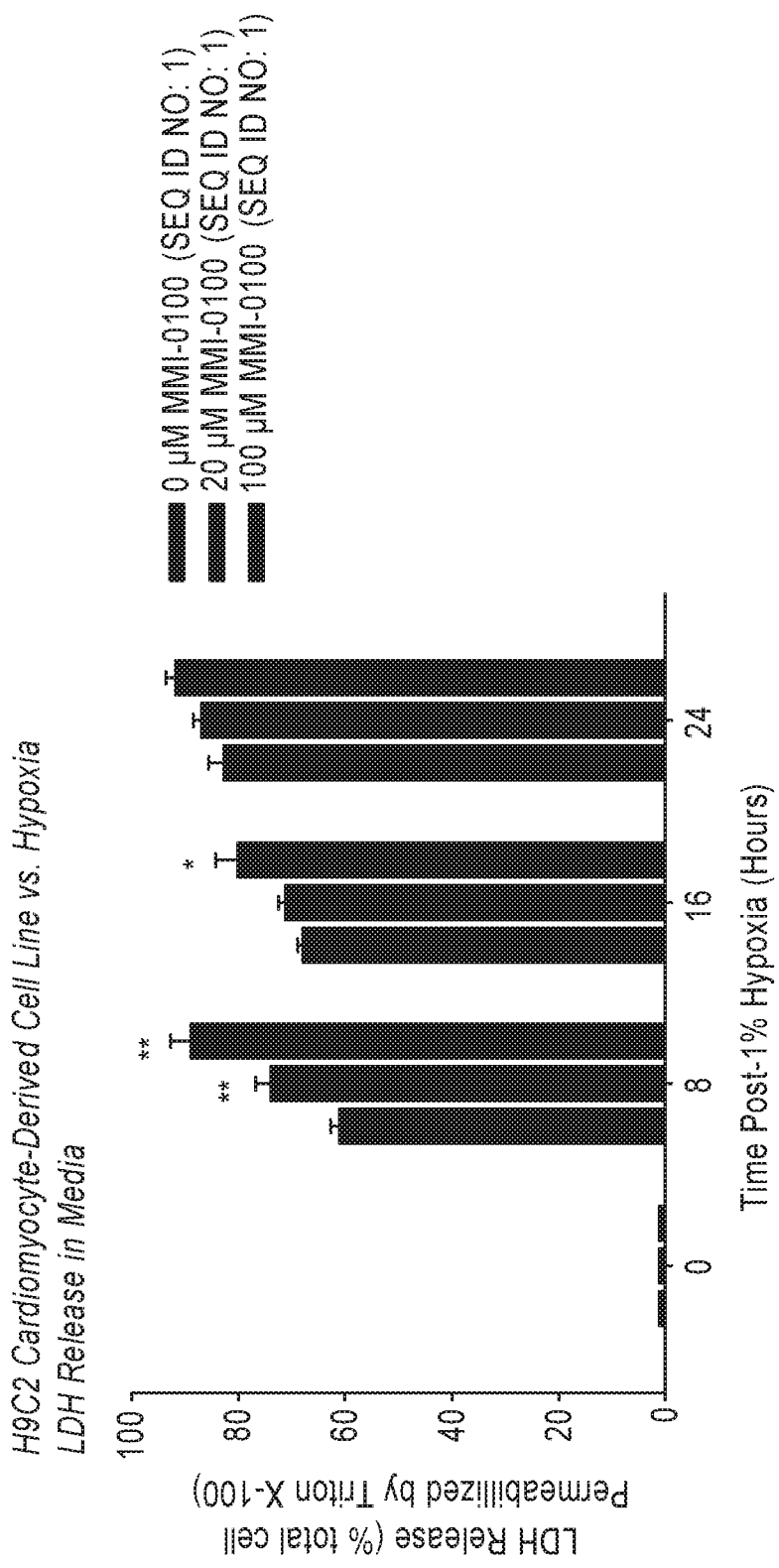

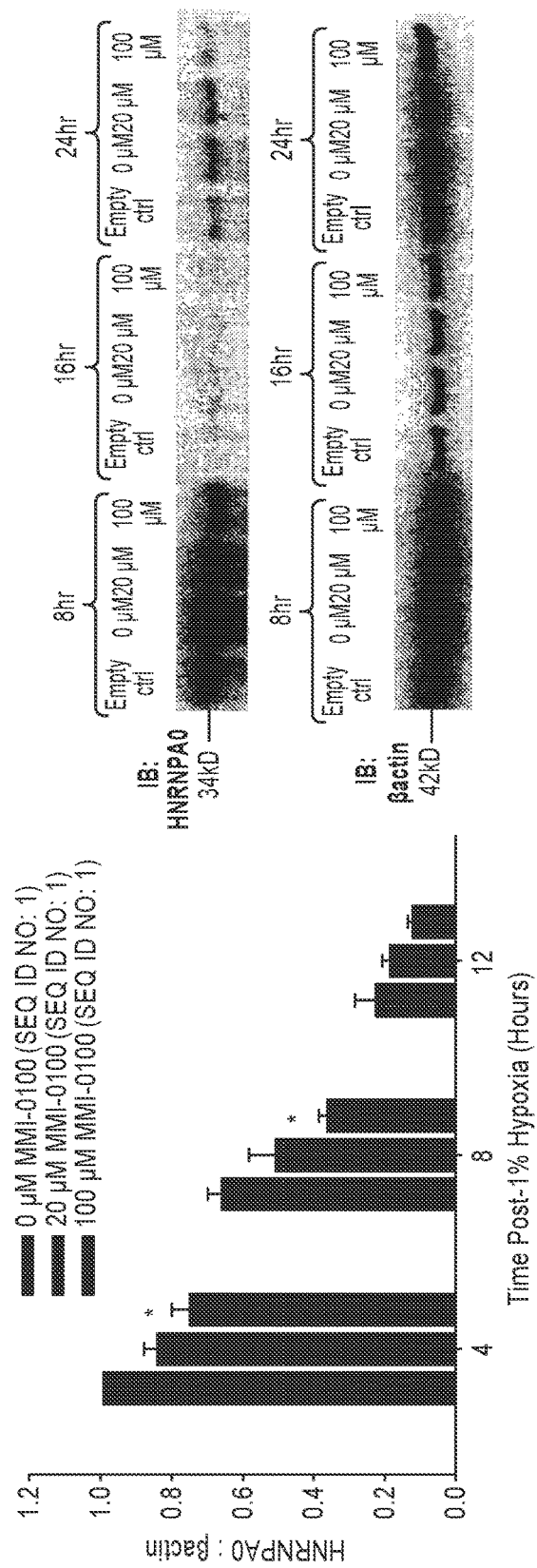

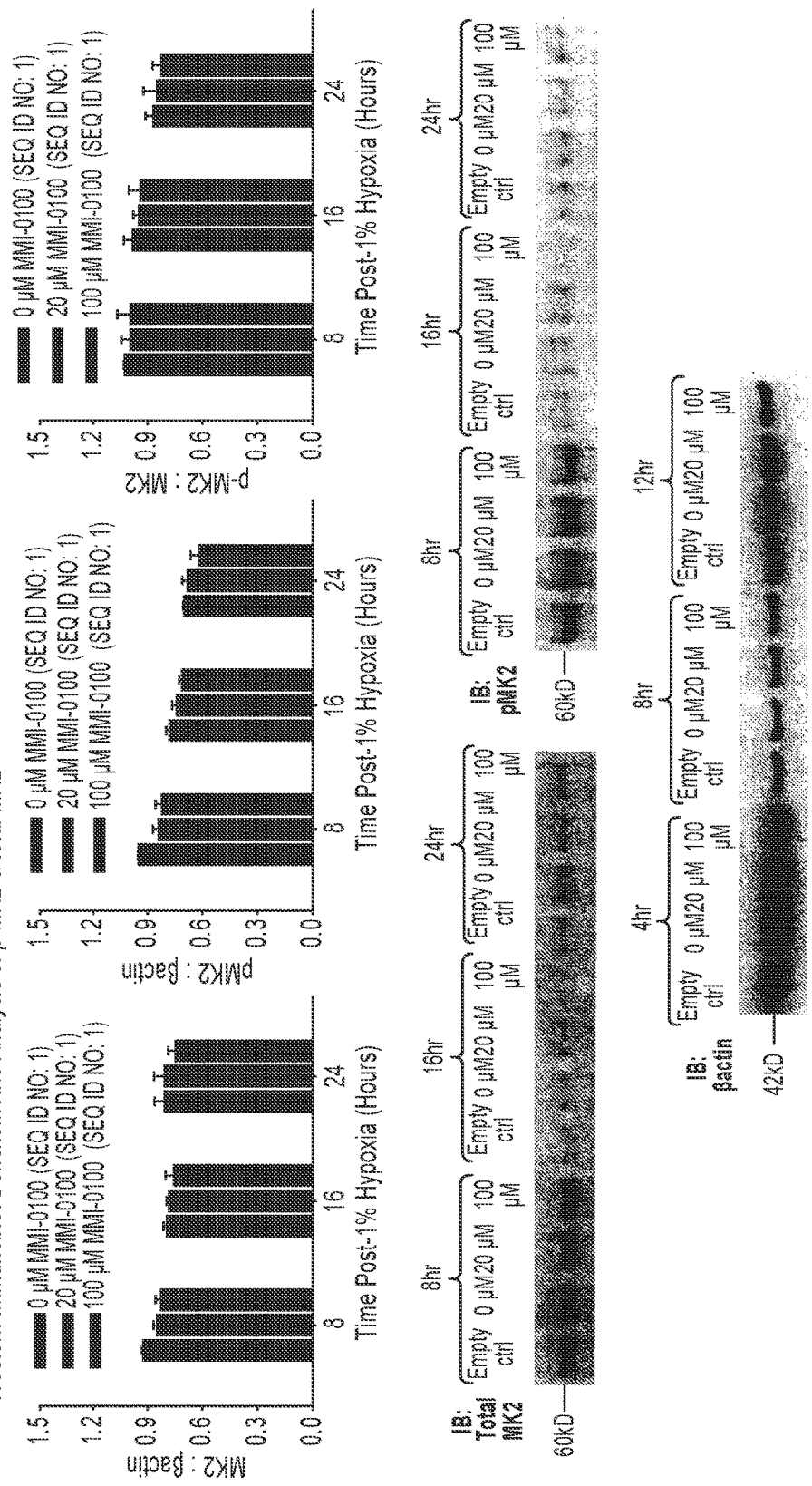

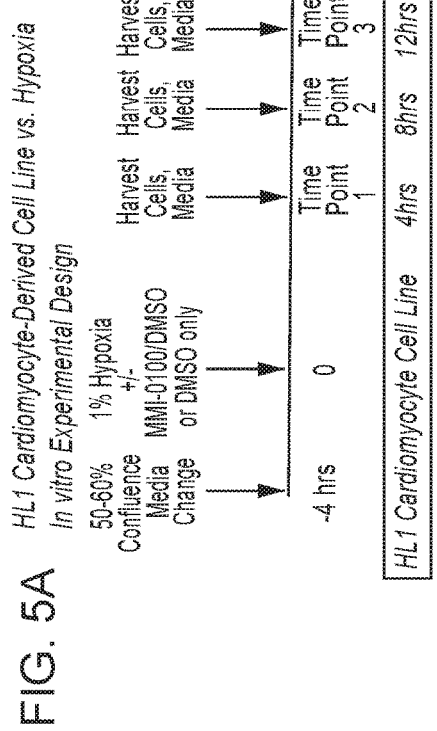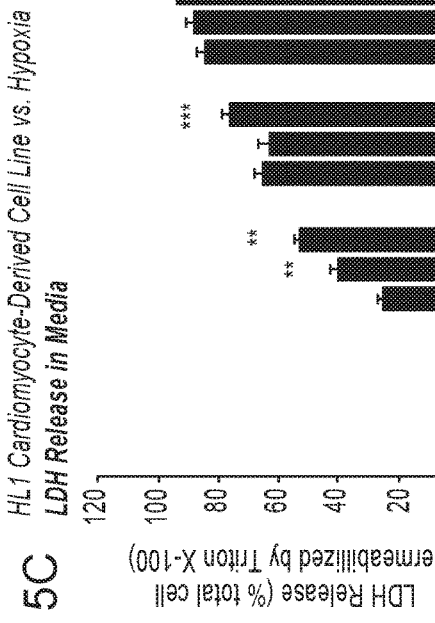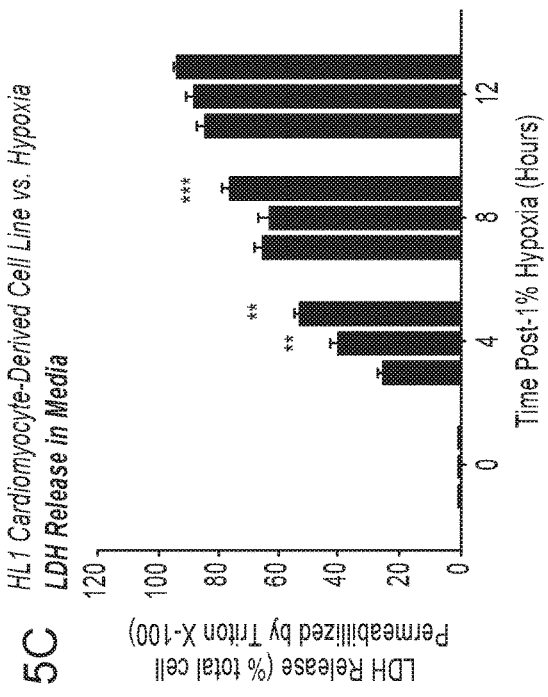

HL1 Cardiomyocyte-Derived Cell Line
Western Immunoblot Densitometric Analysis of HNRNPA0

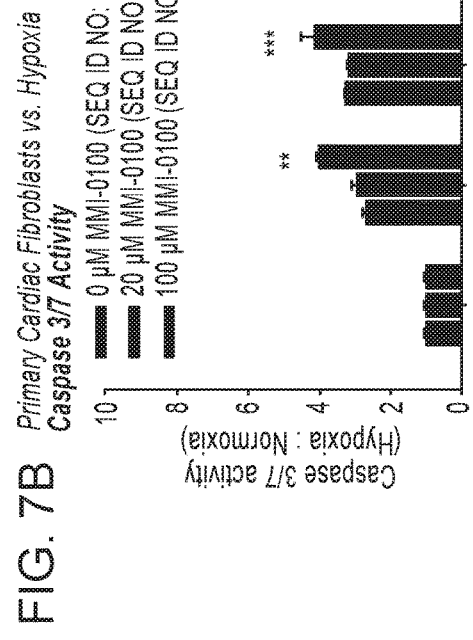
FIG. 7A  Primary Cardiac Fibroblasts vs. Hypoxia
In vitro Experimental Design
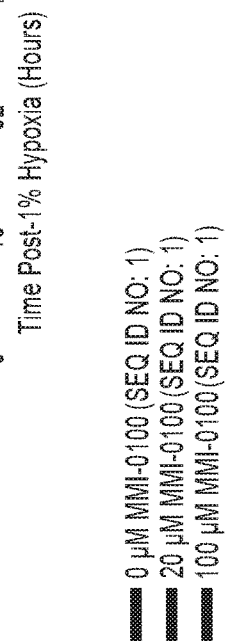
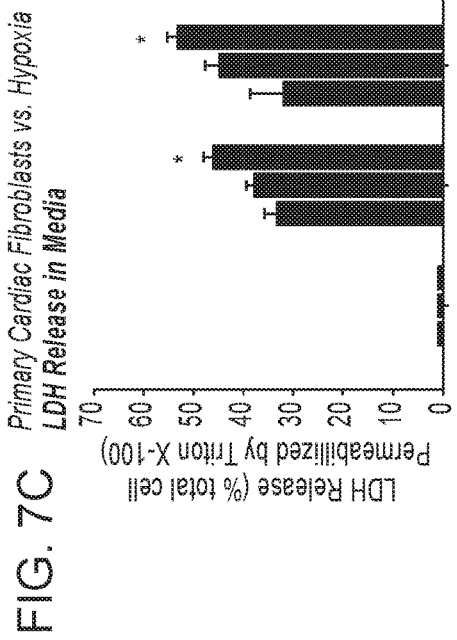
FIG. 7B  Primary Cardiac Fibroblasts vs. Hypoxia
Caspase 3/7 Activity
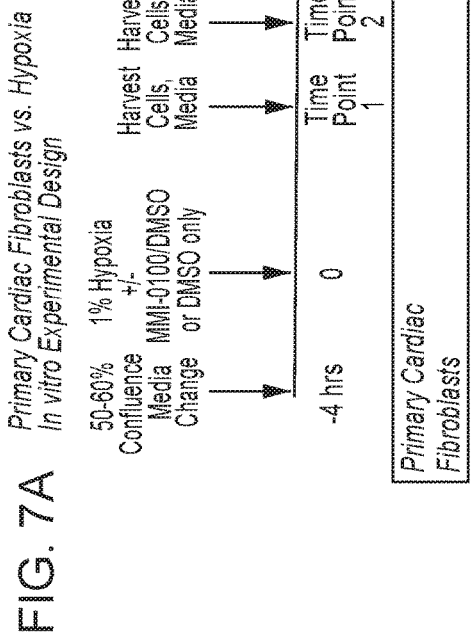
FIG. 7C  Primary Cardiac Fibroblasts vs. Hypoxia
LDH Release in Media FIG. 10A   FIG. 10B   FIG. 10C
Acute MI by permanent LAD ligation + Daily PBS treatment
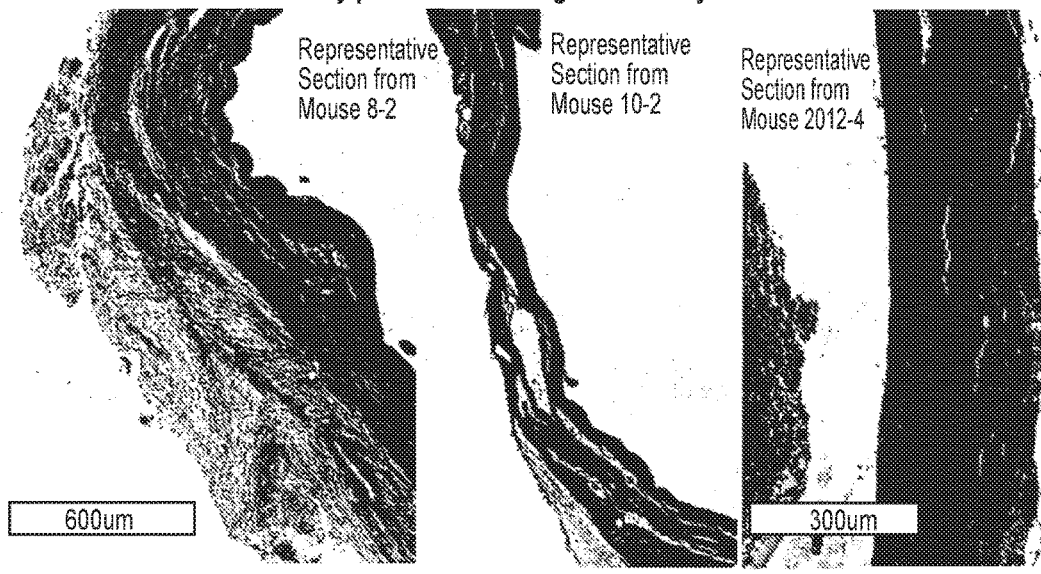
FIG. 10D
Acute MI by permanent LAD ligation + Daily MMI-0100 (SEQ ID NO:1) (in PBS) treatment
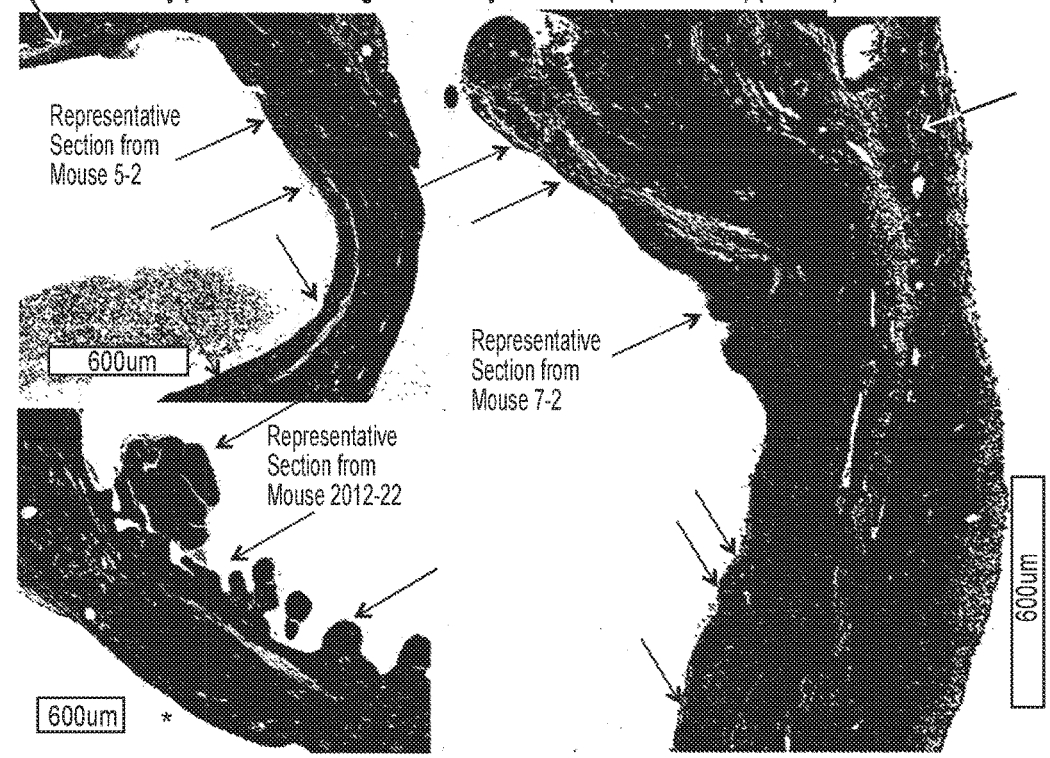
FIG. 10E   FIG. 10F

INHIBITION OF CARDIAC FIBROSIS IN MYOCARDIAL INFARCTION

FIELD OF THE INVENTION

The described invention relates to the inhibition of cardiac fibrosis in myocardial infarction by direct actions on cardiomyocytes and fibroblasts by inhibiting Mitogen Activated Protein Kinase Activated Protein Kinase II (MK2) activity.

BACKGROUND OF THE INVENTION

Ischemic Heart Disease/Myocardial Infarction

Ischemic heart disease is the most common cause of death in the world. In the United States alone an estimated 785,000 people will have a myocardial infarction (MI) each year; approximately 1 per minute [Roger V L, Go A S, Lloyd-Jones D M, Benjamin E J, Berry J D, Borden W B, et al. Executive summary: heart disease and stroke statistics—2012 update: a report from the American Heart Association. Circulation. 2012; 125:188-97]. The adverse remodeling that occurs after myocardial infarction contributes to the impaired cardiac function and heart failure associated with increased morbidity and mortality. Advances made in interventional, largely early reperfusion therapies, have improved patient survival while increasing the morbidity and mortality of the resulting heart failure [Pfeffer M A, Braunwald E. Ventricular remodeling after myocardial infarction. Experimental observations and clinical implications. Circulation. 1990; 81:1161-72; Opie L H, Commerford P J, Gersh B J, Pfeffer M A. Controversies in ventricular remodeling. Lancet. 2006; 367:356-67; Dorn G W, 2nd. Novel pharmacotherapies to abrogate post-infarction ventricular remodeling. Nat Rev Cardiol. 2009; 6:283-91]. The size of the infarcted area, the infarcted wound healing, and chronic left ventricular (LV) remodeling determine the extent of heart failure that results [Pfeffer M A, Braunwald E. Ventricular remodeling after myocardial infarction. Experimental observations and clinical implications. Circulation. 1990; 81:1161-72; Opie L H, Commerford P J, Gersh B J, Pfeffer M A. Controversies in ventricular remodelling. Lancet. 2006; 367:356-67; Dorn G W, 2nd. Novel pharmacotherapies to abrogate post-infarction ventricular remodeling. Nat Rev Cardiol. 2009; 6:283-91].

Ischemia

The myocardium depends almost entirely on aerobic metabolism, since oxygen stores in the heart are meager. Myocardial oxygen supply rises and falls in response to the oxygen (energy) demands of the myocardium. The term "autoregulation" refers to the ability to maintain myocardial perfusion at constant levels in the face of changing driving forces. Autoregulation maintains coronary perfusion at relatively constant levels over a wide range of mean aortic pressure. When aortic pressure exceeds its upper or lower limits, coronary blood flow precipitously declines or increases proportionately.

The heart needs to be supplied with a sufficient quantity of oxygen to prevent under-perfusion. When reduced perfusion pressure distal to stenoses is not compensated by auto-regulatory dilation of the resistance vessels, ischemia, meaning a lack of blood supply and oxygen, occurs. Because the zone least supplied generally is the farthest out, ischemia generally appears in areas farthest away from the blood supply.

After total or near-total occlusion of a coronary artery, myocardial perfusion occurs by way of collaterals, meaning vascular channels that interconnect epicardial arteries. Collateral channels may form acutely or may preexist in an under-developed state before the appearance of coronary artery disease. Preexisting collaterals are thin-walled structures ranging in diameter from 20 μm to 200 μm, with a variable density among different species. Preexisting collaterals normally are closed and nonfunctional, because no pressure gradient exists to drive flow between the arteries they connect. After coronary occlusion, the distal pressure drops precipitously and preexisting collaterals open virtually instantly.

The term "myocardial ischemia" refers to a decrease in blood supply and oxygen to the cells of the myocardium. The development of myocardial ischemia has been attributed to two mechanisms: (1) increased myocardial oxygen demand, and (2) decreased myocardial perfusion and oxygen delivery [Willerson, J. T. et al., J. Am. Coll. Cardiol. 8(1): 245-50 (1986)]. Myocardial ischemia generally appears first and is more extensive in the subendocardial region, since these deeper myocardial layers are farthest from the blood supply, with greater need for oxygen.

Transient Ischemia

The term "transient ischemia" as used herein refers to a reversible (meaning that the myocytes survive the insult) narrowing of a coronary artery at rest or with exercise where there is no thrombus or plaque rupture but where blood supply cannot be met. Every time the heart's oxygen demand increases, an imbalance between oxygen demand and supply is created. Transient ischemia produces a cascade of events beginning with metabolic and biochemical alterations leading to impaired ventricular relaxation and diastolic dysfunction, impaired systolic function, and electrocardiographic abnormalities with ST segment alterations, followed by increased end-diastolic pressure with left ventricular dyssynchrony, hypokineses, akinesis, and dyskinesis, and lastly painful symptoms of angina. Even though ischemic myocytes experience physiological and metabolic changes within seconds of the cessation of coronary flow, resulting in T wave and sometimes ST segment abnormalities (but without serum enzyme elevation), no cell death results from the ischemia [Kloner, R. A. and Jennings, R B, Circulation 104: 2981-89 (2001)]. Once blood flow is re-established, a complete recovery of myocyte contractile function takes place.

Although angina pectoris (chest pain) may be a symptom of transient ischemia, by and large transient ischemia is silent (meaning ST-segment depression of at least 1 mm is present without associated symptoms, e.g., chest pain) in 79% of subjects. In most patients with stable angina, for example, physical effort or emotion, with a resultant increase in heart rate, blood pressure, or contractile state, or any combination thereof, increases myocardial oxygen demand without an adequate delivery in oxygen delivery through tightly narrowed (stenosed) coronary arteries. More than 40% of patients with stable angina treated with one or more antianginal drugs have frequent episodes of silent ischemia, which has been shown to predict a higher risk of coronary events and cardiac death [Deedwania, P C, Carbajal, E V, Arch. Intern. Med. 150: 2373-2382 (1991)].

Chronic Myocardial Ischemia

The term "chronic myocardial ischemia (CMI)" as used herein refers to a prolonged subacute or chronic state of myocardial ischemia due to narrowing of a coronary blood vessel in which the myocardium "hibernates", meaning that the myocardium downregulates or reduces its contractility, and hence its myocardial oxygen demand, to match reduced perfusion, thereby preserving cellular viability and preventing myocardial necrosis. This hibernating myocardium is capable of returning to normal or near-normal function on restoration of an adequate blood supply. Once coronary blood flow has been restored to normal or near normal and ischemia is resolved, however, the hibernating myocardium still does not contract. This flow-function mismatch resulting in a slow return of cardiac function after resolution of ischemia has been called stunning. The length of time for function to return is quite variable, ranging from days to months, and is dependent on a number of parameters, including the duration of the original ischemic insult, the severity of ischemia during the original insult, and the adequacy of the return of the arterial flow. A number of studies have provided evidence for inflammation in hibernating myocardium [Heusch, G. et al., Am. J. Physiol. Heart Circ. Physiol. 288: 984-99 (2005)]. A study conducted in a porcine model of myocardial hibernation in which the mean rest (left anterior descending coronary artery (LAD) coronary blood flow was reduced to about 60% of baseline for a period of 24 hours to four weeks, detected apoptotic myocytes in all experimental pigs in the hibernating regions supplied by the stenotic LAD, suggesting that functional downregulation may not be adequate to prevent gradual, ongoing myocyte death through apoptosis in hibernating myocardium [Chen, C, et al., J. Am. Coll. Cardiol. 30: 1407-12 (1997)].

Acute Myocardial Infarction (AMI)

Another type of insult occurs during AMI. AMI is an abrupt change in the lumen of a coronary blood vessel that results in ischemic infarction, meaning that it continues until heart muscle dies. On gross inspection, myocardial infarction can be divided into two major types: transmural infarcts, in which the myocardial necrosis involves the full or nearly full thickness of the ventricular wall, and subendocardial (non-transmural) infarcts, in which the myocardial necrosis involves the subendocardium, the intramural myocardium, or both, without extending all the way through the ventricular wall to the epicardium. There often is total occlusion of the vessel with ST segment elevation because of thrombus formation within the lumen as a result of plaque rupture. The prolonged ischemic insult results in apoptotic and necrotic cardiomyocyte cell death [See Kajstura, J., et al., Lab Invest. 74: 86-107 (1996)]. Necrosis compromises the integrity of the sarcolemmal membrane and intracellular macromolecules such that serum cardiac markers, such as cardiac-specific troponins and enzymes, such as serum creatine kinase (CK), are released. In addition, the patient may have electrocardiogram (ECG) changes because of full thickness damage to the muscle. An ST-Elevation Myocardial Infarction (STEMI) is a larger injury than a non-ST-elevation myocardial infarction. ST-segment elevation and Q waves on the ECG, two features highly indicative of myocardial infarction, are seen in only about half of myocardial infarction cases on presentation.

AMI remains common with a reported annual incidence of 1.1 million cases in the United States alone [Antman, E. M., Braunwald, E., Acute Myocardial Infarction, in Principles of Internal Medicine, 15th Ed., Braunwald, E. et al., Eds., New York: McGraw-Hill (2001)]. Preclinical and clinical data demonstrate that following a myocardial infarction, the acute loss of myocardial muscle cells and the accompanying peri-infarct border zone hypo-perfusion result in a cascade of events causing an immediate diminution of cardiac function, with the potential for long term persistence. The extent of myocardial cell loss is dependent on the duration of coronary artery occlusion, existing collateral coronary circulation and the condition of the cardiac microvasculature [Paul et al., Am. Heart J. 131: 710-15 (1996); Pfeffer, M. A., Braunwald, E., Circulation 81: 1161-72 (1990); Sheilban, I. e. al., J. Am. Coll. Cardiol. 38: 464-71 (2001); Braunwald E., Bristow, M. R., Circulation 102: IV-14-23 (2000); Rich et al., Am. J. Med. 92:7-13 (1992); Ren et al., J. Histochem. Cytochem. 49: 71-79 (2002); Hirai, T. et al., Circulation 79: 791-96 (1989); Ejiri, M. et al., J. Cardiology 20: 31-37 (1990)]. Because myocardial cells have virtually no ability to regenerate, myocardial infarction leads to permanent cardiac dysfunction due to contractile-muscle cell loss and replacement with nonfunctioning fibrotic scarring [Frangogiannis, N. G., et al., Cardiovascular Res. 53(1): 31-47 (2002)]. Moreover, compensatory hypertrophy of viable cardiac muscle leads to microvascular insufficiency, which results in further demise in cardiac function by causing myocardial muscle hibernation and apoptosis of hypertrophied myocytes in the peri-infarct border zone.

Among survivors of myocardial infarction, residual cardiac function is influenced by the extent of ventricular remodeling (meaning changes in size, shape, and function, typically a progressive decline in function, of the heart after injury). Alterations in ventricular topography (meaning the shape, configuration, or morphology of a ventricle) occur in both infarcted and healthy cardiac tissue after myocardial infarction [Pfeffer, M. A., Braunwald, E., Circulation 81: 1161-72 (1990)]. Ventricular dilatation (meaning a stretching, enlarging or spreading out of the ventricle) causes a decrease in global cardiac function and is affected by the infarct size, infarct healing and ventricular wall stresses. Recent efforts to minimize remodeling have been successful by limiting infarct size through rapid reperfusion (meaning restoration of blood flow) using thrombolytic agents, and mechanical interventions, including, but not limited to, placement of a stent, along with reducing ventricular wall stresses by judicious use of pre-load therapies and proper after-load management [Pfeffer, M. A., Braunwald, E., Circulation 81: 1161-72 (1990)]. Regardless of these interventions, a substantial percentage of patients experience clinically relevant and long-term cardiac dysfunction after myocardial infarction [Sheiban, I. et al., J. Am. Coll. Cardiol. 38: 464-71 (2001)]. Despite revascularization of the infarct related artery circulation and appropriate medical management to minimize ventricular wall stresses, a significant percentage of these patients experience ventricular remodeling, permanent cardiac dysfunction, and consequently remain at an increased lifetime risk of experiencing adverse cardiac events, including death [Paul et al., Am. Heart J. 131: 710-15 (1996); Pfeffer, M. A., Braunwald, E., Circulation 81: 1161-72 (1990)].

At the cellular level, immediately following a myocardial infarction, transient generalized cardiac dysfunction uniformly occurs. In the setting of a brief (i.e., lasting three minutes to five minutes) coronary artery occlusion, energy metabolism is impaired, leading to demonstrable cardiac muscle dysfunction that can persist for up to 48 hours despite immediate reperfusion. This so-called "stunned myocardium phenomenon" occurs subsequent to or after reperfusion and is thought to be a result of reactive oxygen species. The process is transient and is not associated with an inflammatory response [Frangogiannis, N. G., et al., Cardiovascular Res. 53(1): 31-47 (2002)]. After successful revascularization, significant recovery from stunning occurs within three to four days, although complete recovery may take much longer [Boli, R., Prog. Cardiovascular Disease 40(6): 477-515 (1998); Sakata, K. et al., Ann. Nucleic Med. 8: 153-57 (1994); Wollert, K. C. et al., Lancet 364: 141-48 (2004)].

Inflammation

Coronary artery occlusion of more significant duration, i.e., lasting more than five minutes, leads to myocardial ischemia (i.e. an insufficient blood flow to the heart's muscle mass) and is associated with a significant inflammatory response that begins immediately after reperfusion and can last for up to several weeks [Frangogiannis, N. G., et al., Cardiovascular Res. 53(1): 31-47 (2002); Frangogiannis, N. G. et al., Circulation 98: 687-798 (1998)]. The inflammatory process following reperfusion is complex. Initially it contributes to myocardial damage but later leads to healing and scar formation. This complex process appears to occur in two phases. In the first so-called "hot" phase (within the first five days), reactive oxygen species (in the ischemic myocardial tissue) and complement activation generate a signal chemotactic for leukocytes (chemotaxis is the directed motion of a motile cell, organism or part towards environmental conditions it deems attractive and/or away from surroundings it finds repellent) and initiate a cytokine cascade [Lefer, D. J., Granger, D. N., Am. J. Med. 4:315-23 (2000); Frangogiannis, N. G., et al., Circulation 7:699-710 (1998)]. Mast cell degranulation, tumor necrosis factor alpha (TNFα) release, and increased interleukin-6 (IL-6), intercellular adhesion molecule 1 ("ICAM-1" or CD-54, a receptor typically expressed on endothelial cells and cells of the immune system), selectin (L, E and P) and integrin (CD11a, CD11b and CD18) expression all appear to contribute to neutrophil accumulation and degranulation in ischemic myocardium [Frangogiannis, N. G. et al., Circulation 7: 699-710 (1998), Kurrelmeyer, K. M, et al., Proc. Natl Acad. Sci USA. 10: 5456-61 (2000); Lasky, L. A., Science 258: 964-69 (1992); Ma, X. L., et al., Circulation 88(2): 649-58 (1993); Simpson, P. J. et al., J. Clin. Invest. 2: 624-29 (1998)]. Neutrophils contribute significantly to myocardial cell damage and death through microvascular obstruction and activation of neutrophil respiratory burst pathways after ligand-specific adhesion to cardiac myocytes [Entman, M. L., et al., J. Clin. Invest. 4: 1335-45 (1992)]. During the "hot" phase, angiogenesis is inhibited due to the release of angiostatic substances, including interferon gamma-inducible protein (IP 10) [Frangogiannis, N. G., et al., FASEB J. 15: 1428-30 (2001)].

In the second phase, the cardiac repair process begins (about day 6 to about day 14), which eventually leads to scar formation (about day 14 to about day 21) and subsequent ventricular remodeling (about day 21 to about day 90). Soon after reperfusion, monocytes infiltrate the infarcted myocardium. Attracted by complement (C5a), transforming growth factor B1 ("TGF-β1") and monocyte chemotactic protein 1 ("MCP-1"), monocytes differentiate into macrophages that initiate the healing process by scavenging dead tissue, regulating extracellular matrix metabolism, and inducing fibroblast proliferation [Birdshall, H. H., et al., Circulation 3: 684-92 (1997)]. Secretion of interleukin 10 (IL-10) by infiltrating lymphocytes also promotes healing by down-regulating inflammatory cytokines and influencing tissue remodeling [Frangogiannis, N. G. et al., J. Immunol. 5:2798-2808 (2000)]. Mast cells also appear to be involved in the later stages of myocardial repair by participating in the formation of fibrotic scar tissue. Stem Cell Factor (SCF) is a potent attractor of mast cells. SCF mRNA has been shown to be up-regulated in ischemic myocardial segments in a canine model of myocardial infarction and thus may contribute to mast cell accumulation at ischemic myocardial sites [Franigogiannis, N. G. et al., Circulation 98: 687-798 (1998)]. Mast cell products (including TGF-β, basic fibroblast growth factor (bFGF), vascular endothelial growth factor (VEGF) and gelatinases A and B) induce fibroblast proliferation, influence extracellular matrix metabolism, and induce angiogenesis [Fang, K. C., et al., J. Immunol. 162: 5528-35 (1999); Takeshi, S., et al., Cardiology 93: 168-74 (2000)].

Initiation of the Inflammatory Process

Complement Activation

Hill and Ward [Hill J H, Ward P A. The phlogistic role of C3 leukotactic fragment in myocardial infarcts of rats. J Exp Med 1971; 885-890] were the first to demonstrate that ischemic myocardial injury can activate the complement cascade in a rat model of myocardial infarction. Subsequently, Pinckard et al. [Pinckard R. N., Olson M. S., Giclas P. C., et al. Consumption of classical complement components by heart subcellular membranes in vitro and in patients after acute myocardial infarction. J Clin Invest 1975; 3:740-750] suggested that myocardial cell necrosis results in the release of subcellular membrane constituents rich in mitochondria, which are capable of triggering the early acting components (C1, C4, C2 and C3) of the complement cascade. Rossen et al. [Rossen R. D., Michael L. H., Hawkins H. K., et al. Cardiolipin-protein complexes and initiation of complement activation after coronary artery occlusion. Circ Res 1994; 3:546-555] have suggested that during myocardial ischemia, mitochondria, extruded through breaks in the sarcolemma, unfold and release membrane fragments rich in cardiolipin and protein. By binding C1 and supplying sites for the assembly of later acting complement components, these subcellular fragments provide the means to disseminate the complement-mediated inflammatory response to ischemic injury. mRNA and proteins for all the components of the classical complement pathway are up-regulated in areas of myocardial infarcts [Vakeva A. P., Agah A., Rollins S. A., et al. Myocardial infarction and apoptosis after myocardial ischemia and reperfusion: role of the terminal complement components and inhibition by anti-05 therapy. Circulation 1998; 22:2259-2267; Yasojima K., Kilgore K. S., Washington R. A., Lucchesi B. R., McGeer P. L. Complement gene expression by rabbit heart: up-regulation by ischemia and reperfusion. Circ Res 1998; 11:1224-1230].

Complement activation may play an important role in mediating neutrophil and monocyte recruitment in the injured myocardium. Dreyer et al. [Dreyer W. J., Michael L. H., Nguyen T., et al. Kinetics of C5a release in cardiac lymph of dogs experiencing coronary artery ischemia-reperfusion injury. Circ Res 1992; 6:1518-1524] showed that post-ischemic cardiac lymph contains leukocyte chemotactic activity, which is maximal during the first hour of reperfusion with washout within the next 3 hours.

Reactive Oxygen Species (ROS)

Reactive oxygen species (ROS) are molecules with unpaired electrons in their outer orbit. They have the potential to directly injure cardiac myocytes and vascular cells and may be involved in triggering inflammatory cascades through the induction of cytokines [Lefer D. J., Granger D. N. Oxidative stress and cardiac disease. Am J Med 2000; 4:315-323; Dhalla N. S., Elmoselhi A. B., Hata T., Makino N. Status of myocardial antioxidants in ischemia-reperfusion injury. Cardiovasc Res 2000; 3:446-456]. Reactive oxygen species have been shown to exert a direct inhibitory effect on myocardial function in vivo and have a critical role in the pathogenesis of myocardial stunning [Bolli R. Oxygen-derived free radicals and postischemic myocardial dysfunction ('stunned myocardium'). J Am Coll Cardiol 1988;

1:239-249]. In addition, evidence exists for a potential role of reactive oxygen in leukocyte chemotaxis [Granger D. N. Role of xanthine oxidase and granulocytes in ischemia-reperfusion injury. Am J Physiol 1988; 6(2):H1269-H1275]. Potential mechanisms through which reactive oxygen intermediates may generate a leukotactic stimulus include complement activation, induction of P-selectin expression, chemokine upregulation, and an increase in the ability of endothelial ICAM-1 to bind to neutrophils [Shingu M., Nobunaga M. Chemotactic activity generated in human serum from the fifth component of complement by hydrogen peroxide. Am J Pathol 1984; 2:201-206; Akgur F. M., Brown M. F., Zibari G. B., et al. Role of superoxide in hemorrhagic shock-induced P-selectin expression. Am J Physiol Heart Circ Physiol 2000; 2:H791-H797; Patel K. D., Zimmerman G. A., Prescott S. M., McEver R. P., McIntyre T. M. Oxygen radicals induce human endothelial cells to express GMP-140 and bind neutrophils. J Cell Biol 1991; 4:749-759; Lakshminarayanan V., Drab-Weiss E. A., Roebuck K. A. $H_2O_2$ and tumor necrosis factor-alpha induce differential binding of the redox-responsive transcription factors AP-1 and NF-kappa B to the interleukin-8 promoter in endothelial and epithelial cells. J Biol Chem 1998; 49:32670-32678; Lakshminarayanan V., Beno D. W., Costa R. H., Roebuck K. A. Differential regulation of interleukin-8 and intercellular adhesion molecule-1 by H2O2 and tumor necrosis factor-alpha in endothelial and epithelial cells. J Biol Chem 1997; 52:32910-32918; Sellak H., Franzini E., Hakim J., Pasquier C. Reactive oxygen species rapidly increase endothelial ICAM-1 ability to bind neutrophils without detectable up-regulation. Blood 1994; 9:2669-2677].

Most of the evidence implicating ROS in the pathophysiology of myocardial infarction is derived from investigations using free radical scavengers. Jolly et al. [Jolly S. R., Kane W. J., Bailie M. B., Abrams G. D., Lucchesi B. R. Canine myocardial reperfusion injury. Its reduction by the combined administration of superoxide dismutase and catalase. Circ Res 1984; 3:277-285] demonstrated that the combination of the antioxidant enzymes superoxide dismutase and catalase significantly reduced infarct size in dogs undergoing experimental myocardial ischemia and reperfusion. Other investigators found similar beneficial effects of antioxidant interventions in experimental models of myocardial infarction. However, there is a significant number of studies describing a failure of antioxidants to prevent injury or demonstrating an early protective effect, which waned with increased duration of reperfusion [Uraizee A., Reimer K. A., Murry C. E., Jennings R. B. Failure of superoxide dismutase to limit size of myocardial infarction after 40 minutes of ischemia and 4 days of reperfusion in dogs. Circulation 1987; 6:1237-1248; Gallagher K. P., Buda A. J., Pace D., Gerren R. A., Shlafer M. Failure of superoxide dismutase and catalase to alter size of infarction in conscious dogs after 3 hours of occlusion followed by reperfusion. Circulation 1986; 5:1065-1076; Richard V. J., Murry C. E., Jennings R. B., Reimer K. A. Therapy to reduce free radicals during early reperfusion does not limit the size of myocardial infarcts caused by 90 minutes of ischemia in dogs. Circulation 1988; 2:473-480]. Recently, transgenic mice that overexpress superoxide dismutase (SOD1) showed significant protection from post-ischemic injury and a significant decrease in infarct size in Langendorf-perfused hearts undergoing left coronary artery ligation [Wang P., Chen H., Qin H., et al. Overexpression of human copper, zinc-superoxide dismutase (SOD1) prevents post-ischemic injury. Proc Natl Acad Sci USA 1998; 8:4556-4560; Chen Z., Siu B., Ho Y. S., et al. Overexpression of MnSOD protects against myocardial ischemia/reperfusion injury in transgenic mice. J Mol Cell Cardiol 1998; 11:2281-2289]. Unfortunately, two clinical studies using recombinant human superoxide dismutase in patients with acute myocardial infarction undergoing thrombolysis [Murohara Y., Yui Y., Hattori R., Kawai C. Effects of superoxide dismutase on reperfusion arrhythmias and left ventricular function in patients undergoing thrombolysis for anterior wall acute myocardial infarction. Am J Cardiol 1991; 8:765-767.] or balloon angioplasty [Flaherty J. T., Pitt B., Gruber J. W., et al. Recombinant human superoxide dismutase (h-SOD) fails to improve recovery of ventricular function in patients undergoing coronary angioplasty for acute myocardial infarction. Circulation 1994; 5:1982-1991] demonstrated no significant improvement in left ventricular function. In addition, prolonged coronary occlusion (>2 h) is usually present in the clinical setting of reperfused myocardial infarction and may cause extensive irreversible myocardial damage, leaving fewer myocytes to be affected by free radical-mediated injury [Lefer D. J., Granger D. N. Oxidative stress and cardiac disease. Am J Med 2000; 4:315-323; Maxwell S. R., Lip G. Y. Reperfusion injury: a review of the pathophysiology, clinical manifestations and therapeutic options. Int J Cardiol 1997; 2:95-117].

Meldrum et al. [Meldrum D R, Dinarello C A, Cleveland J C, Jr, et al. Hydrogen peroxide induces tumor necrosis factor alpha mediated cardiac injury by a p38 mitogen activated protein kinase dependent mechanisms. Surgery. 1998; 124:291-296. discussion 297] demonstrated that $H_2O_2$ alone induced myocardial TNF-α mediated cardiac injury by a p38 mitogen-activated protein kinase (MAPK)-dependent mechanism. It has been hypothesized that reactive oxygen intermediates may generate a leukotatic stimulus that includes, complement activation, induction of hemorrhagic shock-induced P-selectin expression, chemokine up-regulation and an increase in the endothelial intercellular adhesion molecule (ICAM)-1 ability to bind neutrophils [Shingu M, Nobunaga M. Chemotactic activity generated in human serum from the fifth component of complement by hydrogen peroxide. Am J Pathol. 1984; 117:201-206; Akgur F M, Brown M F, Zibari G B, et al. Role of superoxide in hemorrhagic shock-induced P-selectin expression. Am J Physiol Heart Circ Physiol. 2000; 279:H791-H797; Lakshminarayanan V, Beno D W, Costa R H, Roebuck K A. Differential regulation of interleukin-8 and intercellular adhesion molecule-1 by $H_2O_2$ and tumor necrosis factor-alpha in endothelial and epithelial cells. J Biol Chem. 1997; 272:32910-32918; Sellak H, Franzini E, Hakim J, Pasquier C. Reactive oxygen species rapidly increase endothelial ICAM-1 ability to bind neutrophils without detectable up-regulation. Blood. 1994; 83:2669-2677]. It was reported that the use of the antioxidant enzymes superoxide dismutase and catalase reduced infarct size in dogs with myocardial ischemia and reperfusion [Jolly S R, Kane W J, Bailie M B, Abrams G D, Lucchesi B R. Canine myocardial reperfusion injury: its reduction by the combined administration of superoxide dismutase and catalase. Circ Res. 1984; 54:277-285]. However, failed studies have been reported where antioxidant treatment was used to prevent myocardial ischemic injury [Uraizee A, Reimer K A, Murry C E, Jennings R B. Failure of superoxide dismutase to limit size of myocardial infarction after 40 minutes of ischemia and 4 days of reperfusion in dogs. Circulation. 1987; 75:1237-1248; Gallagher K P, Buda A J, Pace D, Gerren R A, Shlafer M. Failure of superoxide dismutase and catalase to alter size of infarction in conscious dogs after 3 hours of occlusion followed by reperfusion. Circulation. 1986; 73:1065-1076].

For example, two clinical studies in which recombinant human superoxide dismutase was used in patients with an acute myocardial infarction undergoing percutaneous coronary intervention or thrombolysis showed no significant improvement of left ventricular function [Murohara Y, Yui Y, Hattori R, Kawai C. Effects of superoxide dismutase on reperfusion arrhythmias and left ventricular function in patients undergoing thrombolysis for anterior wall acute myocardial infarction. Am J Cardiol. 1991; 67:765-767; Flaherty J T, Pitt B, Gruber J W, et al. Recombinant human superoxide dismutase (h-SOD) fails to improve recovery of ventricular function in patients undergoing coronary angioplasty for acute myocardial infarction. Circulation. 1994; 89:1982-1991].

Cytokine Cascade

Experimental myocardial infarction is associated with the coordinated activation of a series of cytokine and adhesion molecule genes. A critical element in the regulation of these genes involves the complex formed by NF-κB and Iκβ [Lenardo M. J., Baltimore D. NF-kappa B: a pleiotropic mediator of inducible and tissue-specific gene control. Cell 1989; 2: 227-229]. NF-κB is activated by a vast number of agents, including cytokines (such as TNF-α and IL-1β) and free radicals. Cytokines can self-amplify through a positive feedback loop targeting the nuclear factor (NF)-κB. Up-regulation of TNF-α in the infarct myocardium can up-regulate the levels of TNF-α in the neighboring normal myocardium, leading to amplified cytokine effects [Irwin M, Mak S, Mann D L, et al. Tissue expression and immunolocalization of tumor necrosis factor-alpha in post infarction-dysfunctional myocardium. Circulation. 1999; 99:1492-1498]. TNF-α stimulates expression of pro-inflammatory cytokines, chemokines and adhesion molecules by leukocytes and endothelial cells, and regulates extracellular matrix metabolism by reducing collagen synthesis and by enhancing matrix metalloprotease (MMP) activity in cardiac fibroblasts; other adhesive cytokines, such as monocyte chemoattractant protein (MCP)-1, are also induced in the ischemic and re-perfused canine myocardium [Siwik D A, Chang D L, Coluci W S. Interleukin-1 beta and tumor necrosis factor-alpha decrease collagen synthesis and increase matrix metalloproteinase activity in cardiac fibroblasts in vitro. Circ Res. 2000; 86:1259-1265]. Kumar et al. [Kumar A G, Ballantyne C M, Michael L H, et al. Induction of monocyte chemoattractant protein-1 in the small veins of the ischemic and re-perfused canine myocardium. Circulation. 1997; 95:693-700] suggested that MCP-1 μlays a significant role in monocyte trafficking in re-perfused myocardium.

The mechanisms responsible for triggering the cytokine cascade in the infarcted myocardium have only recently been investigated. Several studies have indicated a role for preformed mast cell-derived mediators in initiating the cytokine cascade ultimately responsible for ICAM-1 induction in the re-perfused canine myocardium [Frangogiannis N. G., Lindsey M. L., Michael L. H., et al. Resident cardiac mast cells de-granulate and release preformed TNF-alpha, initiating the cytokine cascade in experimental canine myocardial ischemia/reperfusion. Circulation 1998; 7:699-710; Frangogiannis N. G., Entman M. L. Mast cells in myocardial ischaemia and reperfusion, Mast cells and basophils in physiology, pathology and host defense. In: Marone G., Liechtenstein L. M., Galli S. J., editors. London: Academic Press; 2000. p. 507-522; Frangogiannis N. G., Burns A. R., Michael L. H., Entman M. L. Histochemical and morphological characteristics of canine cardiac mast cells. Histochem J 1999; 4:221-229]. Mast cells have been recognized as an important source of preformed and newly synthesized cytokines, chemokines and growth factors [Frangogiannis N. G., Lindsey M. L., Michael L. H., et al. Resident cardiac mast cells de-granulate and release preformed TNF-alpha, initiating the cytokine cascade in experimental canine myocardial ischemia/reperfusion. Circulation 1998; 7:699-710; Frangogiannis N. G., Entman M. L. Mast cells in myocardial ischaemia and reperfusion, Mast cells and basophils in physiology, pathology and host defense. In: Marone G., Liechtenstein L. M., Galli S. J., editors. London: Academic Press; 2000. p. 507-522; Frangogiannis N. G., Burns A. R., Michael L. H., Entman M. L. Histochemical and morphological characteristics of canine cardiac mast cells. Histochem J 1999; 4:221-229]. Gordon and Galli [Gordon J R, Galli S J. Mast cells as a source of both preformed and immunologically inducible TNF-alpha/cachectin. Nature 1990; 274-276; Gordon J. R., Burd P. R., Galli S. J. Mast cells as a source of multifunctional cytokines Immunol Today 1990; 12:458-464] identified mouse peritoneal mast cells as an important source of both preformed and immunologically-induced TNF-α. The constitutive presence of TNF-α in canine cardiac mast cells have led to the hypothesis that mast cell-derived TNF-α may be released following myocardial ischemia, representing an 'upstream' cytokine responsible for initiating the inflammatory cascade [Frangogiannis N G, Cardiovascular Research (2002) Vol. 53, Issue 1, pp. 31-47].

Moreover, it has been reported that early post-ischemic cardiac lymph is capable of inducing IL-6 expression in canine mononuclear cells in vitro. Incubation with a neutralizing antibody to TNF-α in part inhibited IL-6 up-regulation, suggesting an important role for TNF-α as the upstream cytokine inducer. Mast cell degranulation appears to be confined in the ischemic area and results in rapid release of TNF-α, inducing IL-6 in infiltrating mononuclear cells [Frangogiannis N G, Cardiovascular Research (2002) Vol. 53, Issue 1, pp. 31-47; 56, 61].

The role of TNF-α in myocardial infarction is thought to be more complex than simply serving as a trigger of a cytokine cascade [Sack M. N., Smith R. M., Opie L. H. Tumor necrosis factor in myocardial hypertrophy and ischemia—an anti-apoptotic perspective. Cardiovasc Res 2000; 3:688-695; Belosjorow S., Schulz R., Dorge H., Schade F. U., Heusch G. Endotoxin and ischemic preconditioning: TNF-alpha concentration and myocardial infarct development in rabbits. Am J Physiol 1999; 6(2):H2470-H2475]. Recent experiments using TNFR1/TNFR2 double receptor knockout mice undergoing left coronary artery ligation had significantly larger infarct size and increased myocyte apoptosis when compared with wild-type controls [Kurrelmeyer K. M., Michael L. H., Baumgarten G., et al. Endogenous tumor necrosis factor protects the adult cardiac myocyte against ischemic-induced apoptosis in a murine model of acute myocardial infarction. Proc Natl Acad Sci USA 2000; 10:5456-5461]. These findings suggested that TNF-α may induce a cytoprotective signal capable of preventing or delaying the development of myocyte apoptosis following myocardial infarction.

Other studies have shown that TNF-α expression during the healing phase was not confined to the infarct or peri-infarct zone, but was also localized in the normal non-infarcted myocardium, in which remodeling was ongoing. Thus, sustained TNF-α expression may have a role in the reparative process following myocardial infarction [Irwin M. W., Mak S., Mann D. L., et al. Tissue expression and immunolocalization of tumor necrosis factor-alpha in post-infarction dysfunctional myocardium. Circulation 1999;

11:1492-1498; Jacobs M., Staufenberger S., Gergs U., et al. Tumor necrosis factor-alpha at acute myocardial infarction in rats and effects on cardiac fibroblasts. J Mol Cell Cardiol 1999; 11:1949-1959].

Cytokine and Chemokine Upregulation

Chemokine up-regulation is a noted feature of the post-infarction inflammatory response (Table 1) [Frangogiannis N G. Chemokines in ischemia and reperfusion. Thromb Haemost. 2007; 97:738-747]. Investigators have demonstrated strong induction of several chemokines in the ischemic myocardium, supporting their role in leukocyte recruitment [Birdsall H H, Green D M, Trial J, et al. Complement C5a, TGF-beta 1, and MCP-1, in sequence, induce migration of monocytes into ischemic canine myocardium within the first one to five hours after reperfusion. Circulation. 1997; 95:684-692]. MCP-1 up-regulation has been demonstrated in a mouse model [Tarzami S T, Cheng R, Miao W, Kitsis R N, Berman J W. Chemokine expression in myocardial ischemia: MIP-2 dependent MCP-1 expression protects cardiomyocytes from cell death. J Mol Cell Cardiol. 2002; 34:209-221]. Frangogiannis reported that a MCP-1−/− infarct mouse model had decreased messenger ribonucleic acid (mRNA) expression of the cytokines TNF-α, IL-1β, TGF-β and IL-10, and showed defective macrophage differentiation [Frangogiannis N G. Chemokines in ischemia and reperfusion. Thromb Haemost. 2007; 97:738-747]. Cytokines, such as TNF-α and IL-6, are rapidly released in the central zone during a myocardial infarction; however, they are usually maximal in the border zone [Irwin M, Mak S, Mann D L, et al. Tissue expression and immunolocalization of tumor necrosis factor-alpha in post infarction-dysfunctional myocardium. Circulation. 1999; 99:1492-1498; Gwechenberger M, Mendoza L H, Youker K A, et al. Cardiac myocytes produce interleukin-6 in culture and in viable border zone of re-perfused infarctions. Circulation. 1999; 99:546-551]. This robust up-regulation may return to baseline levels if the infarction is small; if the infarction is large and the inflammatory response is excessive, there can be sustained cytokine up-regulation, corresponding to a chronic remodeling phase.

TABLE 1

Up-regulated chemokines and their role after myocardial ischemia and reperfusion.

| Chemokine | Action After Myocardial Ischemia and Reperfusion |
| --- | --- |
| CXCL8/Interleukin (IL)-8 | Induce neutrophil infiltration |
| CCL2/Monocyte Chemoattractant Protein (MCP)-1 | Regulate monocyte and lymphocyte recruitment |
| CCL3/Macrophage Inflammatory Protein (MIP)-1α | Regulate monocyte and lymphocyte recruitment |
| CCL4/Macrophage Inflammatory Protein (MIP)-1β | Regulate monocyte and lymphocyte recruitment |
| CXCL10/Interferon-10 | Angiostatic factor with anti-fibrotic properties |

[taken from Nah D-Y, Rhee M-Y, Korean Circ. J. October 2009; 39(10): 393-398]

Cell-Mediated Inflammatory Response to Myocardial Infarction

Neutrophils

Neutrophils are recruited during the initial stage of cardiac ischemic injury. Neutrophil transmigration in the infarcted myocardium requires adhesive interactions with activated vascular endothelial cells. Neutrophils may secrete oxidants and proteases and possibly express mediators capable of amplifying cell recruitment [Frangogiannis N G, Youker K A, Entman M L. The role of the neutrophil in myocardial ischemia and reperfusion. EXS. 1996; 76:263-284]. Neutrophil depletion in animals undergoing re-perfused myocardial infarction has been reported to significantly decrease the infarct size, suggesting that a significant amount of myocardial injury may be induced by neutrophil dependent mechanisms [Romson J L, Hook B G, Kunkel S L, Abrams G D, Schork M A, Lucchesi B R. Reduction of the extent of ischemic myocardial injury by neutrophil depletion in the dog. Circulation. 1983; 67:1016-1023; Jordan J E, Zhao Z Q, Vinten-Johansen J. The role of neutrophils in myocardial ischemia-reperfusion injury. Cardiovasc Res. 1999; 43:860-878].

The mechanisms associated with neutrophil-induced myocardial ischemic injury have not been identified. Jaeschke et al. [Jaeschke H, Smith C W. Mechanisms of neutrophil-induced parenchymal cell injury. J Leukoc Biol. 1997; 61:647-653] suggested that neutrophils may directly injure parenchymal cells through release of specific toxic products. While selectins have been implicated, there have been inconsistent results of selectin-related interventions in experimental models of myocardial ischemia [Jones S P, Girod W G, Granger D N, Palazzo A J, Lefer D J. Reperfusion injury is not affected by blockade of P-selectin in the diabetic mouse heart. Am J Physiol. 1999; 277:H763-H769; Birnbaum Y, Patterson M, Kloner R A. The effect of CY1503, a sialyl Lewis X analog blocker of the selectin adhesion molecules, on infarct size and "no reflow" in the rabbit model of acute myocardial infarction/reperfusion. J Mol Cell Cardiol. 1997; 29:2013-2025]. The selectin family consists of L-selectin, P-selectin and E-selectin. P-selectin expression occurs rapidly in endothelial cells during cardiac ischemic injury. Experimental studies have suggested that monoclonal antibodies against P-selectin reduced myocardial necrosis, preserving coronary endothelial function and attenuating neutrophil infiltration in ischemic and reperfused myocardium [Palazzo A J, Jones S P, Anderson D C, Granger D N, Lefer D J. Coronary endothelial P-selectin in pathogenesis of myocardial ischemia-reperfusion injury. Am J Physiol. 1998; 275:H1865-H1872].

Mononuclear Cells

MCP-1/CCL2 plays an important role in monocyte recruitment to the infarcted myocardium [Dewald O, Zymek P, Winkelmann K, et al. CCL2/monocyte chemoattractant protein-1 regulates inflammatory responses critical to healing myocardial infarcts. Circ Res. 2005; 96:881-889]. Cytokines, such as TGF-β, free radical oxygen, complement, and the CC chemokines (e.g., MCP-1) may also play a role in monocyte infiltration. Infiltration of monocytes into the infarcted myocardium is followed by maturation and differentiation of these blood-derived cells into macrophages.

Cardiac Repair after Myocardial Infarction

TGF-β as a Key Regulator in Cardiac Repair

TGF-β is a multifunctional cytokine that controls proliferation and cellular differentiation in most cells. The exact role of TGF-β signaling in the infarcted and remodeled heart is poorly understood. Its role in myocardial infarction is thought to involve cardiomyocyte hypertrophy, angiogenic or angiostatic effects, reduced adhesion molecule expression, macrophage deactivation, chemokine and cytokine repression, myofibroblast differentiation, fibroblast proliferation and extracellular matrix protein synthesis [Nah D-Y, Rhee M-Y, Korean Circ. J. October 2009; 39(10): 393-39847; Frangogiannis N G. The immune system and cardiac repair. Pharmacol Res. 2008; 58:88-111].

TGF-β was shown to be significantly up-regulated and TGF-β mRNA and protein was significantly increased at the infarct border zone in an experimental rat model of myocardial infarction [Thompson N L, Bazoberry F, Speir E H, et al. Transforming growth factor beta-1 in acute myocardial infarction in rats. Growth Factors. 1988; 1:91-99; Dean R G, Balding L C, Candido R, et al. Connective tissue growth factor and cardiac fibrosis after myocardial infarction. J Histochem Cytochem. 2005; 53:1245-1256]. During infarct healing, TGF-β may play a role in the suppression of chemokine and cytokine synthesis and is thought to be a key mediator of the transition from inflammation to fibrosis [Bassols A, Massague J. TGF-13 regulates the expression and structure of extracellular matrix chondroitin/dermatan sulfate proteoglycans. J Biol Chem. 1988; 263:3039-3045]. Lefer et al. [Lefer A M, Tsao P, Aoki N, Palladino M A., Jr Mediation of cardio-protection by transforming growth factor-beta. Science. 1990; 249:61-64] reported that TGF-β injections reduced myocardial ischemic injury mediated by pro-inflammatory cytokines such as TNF-α during the inflammatory phase of myocardial healing. Anti-TGF-β treatment before or after coronary artery ligation increased mortality and worsened the left ventricular remodeling in mice with non-re-perfused myocardial infarction [Frantz S, Hu K, Adammek A, et al. Transforming growth factor beta inhibition increases mortality and left ventricular dilatation after myocardial infarction. Basic Res Cardiol. 2008; 103: 485-492]. The inhibition of TGF-β signaling by injection of a TGF-β II receptor resulted in reduction of left ventricular remodeling by modulation of cardiac fibrosis; early TGF-β inhibition increased mortality and left ventricular dilatation [Ikeuchi M, Tsutsui H, Shiomi T, et al Inhibition of TGF-beta signaling exacerbates early cardiac dysfunction but prevents late remodeling after infarction. Cardiovasc Res. 2004; 64:526-535; Okada H, Takemura G, Kosai K, et al., Postinfarction gene therapy against transforming growth factor-beta signal modulates infarct tissue dynamics and attenuates left ventricular remodeling and heart failure. Circulation. 2005; 111:2430-2437]. Youn et al. [Youn T J, Kim H S, Oh B H. Ventricular remodeling and transforming growth factor-beta 1 mRNA expression after nontransmural myocardial infarction in rats: effects of angiotensin converting enzyme inhibition and angiotensin II type 1 receptor blockade. Basic Res Cardiol. 1999; 94:246-253] reported that an angiotensin converting enzyme inhibitor and angiotensin receptor blockade resulted in decreased TGF-β mRNA expression after non-transmural infarction in the rat.

Other Cytokines in Cardiac Repair

Three IL-1 molecules (IL-1α, IL-β and IL-1 Ra) that are specific receptor antagonists [Dinarello C A. Biologic basis for interleukin-1 in disease. Blood. 1996; 87:2095-2147] have been implicated in cardiac repair. Bujak et al. [Bujak M, Dobaczewski M, Chatila K, et al. Interleukin-1 receptor type I signaling critically regulates infarct healing and cardiac remodeling. Am J Pathol. 2008; 173:57-67] demonstrated that IL-1 signaling is essential for activation of inflammatory and fibrogenic pathways in the healing infarct and plays an important role in the pathogenesis of remodeling after infarction.

IL-10 exerts potent anti-inflammatory effects and modulates MMP expression [de Waal Malefyt R, Abrams J, Bennett B, Figdor C G, de Vries J E. Interleukin 10 (IL-10) inhibits cytokine synthesis by human monocytes: an autoregulatory role of IL-10 produced by monocytes. J Exp Med. 1991; 174:1209-1220; Moore K W, deWaal Malefyt R, Coffman R L, O'Garra A. Interleukin-10 and the interleukin-10 receptor. Annu Rev Immunol. 2001; 19:683-765; Lacraz S, Nicod L P, Chicheportiche R, Welgus H G, Dayer J M. IL-10 inhibits metalloproteinase and stimulates TIMP-1 production in human mononuclear phagocytes. J Clin Invest. 1995; 96:2304-2310]. However, Zymek et al. [Zymek P, Nah D Y, Bujak M, et al. Interleukin-10 is not a critical regulator of infarct healing and left ventricular remodeling. Cardiovasc. Res. 2007; 74:313-322] reported that IL-10 signaling plays a noncritical role in the suppression of inflammatory mediators, resolution of the inflammatory response and fibrous tissue deposition following myocardial infarction in the mouse; which may be due to the involvement of multiple overlapping regulatory mechanisms controlling various pro-inflammatory pathways activated in the infarcted myocardium.

Proteins in Cardiac Repair

Cluster of differentiation 44 (CD44) is a cell surface glycoprotein involved in cell-cell interaction and cell adhesion and migration. CD44-hyaluronan interactions play a role in leukocyte extravasation at the inflammatory site and serves as a key factor in the resolution of inflammation through removal of matrix breakdown products and clearance of apoptotic neutrophils [Mikecz K, Brennan F R, Kim J H, Glant T T. Anti-CD44 treatment abrogates tissue edema and leukocyte infiltration in murine arthritis. Nat Med. 1995; 1:558-563; DeGrendele H C, Estess P, Siegelman M H. Requirement for CD44 in activated T cell extravasation into an inflammatory site. Science. 1997; 278:672-675; Teder P, Vandivier R W, Jiang D, et al. Resolution of lung inflammation by CD44. Science. 2002; 296:155-158]. Huebener et al. [Huebener P, Abou-Khamis T, Zymek P, et al. CD44 is critically involved in infarct healing by regulating the inflammatory and fibrotic response. J Immunol. 2008; 180: 2625-2633] tested the role of CD44 in infarct healing and demonstrated that CD44 mRNA levels were significantly induced in the infarcted heart; CD44 null mice showed enhanced and prolonged inflammation in the infarcted heart followed by decreased myofibroblast infiltration, reduced collagen deposition and diminished proliferative activity. Huebener et al. concluded that CD44 is critically involved in infarct healing by regulating the inflammatory and fibrotic response.

Thrombospondin (TSP)-1 is a TGF-β activator as well as an adhesive glycoprotein involved in cell-to-cell and cell-to-matrix interaction with potent angiostatic properties [Lawler J. Thrombospondin-1 as an endogenous inhibitor of angiogenesis and tumor growth. J Cell Mol Med. 2002; 6:1-12]. TSP-1 showed selective localization in the infarct border zone, and TSP-1 knockout animals had markedly increased macrophage and myofibroblast density in the infarct and in remodeling of non-infarcted myocardial areas, and was more extensive in post-infarction remodeling than in wild-type mice. Frangogiannis et al. [Frangogiannis N G, Ren G, Dewald O, et al. The critical role of endogenous thrombospondin (TSP)-1 in preventing expansion of healing myocardial infarcts. Circulation. 2005; 111:2935-2942] concluded that the selective endogenous expression of TSP-1 at the infarct border zone may serve as a "barrier," limiting expansion of granulation tissue and protecting the non-infarcted myocardium from fibrotic remodeling.

Smad is an essential protein component of the TGF-β pathway [Shi Y, Massague J. Mechanisms of TGF-beta signaling from cell membrane to the nucleus. Cell. 2003; 113:685-700]. Hao et al. [Hao J, Ju H, Zhao S, Junail A, Scammell-La Fleur T, Dixon I M. Elevation of expression of Smads 2, 3, and 4, decorin and TGF-beta in the chronic phase of myocardial infarct scar healing. J Mol Cell Cardiol. 1999; 31:667-678] showed that TGF-β mRNA was significantly increased in the infarct scar compared to viable myocardium, and that Cardiac Smad 2, 3 and 4 proteins were significantly increased in the border and scar tissues when compared to viable myocardium, suggesting that TGF-β/Smad signaling may be involved in the remodeling of the infarct scar.

The reparative phase of healing involves activation of proteinases, which are critical for cell migration and extracellular matrix remodeling. Recent studies have demonstrated that deficiency of urokinase-type plasminogen activator (uPA) protected mice undergoing left coronary artery ligation against myocardial rupture [Heymans S., Luttun A., Nuyens D., et al. Inhibition of plasminogen activators or matrix metalloproteinases prevents cardiac rupture but impairs therapeutic angiogenesis and causes cardiac failure. Nat Med 1999; 10:1135-1142]. However, uPA−/− mice also showed impaired scar formation and infarct neovascularization. Furthermore, plasminogen-deficient mice showed a profound disturbance in healing, suggesting a crucial role for the proteolytic system in regulating cardiac repair [Creemers E., Cleutjens J., Smits J., et al. Disruption of the plasminogen gene in mice abolishes wound healing after myocardial infarction. Am J Pathol 2000; 6:1865-1873].

Matrix metalloproteinase (MMP) expression is upregulated in the infarcted myocardium and may have a prominent role in extracellular matrix remodeling. Administration of MMP inhibitors and targeted deletion of MMP-9 attenuated left ventricular enlargement in murine myocardial infarction [Cleutjens J. P., Kandala J. C., Guarda E., Guntaka R. V., Weber K. T. Regulation of collagen degradation in the rat myocardium after infarction. J Mol Cell Cardiol 1995; 6:1281-1292; Lu L., Gunja-Smith Z., Woessner J. F., et al. Matrix metalloproteinases and collagen ultrastructure in moderate myocardial ischemia and reperfusion in vivo. Am J Physiol Heart Circ Physiol 2000; 2:H601-H609; Rohde L. E., Ducharme A., Arroyo L. H., et al. Matrix metalloproteinase inhibition attenuates early left ventricular enlargement after experimental myocardial infarction in mice. Circulation 1999; 23:3063-30701; Ducharme A., Frantz S., Aikawa M., et al. Targeted deletion of matrix metalloproteinase-9 attenuates left ventricular enlargement and collagen accumulation after experimental myocardial infarction. J Clin Invest 2000; 1:55-62].

Cardiac Fibroblasts and Extracellular Matrix Remodeling
Cardiac Fibroblasts

In the healthy heart, 70% of the cells present are fibroblasts [Jugdutt B I. Ventricular remodeling after infarction and the extracellular collagen matrix: when is enough enough? Circulation. 2003; 108:1395-403; Banerjee I, Fuseler J W, Price R L, Borg T K, Baudino T A. Determination of cell types and numbers during cardiac development in the neonatal and adult rat and mouse. Am J. Physiol Heart Circul Physiol. 2007; 293:H1883-91]. Fibroblasts are widely distributed connective tissue cells that are found in all vertebrate organisms. They are usually defined as cells of mesenchymal origin that produce a variety of extracellular matrix (ECM) components, including multiple collagens, as well as fibronectin [Eghbali-Webb M. Molecular Biology Intelligence Unit Molecular Biology of Collagen Matrix in the Heart. Austin, Tex.: Landes; 1994; Kanekar S, Hirozanne T, Terracio L, Borg T K. Cardiac fibroblasts: form and function. Cardiovasc Pathol. 1998; 7: 127-133]. Morphologically, fibroblasts are flat, spindle-shaped cells with multiple processes emanating from the main cell body. Fibroblasts lack a basement membrane, a characteristic feature that separates them from the other permanent cell types of the heart, all of which do contain a basement membrane.

Fibroblasts produce extracellular matrix constituents needed to support cell ingrowth. Willems et al. [Willems I. E., Havenith M. G., De Mey J. G., Daemen M. J. The alpha-smooth muscle actin-positive cells in healing human myocardial scars. Am J Pathol 1994; 4:868-875] previously identified and characterized interstitial nonvascular α-smooth muscle actin (α-SMAc) positive cells, which were present in human myocardial scars 4-6 days after an infarction. These cells are phenotypically modulated fibroblasts, termed myofibroblasts, that develop ultra-structural and phenotypic characteristics of smooth muscle cells and are the predominant source of collagen mRNA in healing myocardial infarcts [Gabbiani G. Evolution and clinical implications of the myofibroblast concept. Cardiovasc Res 1998; 3:545-548]. Myofibroblasts are undifferentiated cells that may be capable of assuming a variety of different roles, such as extracellular matrix metabolism, neovessel formation and contractile activity [Cleutjens J. P., Verluyten M. J., Smiths J. F., Daemen M. J. Collagen remodeling after myocardial infarction in the rat heart. Am J Pathol 1995; 2:325-338; Serini G., Gabbiani G. Mechanisms of myofibroblast activity and phenotypic modulation. Exp Cell Res 1999; 2:273-283; Cleutjens J. P., Blankesteijn W. M., Daemen M. J., Smits J. F. The infarcted myocardium: simply dead tissue, or a lively target for therapeutic interventions. Cardiovasc Res 1999; 2:232-241]. TGF-β appears to play an important role in myofibroblast differentiation during wound healing by regulating α-SMAc expression in these cells [Desmouliere A., Geinoz A., Gabbiani F., Gabbiani G. Transforming growth factor-beta 1 induces alpha-smooth muscle actin expression in granulation tissue myofibroblasts and in quiescent and growing cultured fibroblasts. J Cell Biol 1993; 1:103-111].

Myofibroblasts are essential for scar formation following myocardial infarction (MI). However, their persistence can contribute to fibrosis and adverse myocardial remodeling, particularly if they remain active in otherwise healthy areas of the heart away from the site of injury. This reactive fibrosis is characterized by increased extracellular matrix and increases the likelihood of arrhythmias [van den Borne S W, Diez J, Blankesteijn W M, Verjans J, Hofstra L, Narula J. Myocardial remodeling after infarction: the role of myofibroblasts. Nat Rev Cardiol. 2010; 7:30-7]. Similarly, the direct coupling of cardiomyocytes to myofibroblasts increases the likelihood of arrhythmias, in contrast to non-activated fibroblasts [Rohr S. Myofibroblasts in diseased hearts: new players in cardiac arrhythmias? Heart Rhythm. 2009; 6:848-56; Thompson S A, Copeland C R, Reich D H, Tung L. Mechanical coupling between myofibroblasts and cardiomyocytes slows electric conduction in fibrotic cell monolayers. Circulation. 2011; 123:2083-93; Rosker C, Salvarani N, Schmutz S, Grand T, Rohr S. Abolishing myofibroblast arrhythmogeneicity by pharmacological ablation of alpha-smooth muscle actin containing stress fibers. Circulation Research. 2011; 109:1120-31]. This reactive ongoing fibrosis leads to increased myocardial stiffness that contributes to systolic and diastolic dysfunction and heart failure progression [Pfeffer M A, Braunwald E. Ventricular remodeling after myocardial infarction. Experimental observations and clinical implications. Circulation. 1990; 81:1161-72; Swynghedauw B. Molecular mechanisms of myocardial remodeling. Physiol Rev. 1999; 79:215-62]. Over time, the density of myofibroblasts generally decreases following MI, however, these cells can persist in significant numbers for years [Clanachan A S, Jaswal J S, Gandhi M, Bottorff D A, Coughlin J, Finegan B A, et al. Effects of inhibition of myocardial extracellular-responsive kinase and P38 mitogen-activated protein kinase on mechanical function of rat hearts after prolonged hypothermic ischemia.

Transplantation. 2003; 75:173-80; Yada M, Shimamoto A, Hampton C R, Chong A J, Takayama H, Rothnie C L, et al. FR167653 diminishes infarct size in a murine model of myocardial ischemia reperfusion injury. J Thorac Cardiovasc Surg. 2004; 128:588-94; Capano M, Crompton M. Bax translocates to mitochondria of heart cells during simulated ischaemia: involvement of AMP-activated and p38 mitogen-activated protein kinases. Biochem J. 2006; 395:57-64; Aleshin A, Sawa Y, Ono M, Funatsu T, Miyagawa S, Matsuda H. Myocardial protective effect of FR167653; a novel cytokine inhibitor in ischemic-reperfused rat heart. Eur J Cardiothorac Surg. 2004; 26:974-80; Gorog D A, Tanno M, Cao X, Bellahcene M, Bassi R, Kabir A M, et al Inhibition of p38 MAPK activity fails to attenuate contractile dysfunction in a mouse model of low-flow ischemia. Cardiovascular research. 2004; 61:123-31].

After the initial myocardial cell death induced by ischemia, the heart quickly begins to promote the migration of fibroblasts. In the healing wound, fibroblasts proliferate and differentiate into myofibroblasts that take on features resembling smooth muscle cells [Brown R D, Ambler S K, Mitchell M D, Long C S. The cardiac fibroblast: therapeutic target in myocardial remodeling and failure. Annu Rev Pharmacol Toxicol. 2005; 45:657-87; Brown R D, Ambler S K, Mitchell M D, Long C S. The cardiac fibroblast: therapeutic target in myocardial remodeling and failure. Annu Rev Pharmacol Toxicol. 2005; 45:657-87; Dobaczewski M, Gonzalez-Quesada C, Frangogiannis N G. The extracellular matrix as a modulator of the inflammatory and reparative response following myocardial infarction. J Mol Cell Cardiol. 2010; 48:504-11].

Extracellular Matrix Remodeling

Remodeling is broadly defined as changes in the organization of the myocardium, and is a critical process that allows the heart to adapt to changes in mechanical, chemical and electrical signals [Brower G L, Chancey A L, Thanigaraj S, Matsubara B B, Janicki J S. Cause and effect relationship between myocardial mast cell number and matrix metalloproteinase activity. Am J Physiol Heart Circ Physiol. 2002; 283: H518-H525; Chancey A L, Brower G L, Janicki J S. Cardiac mast cell-mediated activation of gelatinase and alteration of ventricular diastolic function. Am J Physiol Heart Circ Physiol. 2002; 282: H2152-H2158; Stewart J A Jr, Wei C C, Brower G L, Rynders P E, Hankes G H, Dillon A R, Lucchesi P A, Janicki J S, Dell'Italia L J. Cardiac mast cell- and chymase-mediated matrix metalloproteinase activity and left ventricular remodeling in mitral regurgitation in the dog. J Mol Cell Cardiol. 2003; 35: 311-319]. Cardiac fibroblasts are key components of this process, because of their ability to secrete and breakdown the ECM. Degradation of collagen requires the presence of matrix metalloproteinases (MMPs) [Raffetto J D, Khalil R A. Matrix metalloproteinases and their inhibitors in vascular remodeling and vascular disease. Biochem Pharmacol. 2008; 75: 346-359; Visse R, Nagase H. Matrix metalloproteinases and tissue inhibitors of metalloproteinases: structure, function, and biochemistry. Circ Res. 2003; 92: 827-839]. In the normal heart, MMP expression and function are tightly regulated; however, in pathological states, MMP expression and activity are increased, leading to excessive ECM degradation, which can have profound effects on cardiac function. Following cardiac injury, fibroblast function can be influenced by chemical signals (e.g., cytokines, matrikines and growth factors) in a paracrine or autocrine manner. These factors can cause changes in fibroblast gene expression, as well as cell migration to the injured region to promote wound healing and scar formation.

Depending on the stage of heart failure, there can be considerable myocyte hypertrophy and cell death. Dilatation can also be observed in later stages; however, present at every stage are changes in the ECM, which are regulated by cardiac fibroblasts. There is also activation and differentiation of cardiac fibroblasts into myofibroblasts [Brown R D, Ambler S K, Mitchell M D, Long C S. The cardiac fibroblast: therapeutic target in myocardial remodeling and failure. Annu Rev Pharmacol Toxicol. 2005; 45: 657-687; Weber K T. Fibrosis in hypertensive heart disease: focus on cardiac fibroblasts. J Hypertens. 2004; 22: 47-50; Frangogiannis N G, Michael L H, Entman M L. Myofibroblasts in re-perfused myocardial infarcts express the embryonic form of smooth muscle myosin heavy chain. Cardiovasc Res. 2000; 48: 89-100]. After maturation to myofibroblasts, an increase in the synthesis and secretion of fibronectin is observed [Gabbiani G. The myofibroblast in wound healing and fibrocontractive diseases. J Pathol. 2003; 200: 500-503]. As the heart undergoes remodeling associated with heart failure, an increase in cytokine and growth factor secretion is observed. In response to these various factors, myofibroblasts begin to proliferate, migrate and remodel the cardiac interstitium through increased secretion of MMPs and collagen [Brown R D, Ambler S K, Mitchell M D, Long C S. The cardiac fibroblast: therapeutic target in myocardial remodeling and failure Annu Rev Pharmacol Toxicol. 2005; 45: 657-687; Weber K T. Fibrosis in hypertensive heart disease: focus on cardiac fibroblasts. J Hypertens. 2004; 22: 47-50; Lindsey M L, Escobar G P, Mukherjee R, Goshorn D K, Sheats N J, Bruce J A, Mains I M, Hendrick J K, Hewett K W, Gourdie R G, Matrisian L M, Spinale F G. Matrix metalloproteinase-7 affects connexin-43 levels, electrical conduction, and survival after myocardial infarction. Circulation. 2006; 113: 2919-2928; Raizman J E, Komijenovic J, Chang R, Deng C, Bedosky K M, Rattan S G, Cunnington R H, Freed D H, Dixon I M. The participation of the Na+-Ca2+ exchanger in primary cardiac myofibroblast migration, contraction and proliferation. J Cell Physiol. 2007; 213: 540-551]. To further stimulate the remodeling process, cardiac fibroblasts secrete increased amounts of growth factors and cytokines, specifically IL-1β, IL-6, and tumor necrosis factor (TNF)-α, which, in turn, activate MMPs, leading to further cardiac remodeling [Brown R D, Ambler S K, Mitchell M D, Long C S. The cardiac fibroblast: therapeutic target in myocardial remodeling and failure Annu Rev Pharmacol Toxicol. 2005; 45: 657-687; Corda S, Samuel J L, Rappaport L. Extracellular matrix and growth factors during heart growth. Heart Fail Rev. 2000; 5: 119-130; Brown R D, Mitchell M D, Long C S. Proinflammatory cytokines and cardiac extracellular matrix: regulation of fibroblast phenotype. In: Villarreal F J, ed. Interstitial Fibrosis in Heart Disease. New York: Springer; 2004: 57-81]. Initially, all of these changes are critical to the reparative wound healing response. However, over time, these changes become maladaptive leading to fibrosis and reduced cardiac function.

Although not present in normal myocardium, myofibroblasts are highly localized to sites of injury where synthesis and deposition of collagen promotes scar formation and fibrosis [Sun Y, Weber K T. Infarct scar: a dynamic tissue. Cardiovasc Res. 2000; 46: 250-256]. In addition, these cells are also located near, or associated with, blood vessels. Because myofibroblasts express contractile proteins, such as smooth muscle actin, they are able to provide mechanical tension to the remodeling matrix, helping to close the wound and reduce scarring [Gabbiani G. The cellular derivation and the life span of the myofibroblast. Pathol Res Pract. 1996;

192: 708-711; Brown E, Dejana E. Cell-to-cell contract and the extracellular matrix. Curr Opin Cell Biol. 2003; 15: 505-508; Gabbiani G. The myofibroblast in wound healing and fibrocontractive diseases. J Pathol. 2003; 200: 500-503]. As the scar matures, cells in the scar undergo apoptosis, leaving a scar that consists mainly of collagen and ECM proteins, but myofibroblasts are still present [Gurtner G C, Werner S, Barrandon Y, Longaker M T. Wound repair and regeneration. Nature. 2008; 453: 314-321]. Myofibroblasts have been observed in mature scars in a rat model of myocardial infarct, as well as in scarred human tissue [Sun Y, Weber K T. Infarct scar: a dynamic tissue. Cardiovasc Res. 2000; 46: 250-256; Willems I E, Havenith M G, DeMey J G, Daemen M J. The alpha-smooth muscle actin-positive cells in healing human myocardial scars. Am J Pathol. 1994; 145: 868-875]. It is not known why myofibroblasts persist, but they are highly involved in regulating cardiac remodeling, cardiac dysfunction, and ultimately cardiac failure.

In the normal heart, collagen and other ECM components help maintain heart structure and function. ECM is synthesized and degraded by cardiac fibroblasts in a coordinated fashion; however, during heart failure there is disruption of these regulatory pathways, leading to an imbalance of ECM synthesis and degradation that determines the level of cardiac remodeling. Increases in the extracellular matrix or fibrosis may be reparative, replacing areas of myocyte loss with a structural scar, or reactive, involving increases in ECM deposition at sites other than those of the primary injury. Fibroblast proliferation and differentiation to myofibroblasts in remote areas of the infarct (reactive fibrosis) can cause an increase in ECM synthesis and deposition which results in increased mechanical stiffness and contributes to relaxation abnormalities, arrhythmogenicity, progressive diastolic dysfunction and heart failure. The size of the infarcted area, the infarcted wound healing, and chronic left ventricular (LV) remodeling determine the extent of heart failure that results [Pfeffer M A, Braunwald E. Ventricular remodeling after myocardial infarction. Experimental observations and clinical implications. Circulation. 1990; 81:1161-72; Opie L H, Commerford P J, Gersh B J, Pfeffer M A. Controversies in ventricular remodelling. Lancet. 2006; 367:356-67; Dorn G W, 2nd. Novel pharmacotherapies to abrogate postinfarction ventricular remodeling. Nat Rev Cardiol. 2009; 6:283-91]. Progressive increases in fibrosis can lead to systolic dysfunction and left ventricular hypertrophy. Moreover, increased levels of collagen can disrupt electrophysiological communication between myocytes. Furthermore, perivascular fibrosis can impair myocyte oxygen supply, reduce coronary reserve, and accentuate ischemia [Brown R D, Ambler S K, Mitchell M D, Long C S. The cardiac fibroblast: therapeutic target in myocardial remodeling and failure Annu Rev Pharmacol Toxicol. 2005; 45:657-87].

Anti-fibrosis strategies are limited and are not particularly targeted. Currently, angiotensin-converting enzyme (ACE) inhibition, angiotensin receptor antagonism, and HMG-CoA-reductase inhibition are available [Opie L H, Commerford P J, Gersh B J, Pfeffer M A. Controversies in ventricular remodeling. Lancet. 2006; 367:356-67; Bauersachs J, Galuppo P, Fraccarollo D, Christ M, Ertl G. Improvement of left ventricular remodeling and function by hydroxymethylglutaryl coenzyme a reductase inhibition with cerivastatin in rats with heart failure after myocardial infarction. Circulation. 2001; 104:982-5; Shyu K G, Wang B W, Chen W J, Kuan P, Hung C R. Mechanism of the inhibitory effect of atorvastatin on endoglin expression induced by transforming growth factorbeta1 in cultured cardiac fibroblasts. Eur J Heart Fail. 2010; 12:219-26]. While these have shown some beneficial effects, more effective prevention focused at the level of the fibroblast is needed [Brown R D, Ambler S K, Mitchell M D, Long C S. The cardiac fibroblast: therapeutic target in myocardial remodeling and failure Annu Rev Pharmacol Toxicol. 2005; 45:657-87; Fraccarollo D, Galuppo P, Bauersachs J. Novel therapeutic approaches to post-infarction remodelling. Cardiovascular research. 2012; 94:293-303].

The Role of the TGFβ/p38 MAPK-MK2 Signaling Pathway in Fibrosis and Post-MI Remodeling The TGFβ/p38 pathway is central to the pathogenesis of fibrosis. MAPKAP kinase 2 (MK2) is a downstream signaling molecule in the TGFβ/p38 pathway and MK2 phosphorylates and activates signaling molecules that are important in the pathologic processes of fibrotic disease, including inflammatory signaling and fibroblast activation and migration (FIG. 13). MK2 is upstream of both fibrosis and inflammatory pathways. The fibrosis pathway leads to increases in stress fibers (α-smooth muscle actin expression) which results in the myofibroblast phenotype. Myofibroblasts accumulate at sites of tissue remodeling and produce extracellular matrix components such as collagen and hyaluronan (HA) that ultimately compromise organ function. MK2 also phosphorylates transcription factors such as hnRNPA0 which stabilizes cytokines in the inflammatory pathway.

p38 mitogen-activated protein kinase (MAPK) and its upstream and downstream signaling molecules have been shown to play an important role in the response to cellular stress from stimuli [Saklatvala, Curr Opin Pharmacol, 4:372-377, 2004; Edmunds, J. and Talanian, MAPKAP Kinase 2 (MK2) as a Target for Anti-inflammatory Drug Discovery. In Levin, J and Laufer, S (Ed.), RSC Drug Discovery Series No. 26, p 158-175, the Royal Society of Chemistry, 2012].

There are four isoforms of p38 (i.e., p38α, p38β, p38γ, and p38δ) with p38α being most clearly associated with inflammation. Cytokines and other extracellular stimuli (such as growth factors, DNA damage, and oxidative stress) signal through multiple receptors and other mechanisms to activate a cascade of kinases starting with a MAP3K (e.g., MEKK3 or TAK1), then a MAP2K (e.g., MKK3 or MKK6), and then a MAPK (such as p38α). By direct and indirect effects, including the stabilization, translocation, and translation of mRNAs, p38 plays a major role in the production of pro-inflammatory cytokines, such as TNF-α, IL-6, and IFN-γ, as well as the induction of other pro-inflammatory cytokines, such as COX-2.

Generally, in resting cells, p38 MAPK and MK2 are physically bound together in the nucleus. Cellular stress causes the phosphorylation of p38 MAPK by an upstream kinase, such as MKK3 [Kim et al., Am J Physiol Renal Physiol, 292:F1471-1478, 2007]. The activated p38 MAPK then phosphorylates MK2 at residues Thr-222, Ser-272, and/or Thr-334 [Engel et al., EMBO J, 17: 3363-3371, 1998]. The activated MK2 and p38, still physically bound together, translocate to cytoplasm, where they phosphorylate their respective target protein [Ben-Levy et al., Curr Biol, 8:1049-1057, 1998].

In turn, activated MK2 mediates phosphorylation of HSPB1 in response to stress, leading to dissociation of HSPB1 from large small heat-shock protein (sHsps) oligomers, thereby impairing their chaperone activities and ability to protect against oxidative stress effectively. MK2 is also involved in inflammatory and immune responses by regulating Tumor Necrosis Factor (TNF) and IL-6 production post-transcriptionally. This activity is mediated by phosphorylation of Adenine- and Uridine (AU)-Rich Elements (AREs)-binding proteins, such as Embryonic Lethal, Abnormal Vision, Drosophila-Like 1 (ELAVL1), Heterogeneous Nuclear Ribonucleoprotein A0 (HNRNPA0), Polyadenylate-Binding Protein 1 (PABPC1), and Tristetraprolin (TTP/ZFP36), which, in turn, regulate the stability and translation of TNF-α and IL-6 mRNAs. Phosphorylation of TTP/ZFP36, a major post-transcriptional regulator of TNF-α, promotes its binding to 14-3-3 proteins and reduces its affinity to ARE mRNA, thereby inhibits degradation of ARE-containing transcript.

In addition, MK2 also plays an important role in the late G2/M checkpoint following DNA damage through a process of post-transcriptional mRNA stabilization. Following DNA damage, MK2 re-localizes from nucleus to cytoplasm and phosphorylates Heterogeneous Nuclear Ribonucleoprotein A0 (HNRNPA0) and Poly(A)-specific Ribonuclease (PARN), leading to stabilization of growth arrest and DNA-damage-inducible protein 45A (GADD45A) mRNA. Additionally, studies have shown that MK2 is involved in the toll-like receptor signaling pathway (TLR) in dendritic cells and in acute TLR-induced macropinocytosis by phosphorylating and activating Ribosomal protein S6 kinase, 90 kDa, polypeptide 3 (RPS6KA3).

Although enzymes at each level of the aforementioned p38 MAPK signaling cascade have been explored for anti-cytokine drug discovery, it is difficult to generalize how upstream or downstream targets in such a pathway might vary in their potential for efficacy. For example, upstream targets might have multiple effects, enhancing efficacy, but might be bypassed by other signaling mechanisms, limiting the impact of inhibition. Undesirable side-effects are similarly difficult to predict. Therefore, specific properties of signaling mechanisms like that of the p38 pathway must be considered case by case to select the best targets based on empirical experience [Edmunds, J. and Talanian, MAPKAP Kinase 2 (MK2) as a Target for Anti-inflammatory Drug Discovery. In Levin, J and Laufer, S (Ed.), RSC Drug Discovery Series No. 26, p 158-175, the Royal Society of Chemistry, 2012].

Indeed, while there have been many reports of p38 inhibitors with promising properties in vitro and in animal models of disease, none have achieved clinical success [Edmunds, J. and Talanian, MAPKAP Kinase 2 (MK2) as a Target for Anti-inflammatory Drug Discovery. In Levin, J and Laufer, S (Ed.), RSC Drug Discovery Series No. 26, p 158-175, the Royal Society of Chemistry, 2012]. Many targets beyond those related to cytokine production are regulated by p38, consistent with observed pleiotropic consequences of its inhibition and suggesting multiple mechanisms of toxicity and even pro-inflammatory effects. For example, in hepatocytes, p38 directly and indirectly down-regulates JNK, thereby modulating hepatocyte sensitivity to lipopolysaccharide (LPS) and TNF-α induced cell death; this may be an important mechanism of p38 inhibition-induced liver toxicity. In addition, activation of MSK1 and MSK2 by p38 may induce expression of anti-inflammatory cytokine IL-10, and therefore inhibition of p38 may have a pro-inflammatory effect that contributes to the observed transient suppression of inflammatory markers by p38 inhibitors. Thus, there are significant concerns that, as an anti-inflammatory strategy, p38 inhibition will not result in adequate efficacy or acceptable safety.

On the other hand, MK2 attracted wide attention as a potential drug discovery target when it was reported that MK2-deficient knockout mice are viable and fertile, and are defective in TNF-α production. Splenocytes derived from these animals are defective in the production of several pro-inflammatory cytokines, including TNF-α, IL-6 and IFN-γ and the animals themselves are resistant to collagen-induced arthritis (a mouse model of rheumatoid arthritis (RA)), as well as in ovalbumin-induced airway inflammation (a mouse model of asthma). Dosed orally, inhibitors of MK2 can block acute systemic induction of TNF-α by LPS in rats and can reduce paw swelling in the rat streptococcal cell wall (SCW)-induced arthritis model. These results suggested that MK2 mediates most or all inflammatory signals of the p38 cascade while other p38 substrates regulate the pathways responsible for toxicity or attenuated efficacy; and that MK2 inhibition might deliver on the promise of p38 inhibition for anti-inflammatory efficacy while also giving a more favorable safety profile.

Myocyte death during lethal myocardial infarction, cardiac dysfunction, and fibrosis during post-MI remodeling and hypertrophy is associated with sustained activation of p38 [Clark J E, Sarafraz N, Marber M S. Potential of p38-MAPK inhibitors in the treatment of ischaemic heart disease. Pharmacol Ther. 2007; 116:192-206; Kerkela R, Force T. p38 mitogen-activated protein kinase: a future target for heart failure therapy? Journal of the American College of Cardiology. 2006; 48:556-8; Wang Y. Mitogen-activated protein kinases in heart development and diseases. Circulation. 2007; 116:1413-23]. Recent studies in MK2−/− mice have illustrated that MK2 acts downstream of p38 and is responsible for p38-induced heart failure [Streicher J M. The role of mitogen activated protein kinase activated protein kinase-2 in regulating p38 mitogen activated protein kinase induced cyclooxygenase-2 induction and heart failure: University of California-Los Angeles; 2009]. Similarly, MK2−/− mice are resistant to ischemia reperfusion injury [Shiroto K, Otani H, Yamamoto F, Huang C K, Maulik N, Das D K. MK2−/− gene knockout mouse hearts carry anti-apoptotic signal and are resistant to ischemia reperfusion injury. J Mol Cell Cardiol. 2005; 38:93-7], indicating a critical role of MK2 in ischemic heart disease experimentally. When mice lacking MK2 (MK2−/−) were compared to M2+/+ mice on a transgenic p38 background, the transgenic p38-induced heart failure in the MK2−/− mice was significantly protective [Streicher J M. The role of mitogen activated protein kinase activated protein kinase-2 in regulating p38 mitogen activated protein kinase induced cyclooxygenase-2 induction and heart failure: University of California-Los Angeles; 2009]. Similarly, MK2−/− mice are resistant to ischemia reperfusion injury [Shiroto K, Otani H, Yamamoto F, Huang C K, Maulik N, Das D K. MK2−/− gene knockout mouse hearts carry anti-apoptotic signal and are resistant to ischemia reperfusion injury. J Mol Cell Cardiol. 2005; 38:93-7], implicating a critical role of MK2 in ischemic injury. Consistent with an MK2-p38 axis mediating ischemic cardiac damage, inhibiting p38 activation protects the heart against ischemic insult and cardiac dysfunction [Marber M S, Rose B, Wang Y. The p38 mitogen-activated protein kinase pathway—a potential target for intervention in infarction, hypertrophy, and heart failure. J Mol Cell Cardiol. 2011; 51:485-90; Tanno M, Bassi R, Gorog D A, Saurin A T, Jiang J, Heads R J, et al. Diverse mechanisms of myocardial p38 mitogen-activated protein kinase activation: evidence for MKK-independent activation by a TAB1-associated mechanism contributing to injury during myocardial ischemia. Circulation Res. 2003; 93:254-61; Marais E, Genade S, Huisamen B, Strijdom J G, Moolman J A, Lochner A. Activation of p38 MAPK induced by a multi-cycle ischaemic preconditioning protocol is associated with attenuated p38 MAPK activity during sustained ischemia and reperfusion. J Mol Cell Cardiol. 2001; 33:769-78; Sanada S, Kitakaze M, Papst P J, Hatanaka K, Asanuma H, Aki T, et al. Role of phasic dynamism of p38 mitogen-activated protein kinase activation in ischemic preconditioning of the canine heart. Circulation Res. 2001; 88:175-80; Nagarkatti D S, Sha'afi R I. Role of p38 MAP kinase in myocardial stress. J Mol Cell Cardiol. 1998; 30:1651-64]. At the cellular level, ischemic activation of the MK2-p38 signalling pathway induces cardiac apoptosis [Matsumoto-Ida M, Takimoto Y, Aoyama T, Akao M, Takeda T, Kita T. Activation of TGF-beta1-TAK1-p38 MAPK pathway in spared cardiomyocytes is involved in left ventricular remodeling after myocardial infarction in rats. Am J Physiol Heart Circul Physiol. 2006; 290:H709-15], specifically in cardiomyocytes [Clark J E, Sarafraz N, Marber M S. Potential of p38-MAPK inhibitors in the treatment of ischaemic heart disease. Pharmacol Ther. 2007; 116:192-206; Kerkela R, Force T. p38 mitogen-activated protein kinase: a future target for heart failure therapy? Journal of the American College of Cardiology. 2006; 48:556-8; Wang Y. Mitogen-activated protein kinases in heart development and diseases. Circulation. 2007; 116:1413-23]. In fibroblasts, p38 regulates extracellular matrix proteins in primary cardiac fibroblasts during oxidative stress [Hsu P L, Su B C, Kuok Q Y, Mo F E. Extracellular matrix protein CCN1 regulates cardiomyocyte apoptosis in mice with stress-induced cardiac injury. Cardiovascular Res. 2013; 98:64-72].

The use of rationally designed cell-permeable peptides that inhibit Mitogen Activated Protein Kinase Activated Protein Kinase II (MK2) activity and downstream fibrosis and inflammation is unique. Recent studies have reported that the cell-permeable peptide MMI-0100 inhibits inflammation and fibrosis in intimal hyperplasia in a mouse vein graft model [Muto A, Panitch A, Kim N, Park K, Komalavilas P, Brophy C M, et al Inhibition of Mitogen Activated Protein Kinase Activated Protein Kinase II with MMI-0100 reduces intimal hyperplasia ex vivo and in vivo. Vascular Pharmacol. 2012; 56:47-55], bleomycin-induced pulmonary fibrosis [Vittal R, Fisher A, Gu H, Mickler E A, Panitch A, Lander C, et al. Peptide-mediated Inhibition of MK2 Ameliorates Bleomycin-Induced Pulmonary Fibrosis. Am J Respir Cell Mol Biol. 2013] and in inhibiting abdominal adhesions post-surgery [Ward B C, Kavalukas S, Brugnano J, Barbul A, Panitch A. Peptide inhibitors of MK2 show promise for inhibition of abdominal adhesions. J Surg Res 2011; 169:e27-36]. These peptides target the substrate-binding site of MK2 and contain permeant domains that are rapidly taken up by macropinocytosis and targeted to endosomal compartments, where they are retained for up to 7 days [Flynn C R, Cheung-Flynn J, Smoke C C, Lowry D, Roberson R, Sheller M R, et al. Internalization and intracellular trafficking of a PTD-conjugated anti-fibrotic peptide, AZX100, in human dermal keloid fibroblasts. J Pharm Sci. 2010; 99:3100-21].

To minimize the extent of heart failure after a large or recurrent MI, therapeutic strategies are needed to limit infarct wound healing. The described invention offers approaches to minimize the extent of heart failure or recurrent MI by utilizing a cell-penetrating, peptide-based inhibitor of MK2.

SUMMARY OF THE INVENTION

According to one aspect, the described invention provides a method for reducing left ventricular remodeling resulting from a myocardial infarction (MI) in a subject in need of such treatment, the method comprising administering to the subject a therapeutic amount of a pharmaceutical composition comprising a polypeptide of amino sequence YARAAARQARAKALARQLGVAA (SEQ ID NO: 1) or a functional equivalent thereof made from a fusion between a first polypeptide that is a cell permeable protein (CPP) selected from the group consisting of a polypeptide of amino acid sequence YARAAARQARA (SEQ ID NO: 2), WLRRIKAWLRRIKA (SEQ ID NO: 21), WLRRIKA (SEQ ID NO: 22), YGRKKRRQRRR (SEQ ID NO: 23), FAKLAARLYR (SEQ ID NO: 25), and KAFAKLAARLYR (SEQ ID NO: 26), and a second polypeptide that is a therapeutic domain (TD), and a pharmaceutically acceptable carrier, the ventricular remodeling being characterized by aberrant deposition of an extracellular matrix protein, an aberrant promotion of fibroblast proliferation in the heart, an aberrant induction of myofibroblast differentiation, an aberrant promotion of attachment of myofibroblasts to an extracellular matrix or a combination thereof; wherein the therapeutic amount is effective (i) to inhibit MK2; (ii) to reduce cardiac fibrosis; (iii) to preserve cardiac muscle; and (iv) to preserve systolic function, wherein the method is effective to protect cardiomyocytes from an ischemic insult, reduce regions of fibrosis at a site of ischemic insult, or a combination thereof, wherein without the therapeutic amount, the ventricular remodeling can progress to heart failure.

According to another aspect, the described invention provides a method for preserving cardiac function after a myocardial infarction (MI) in a subject in need thereof, the method comprising administering to the subject in need thereof a therapeutic amount of a pharmaceutical composition comprising a polypeptide of amino sequence YARAAARQARAKALARQLGVAA (SEQ ID NO: 1) or a functional equivalent thereof made from a fusion between a first polypeptide that is a cell permeable protein (CPP) selected from the group consisting of a polypeptide of amino acid sequence YARAAARQARA (SEQ ID NO: 2), WLRRIKAWLRRIKA (SEQ ID NO: 21), WLRRIKA (SEQ ID NO: 22), YGRKKRRQRRR (SEQ ID NO: 23), FAKLAARLYR (SEQ ID NO: 25), and KAFAKLAARLYR (SEQ ID NO: 26), and a second polypeptide that is a therapeutic domain (TD), and a pharmaceutically acceptable carrier, wherein the therapeutic amount is effective (i) to inhibit MK2; (ii) to increase ejection fraction; (iii) to increase fractional shortening; and (iv) to decrease left ventricular dilation, wherein the method is effective to protect cardiomyocytes from an ischemic insult, reduce regions of fibrosis at a site of ischemic insult, or a combination thereof.

According to one embodiment, the therapeutic domain (TD) is selected from the group consisting of a polypeptide of amino acid sequence KALARQLGVAA (SEQ ID NO: 3), KALARQLAVA (SEQ ID NO: 9), KALARQLGVA (SEQ ID NO: 10), KALARQLGVAA (SEQ ID NO: 11), KALNRQLGVAA (SEQ ID NO: 12), KAANRQLGVAA (SEQ ID NO: 13), KALNAQLGVAA (SEQ ID NO: 14), KALNRALGVAA (SEQ ID NO: 15), KALNRQAGVAA (SEQ ID NO: 16), KALNRQLAVA (SEQ ID NO: 17), KALNRQLAVAA (SEQ ID NO: 18), KALNRQLGAAA (SEQ ID NO: 19), and KALNRQLGVA (SEQ ID NO: 20).

According to one embodiment, the cardiac fibrosis is reduced by 50% compared to an untreated control subject.

According to one embodiment the therapeutic amount is effective to inhibit apoptotic cell death of cardiomyocytes in a peri-infarct zone. According to one such embodiment, the therapeutic amount is effective to inhibit apoptotic cell death of cardiomyocytes, enhance apoptotic cell death of cardiac fibroblasts, or a combination thereof.

According to one embodiment, the therapeutic amount is effective to inhibit caspase activity. According to another embodiment, the caspase activity is caspase 3/7 activity.

According to one embodiment, the therapeutic amount is effective to enhance lactate dehydrogenase (LDH) release.

According to one embodiment, the therapeutic amount is effective to inhibit heterogeneous nuclear ribonucleoprotein A0 (HNRNPA0) protein expression.

According to another aspect, the described invention provides a kit comprising: (a) a composition comprising at least one MK2 inhibitor peptide; (b) a means for administering the composition; and (c) a packaging material.

According to one embodiment, the MK2 inhibitor peptide is a polypeptide of amino sequence YARAAARQARAKA-LARQLGVAA (SEQ ID NO: 1).

According to one embodiment, the composition further comprises a pharmaceutically acceptable excipient.

According to one embodiment, the packaging material is an instruction.

According to one embodiment, the means for administering the composition comprises a syringe. According to another embodiment, the means for administering the composition comprises an inhalation device.

BRIEF DESCRIPTION OF THE DRAWINGS

FIG. 1A-D show an experimental design for treatment of acute myocardial infarction (AMI) with 50 μg/kg/day MMI-0100 peptide or PBS administered intra-peritoneally 30 minutes after insults with survival analysis. FIG. 1A. Echocardiography schedule in relation to acute myocardial infarction (AMI) and thoracotomy and sham ligation surgical intervention. FIG. 1B. Daily drug delivery schedule of MMI-0100 peptide or PBS control. FIG. 1C. Conscious echocardiographic analysis of AMI (thoracotomy and permanent LAD coronary artery ligation), thoracotomy and sham ligation (threaded, but not tied, removed), and AMI followed by MMI-0100 peptide administered intra-peritoneally in PBS vehicle, started 30 minutes after permanent LAD ligation placed. FIG. 1D. Representative M-mode tracing from three experimental groups at baseline, 1 week, and 2 weeks after AMI surgical intervention. A Kruskal-Wallis Oneway ANOVA was performed at each terminal time point in experiments performed in parallel. If significance was reached ($p<0.05$), a post-hoc all pairwise Multiple Comparison Procedures (Tukey Test) was performed between each of the groups to determine significance. *$p<0.05$ vs. thoracotomy and sham ligation (control); **$p<0.05$ vs. other two groups.

FIG. 2A-E shows permanent LAD coronary artery ligation (surgical induction of acute MI) treated daily with 50 μg/kg/day MMI-0100 peptide (first given 30 minutes post-AMI) in vivo results in a significant reduction in fibrosis at day 14. FIG. 2A. The area of fibrosis was analyzed in 3-4 blindly chosen hearts each heart at 14-15 levels, 3 sections at each level, and blinded fibrosis analysis of trichrome stained histological sections using Aperio (42 sections analyzed per mouse heart). FIG. 2B. Histological analysis of fibrosis (collagen staining blue by Aperio algorithm analysis) of 3-4 hearts per group resulting from acute myocardial infarction at 14 days post-AMI. FIG. 2C. Representative trichrome stained sections from mouse hearts challenged with permanent AMI (~21% of the area stains blue, including primarily interstitial fibrosis). FIG. 2D. Representative trichrome-stained sections from mouse hearts challenged with permanent AMI treated daily with 50 μg/kg/day MMI-0100 peptide starting 30 minutes post-infarction (~11% of the area stains blue, including primarily interstitial fibrosis). FIG. 2E. Representative trichrome-stained sections from mouse control hearts, including the thoracotomy+ sham ligation, no surgery+no drug, and no surgery+50 μg/kg/day MMI-0100 peptide. (0.9% of the area stains blue, representing connective tissue and vessels; no interstitial fibrosis evident in any analyzed section). A Kruskal-Wallis One-way ANOVA was performed on the fibrosis % from serial sections using 3-4 hearts per group; each single fibrosis per heart was the weighted mean of 126-180 sections described in FIG. 2A. above. If significance was reached ($p<0.05$), a post-hoc all pairwise Multiple Comparison Procedures (Tukey Test) was performed between each of the groups to determine significance. *$p<0.05$ vs. all other groups.

FIGS. 3A-C show that MMI-0100 peptide reduces caspase 3/7 activation in H9C2 cardiomyocytes challenged with 1% hypoxia. FIG. 3A. H9C2 cells were challenged with 1% hypoxia for 8, 16, and 24 hours; the media were collected for LDH release and cells immediately harvested for caspase 3/7 activity and Western blot analysis at each time point. Each bar represents 3 wells performed in triplicate in experimental conditions repeated on at least 2 independent occasions. FIG. 3B. Caspase 3/7 activity of harvested cells at 8, 16, and 24 hours in the presence or absence of MMI-0100 peptide; 0 μM (vehicle only, 0.1% DMSO final), 20 μM, or 100 μM MMI-0100 peptide. FIG. 3C. LDH detection in media from the same experimental conditions as the caspase activity described above. A Kruskal-Wallis One-way ANOVA was performed at each terminal time point in experiments run in parallel. If significance was reached ($p<0.05$), a post-hoc all pairwise Multiple Comparison Procedures (Tukey Test) was performed between each of the groups to determine significance. *$p<0.05$ vs. 0 μM group (DMSO vehicle control); **$p<0.05$ vs. other two groups.

FIGS. 4A-B show that MMI-0100 peptide reduces MK2 activity in H9C2 cardiomyocytes challenged with 1% hypoxia as measured by downstream HNRNPA0 protein expressed, but does not reduce phospho- or total MK2 levels. FIG. 4A. H9C2 cells were challenged with 1% hypoxia for 8, 16, and 24 hours; desitometric analysis of Western immunoblot (right, representative 1 of 3 replicates per bar) demonstrated significant decreases in HNRNPA0 protein expression. FIG. 4B. Densitometric analysis phospho- and total MK2 levels (below). A Kruskal-Wallis One-way ANOVA was performed at each terminal time point in experiments run in parallel. If significance was reached ($p<0.05$), a post-hoc all pairwise Multiple Comparison Procedures (Tukey Test) was performed between each of the groups to determine significance. **$p<0.05$ vs. other 2 groups.

FIGS. 5A-C show that MMI-0100 peptide reduces caspase 3/7 activation in HL1 cardiomyocytes challenged with 1% hypoxia. FIG. 5A. HL1 cells were challenged with 1% hypoxia for 4, 8, and 12 hours; the media were collected for LDH release and cells immediately harvested for caspase 3/7 activity and Western blot analysis at each time point. Each bar represents 3 wells performed in triplicate in experimental conditions repeated on at least 2 independent occasions. FIG. 5B. Caspase 3/7 activity of harvested cells at 4, 8, and 12 hours in the presence or absence of MMI-0100 peptide; 0 μM (vehicle only, 0.1% DMSO final), 20 μM and 100 μM MMI-0100 peptide. FIG. 5C. LDH detection in media from the same experimental conditions as the caspase activity described above. A Kruskal-Wallis Oneway ANOVA was performed at each terminal time point in experiments run in parallel. If significance was reached ($p<0.05$), a post-hoc all pairwise Multiple Comparison Procedures (Tukey Test) was performed between each of the groups to determine significance. *p<0.05 vs. 0 µM group (DMSO vehicle control); p<0.05 vs. other two groups; * p<0.05 vs. 20 µM MMI-0100 peptide group.

FIG. 6A. H9C2 cells were challenged with 1% hypoxia for 4, 8, and 12 hours; desitometric analysis of Western immunoblot (right, representative 1 of 3 replicates per bar) demonstrated significant decreases in HNRNPA0 protein expression. FIG. 6B. Densitometric analysis phospho- and total MK2 levels (below). A Kruskal-Wallis One-way ANOVA was performed at each terminal time point in experiments run in parallel. If significance was reached (p<0.05), a post-hoc all pairwise Multiple Comparison Procedures (Tukey Test) was performed between each of the groups to determine significance. *p<0.05 vs. 0 µM group (DMSO vehicle control).

FIGS. 7A-C show that MMI-0100 peptide enhances caspase 3/7 activation and LDH release in primary cardiac fibrolasts challenged with 1% hypoxia. FIG. 7A. Primary cardiac fibroblasts were challenged with 1% hypoxia for 16, 32, and 48 hours; the media was collected for LDH release and cells immediately harvested for caspase 3/7 activity and Western blot analysis at each time point. Each bar represents 3 wells performed in triplicate in experimental conditions repeated on at least 2 independent occasions. FIG. 7B. Caspase 3/7 activity of harvested cells at 16, 32, and 48 hours in the presence or absence of MMI-0100 peptide; 0 µM (vehicle only, 0.1% DMSO final), 20 µM, or 100 µM MMI-0100 peptide. FIG. 7C. LDH detection in media from the same experimental conditions as the caspase activity described above. A Kruskal-Wallis One-way ANOVA was performed at each terminal time point in experiments run in parallel. If significance was reached (p<0.05), a post-hoc all pairwise Multiple Comparison Procedures (Tukey Test) was performed between each of the groups to determine significance. *p<0.05 vs. 0 µM group (DMSO vehicle control); p<0.05 vs. other two groups; * p<0.05 vs. 20 µM MMI-0100 peptide group.

FIG. 8A. Primary cardiac fibroblasts were challenged with 1% hypoxia for 16, 32, and 48 hours; desitometric analysis of Western immunoblot (right, representative 1 of 3 replicates per bar) no significant changes in HNRNPA0 protein expression were detected. FIG. 8B. Densitometric analysis phospho- and total MK2 levels (below). A Kruskal-Wallis Oneway ANOVA was performed at each terminal time point in experiments run in parallel. n.s.=not significant.

FIG. 9A. Kaplan-Meier survival curve post-surgery of acute MI and acute MI+MMI-0100 peptide. FIG. 9B. Kaplan-Meier survival curve after daily MMI-0100 peptide or PBS (vehicle only) treatment. A Log-rank (Mantel-Cox) test was performed to test differences in survival (Chi square 0.9211, df=1, p=0.3372).

FIGS. 10A-F show histological analysis of hearts from mice challenged with AMI and treated with PBS or 50 µg/kg/day MMI-0100 peptide (PBS vehicle) which reveals sparing of cells within the fibrotic scarring of the anterior wall. FIG. 10A-C: Representative sections reveal few cells remain in the fibrotic scar of the anterior wall of AMI hearts. FIG. 10D-F: Representative sections reveal variable periodic islands of cells in the anterior wall scar. Magnification 4-8×, with scale on each individual panel.

DETAILED DESCRIPTION OF THE INVENTION

Figure 1B:
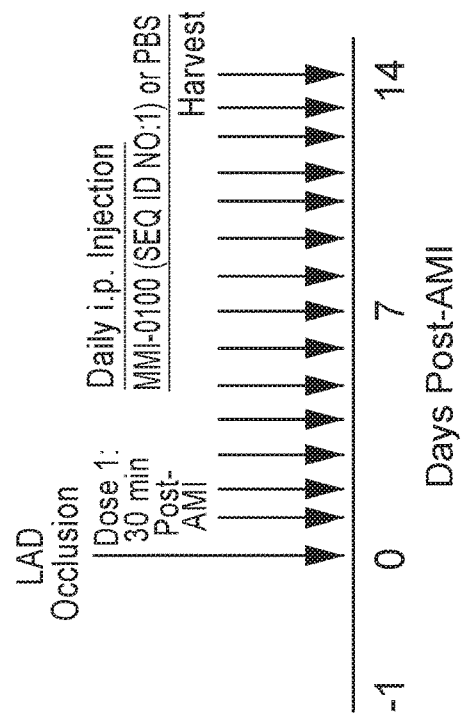

The described invention can be better understood from the following description of exemplary embodiments, taken in conjunction with the accompanying figures and drawings. It should be apparent to those skilled in the art that the described embodiments provided herein are merely exemplary and illustrative and not limiting.

Definitions

Various terms used throughout this specification shall have the definitions set out herein.

The term "administering" as used herein includes in vivo administration, as well as administration directly to tissue ex vivo. Generally, compositions can be administered systemically either orally, buccally, parenterally, topically, by inhalation or insufflation (i.e., through the mouth or through the nose), or rectally in dosage unit formulations containing conventional nontoxic pharmaceutically acceptable carriers, adjuvants, and vehicles as desired, or can be locally administered by means such as, but not limited to, injection, implantation, grafting, topical application, or parenterally.

The terms "apoptosis" or "programmed cell death" refer to a highly regulated and active process that contributes to biologic homeostasis comprised of a series of biochemical events that lead to a variety of morphological changes, including blebbing, changes to the cell membrane, such as loss of membrane asymmetry and attachment, cell shrinkage, nuclear fragmentation, chromatin condensation, and chromosomal DNA fragmentation, without damaging the organism.

Apoptotic Pathways

Apoptotic cell death is induced by many different factors and involves numerous signaling pathways, some dependent on caspase proteases (a class of cysteine proteases) and others that are caspase independent. It can be triggered by many different cellular stimuli, including cell surface receptors, mitochondrial response to stress, and cytotoxic T cells, resulting in activation of apoptotic signaling pathways.

The caspases involved in apoptosis convey the apoptotic signal in a proteolytic cascade, with caspases cleaving and activating other caspases that then degrade other cellular targets that lead to cell death. The caspases at the upper end of the cascade include caspase-8 and caspase-9. Caspase-8 is the initial caspase involved in response to receptors with a death domain (DD) like Fas.

Receptors in the TNF receptor family are associated with the induction of apoptosis, as well as inflammatory signaling. The Fas receptor (CD95) mediates apoptotic signaling by Fas-ligand expressed on the surface of other cells. The Fas-FasL interaction plays an important role in the immune system and lack of this system leads to autoimmunity, indicating that Fas-mediated apoptosis removes self-reactive lymphocytes. Fas signaling also is involved in immune surveillance to remove transformed cells and virus infected cells. Binding of Fas to oligimerized FasL on another cell activates apoptotic signaling through a cytoplasmic domain termed the death domain (DD) that interacts with signaling adaptors including FAF, FADD and DAX to activate the caspase proteolytic cascade. Caspase-8 and caspase-10 first are activated to then cleave and activate downstream caspases and a variety of cellular substrates that lead to cell death.

Mitochondria participate in apoptotic signaling pathways through the release of mitochondrial proteins into the cytoplasm. Cytochrome c, a key protein in electron transport, is released from mitochondria in response to apoptotic signals, and activates Apaf-1, a protease released from mitochondria. Activated Apaf-1 activates caspase-9 and the rest of the caspase pathway. Smac/DIABLO is released from mitochondria and inhibits IAP proteins that normally interact with caspase-9 to inhibit apoptosis. Apoptosis regulation by Bcl-2 family proteins occurs as family members form complexes that enter the mitochondrial membrane, regulating the release of cytochrome c and other proteins. TNF family receptors that cause apoptosis directly activate the caspase cascade, but can also activate Bid, a Bcl-2 family member, which activates mitochondria-mediated apoptosis. Bax, another Bcl-2 family member, is activated by this pathway to localize to the mitochondrial membrane and increase its permeability, releasing cytochrome c and other mitochondrial proteins. Bcl-2 and Bcl-xL prevent pore formation, blocking apoptosis. Like cytochrome c, AIF (apoptosis-inducing factor) is a protein found in mitochondria that is released from mitochondria by apoptotic stimuli. While cytochrome C is linked to caspase-dependent apoptotic signaling, AIF release stimulates caspase-independent apoptosis, moving into the nucleus where it binds DNA. DNA binding by AIF stimulates chromatin condensation, and DNA fragmentation, perhaps through recruitment of nucleases.

The mitochondrial stress pathway begins with the release of cytochrome c from mitochondria, which then interacts with Apaf-1, causing self-cleavage and activation of caspase-9. Caspase-3, -6 and -7 are downstream caspases that are activated by the upstream proteases and act themselves to cleave cellular targets.

Granzyme B and perforin proteins released by cytotoxic T cells induce apoptosis in target cells, forming transmembrane pores, and triggering apoptosis, perhaps through cleavage of caspases, although caspase-independent mechanisms of Granzyme B mediated apoptosis have been suggested.

Fragmentation of the nuclear genome by multiple nucleases activated by apoptotic signaling pathways to create a nucleosomal ladder is a cellular response characteristic of apoptosis. One nuclease involved in apoptosis is DNA fragmentation factor (DFF), a caspase-activated DNAse (CAD). DFF/CAD is activated through cleavage of its associated inhibitor ICAD by caspases proteases during apoptosis. DFF/CAD interacts with chromatin components such as topoisomerase II and histone H1 to condense chromatin structure and perhaps recruit CAD to chromatin. Another apoptosis activated protease is endonuclease G (EndoG). EndoG is encoded in the nuclear genome but is localized to mitochondria in normal cells. EndoG may play a role in the replication of the mitochondrial genome, as well as in apoptosis. Apoptotic signaling causes the release of EndoG from mitochondria. The EndoG and DFF/CAD pathways are independent since the EndoG pathway still occurs in cells lacking DFF.

Hypoxia, as well as hypoxia followed by reoxygenation, can trigger cytochrome c release and apoptosis. Glycogen synthase kinase (GSK-3) a serine-threonine kinase ubiquitously expressed in most cell types, appears to mediate or potentiate apoptosis due to many stimuli that activate the mitochondrial cell death pathway. Loberg, R D, et al., J. Biol. Chem. 277 (44): 41667-673 (2002). It has been demonstrated to induce caspase 3 activation and to activate the proapoptotic tumor suppressor gene p53. It also has been suggested that GSK-3 promotes activation and translocation of the proapoptotic Bcl-2 family member, Bax, which, upon agregation and mitochondrial localization, induces cytochrome c release.

The term "attenuate" as used herein means to reduce the force, effect, or value of.

The terms "cardiac dilation" or "cardiac dilatation" are used interchangeably herein to refer to a condition where the size of the heart cavity becomes enlarged and stretched, thinning out the heart muscle (myocardium).

The term "chemokine" as used herein refers to a class of chemotactic cytokines that signal leukocytes to move in a specific direction. The terms "chemotaxis" or "chemotactic" refer to the directed motion of a motile cell or part along a chemical concentration gradient towards environmental conditions it deems attractive and/or away from surroundings it finds repellent.

The term "condition", as used herein, refers to a variety of health states and is meant to include disorders or diseases caused by any underlying mechanism or injury.

The term "cytokine" as used herein refers to small soluble protein substances secreted by cells, which have a variety of effects on other cells. Cytokines mediate many important physiological functions, including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins including interleukin 2 (IL-2), as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines The term "disease" or "disorder," as used herein, refers to an impairment of health or a condition of abnormal functioning.

The term "drug" as used herein refers to a therapeutic agent or any substance used in the prevention, diagnosis, alleviation, treatment, or cure of disease.

The term "echocardiography" as used herein refers to the use of ultrasound in the investigation of the heart and great vessels and diagnosis of cardiovascular lesions. The term "echocardiogram as used herein refers to the record obtained by echocardiography.

The term "ejection fraction" or "EF" as used herein refers to the amount of blood the left ventricle pumps out with each contraction. The ejection fraction is an important measurement in diagnosing and tracking heart failure. For example, a normal heart's ejection fraction may be equal to or greater than 55, whereas an EF measurement less than 40 may be evidence of heart failure or cardiomyopathy. An EF between 40 and 55 is indicative of damage, for example, from a previous heart attack. EF values between 45 and 54 are characterized as mildly abnormal; EF values between 30 and 44 are characterized as moderately abnormal; and EF values less than 30 are characterized as severely abnormal.

The term "end diastolic diameter" or "left ventricular diastolic diameter" are used interchangeably herein to refer to the dimension of the left ventricle during the period in which the ventricles are relaxing (i.e., diastole). Normal left ventricular diastolic diameter values range, for example, from 3.9-5.3 for women and 4.2-5.9 for men.

The term "enhance" as used herein in its various grammatical forms refers to an increase or to intensify in quality or quantity, or to make better or augment.

The term "enzymatic activity" as used herein refers to the action of an enzyme (meaning a protein that catalyzes a specific chemical reaction) on its target. It is quantified as the amount of substrate consumed (or product formed) in a given time under given conditions. The term "turnover number" as used herein refers to the number of molecules of substrate that can be converted into product per catalytic site of a given enzyme.

The term "fractional shortening" as used herein refers to a measure of the pump function of the heart. It is the ratio between the diameter of the left ventricle when it is relaxed and its diameter when it has contracted. A normal value for fractional shortening is greater than 26%.

The terms "functional equivalent" or "functionally equivalent" are used interchangeably herein to refer to substances, molecules, polynucleotides, proteins, peptides, or polypeptides having similar or identical effects or use. A polypeptide functionally equivalent to polypeptide YARAAARQARAKALARQLGVAA (SEQ ID NO: 1), for example, may have a biologic activity, e.g., an inhibitory activity, kinetic parameters, salt inhibition, a cofactor-dependent activity, and/or a functional unit size that is substantially similar or identical to the expressed polypeptide of SEQ ID NO: 1.

Examples of polypeptides functionally equivalent to YARAAARQARAKALARQLGVAA (SEQ ID NO: 1) include, but are not limited to, a polypeptide of amino acid sequence FAKLAARLYRKALARQLGVAA (SEQ ID NO: 4), a polypeptide of amino acid sequence KAFAKLAAR-LYRKALARQLGVAA (SEQ ID NO: 5), a polypeptide of amino acid sequence YARAAARQARAKALARQLAVA (SEQ ID NO: 6), a polypeptide of amino acid sequence YARAAARQARAKALARQLGVA (SEQ ID NO: 7), and a polypeptide of amino acid sequence HRRIKAWLKKIKA-LARQLGVAA (SEQ ID NO: 8).

The MMI-0100 (YARAAARQARAKALARQLGVAA; SEQ ID NO: 1) peptide of amino acid sequence YARAAARQARAKALARQLGVAA (SEQ ID NO: 1) described in the present invention comprises a fusion protein in which a cell penetrating peptide (CPP; YARAAAR-QARA; SEQ ID NO: 2) is operatively linked to a therapeutic domain (TD; KALARQLGVAA; SEQ ID NO: 3) in order to enhance therapeutic efficacy.

Examples of polypeptides functionally equivalent to the therapeutic domain (TD; KALARQLGVAA; SEQ ID NO: 3) of the polypeptide YARAAARQARAKALARQLGVAA (SEQ ID NO: 1) include, but are not limited to, a polypeptide of amino acid sequence KALARQLAVA (SEQ ID NO: 9), a polypeptide of amino acid sequence KALARQLGVA (SEQ ID NO: 10), a polypeptide of amino acid sequence KALARQLGVAA (SEQ ID NO: 11), a polypeptide of amino acid sequence KALNRQLGVAA (SEQ ID NO: 12), a polypeptide of amino acid sequence KAANRQLGVAA (SEQ ID NO: 13), a polypeptide of amino acid sequence KALNAQLGVAA (SEQ ID NO: 14), a polypeptide of amino acid sequence KALNRALGVAA (SEQ ID NO: 15), a polypeptide of amino acid sequence KALNRQAGVAA (SEQ ID NO: 16), a polypeptide of amino acid sequence KALNRQLAVA (SEQ ID NO: 17), a polypeptide of amino acid sequence KALNRQLAVAA (SEQ ID NO: 18), a polypeptide of amino acid sequence KALNRQLGAAA (SEQ ID NO: 19), and a polypeptide of amino acid sequence KAL-NRQLGVA (SEQ ID NO: 20).

Examples of polypeptides functionally equivalent to the cell penetrating peptide (CPP; YARAAARQARA; SEQ ID NO: 2) of the polypeptide YARAAARQARAKALARQL-GVAA (SEQ ID NO: 1) include, but are not limited to, a polypeptide of amino acid sequence WLRRIKAWLRRIKA (SEQ ID NO: 21), a polypeptide of amino acid sequence WLRRIKA (SEQ ID NO: 22), a polypeptide of amino acid sequence YGRKKRRQRRR (SEQ ID NO: 23), a polypeptide of amino acid sequence WLRRIKAWLRRI (SEQ ID NO: 24), a polypeptide of amino acid sequence FAKLAAR-LYR (SEQ ID NO: 25), a polypeptide of amino acid sequence KAFAKLAARLYR (SEQ ID NO: 26), and a polypeptide of amino acid sequence HRRIKAWLKKI (SEQ ID NO: 27).

The term "heterogeneous nuclear ribonucleoprotein A0" or "HNRNPA0" as used herein refers to a gene and the protein encoded therefrom that belongs to the A/B subfamily of ubiquitously expressed heterogeneous nuclear ribonucleoproteins (hnRNPs), which are RNA binding proteins that complex with heterogeneous nuclear RNA (hnRNA). HNRNPA0 protein is associated with pre-mRNAs in the nucleus and appear to influence pre-mRNA processing and other aspects of mRNA metabolism and transport. The HNRNPA0 protein encoded by the HNRNPA0 gene has two repeats of quasi-RRM domains that bind RNAs, followed by a glycine-rich C-terminus.

The term "hypoxia" as used herein refers to a deficiency of oxygen reaching the tissues of the body; i.e., a condition in which tissues are starved of oxygen. Hypoxia can lead, for example, to necrosis (cell/tissue death).

The term "immunomodulatory cell(s)" as used herein refer(s) to cell(s) that are capable of augmenting or diminishing immune responses by expressing chemokines, cytokines and other mediators of immune responses.

The term "inflammatory cytokines" or "inflammatory mediators" as used herein refers to the molecular mediators of the inflammatory process, which may modulate being either pro- or anti-inflamatory in their effect. These soluble, diffusible molecules act both locally at the site of tissue damage and infection and at more distant sites. Some inflammatory mediators are activated by the inflammatory process, while others are synthesized and/or released from cellular sources in response to acute inflammation or by other soluble inflammatory mediators. Examples of inflammatory mediators of the inflammatory response include, but are not limited to, plasma proteases, complement, kinins, clotting and fibrinolytic proteins, lipid mediators, prostaglandins, leukotrienes, platelet-activating factor (PAF), peptides and amines, including, but not limited to, histamine, serotonin, and neuropeptides, pro-inflammatory cytokines, including, but not limited to, interleukin-1-beta (IL-1β), interleukin-4 (IL-4), interleukin-6 (IL-6), interleukin-8 (IL-8), tumor necrosis factor-alpha (TNF-α), interferon-gamma (IF-γ), and interleukin-12 (IL-12).

The term "inhibit" and its various grammatical forms, including, but not limited to, "inhibiting" or "inhibition", are used herein to refer to reducing the amount or rate of a process, to stopping the process entirely, or to decreasing, limiting, or blocking the action or function thereof. Inhibition can include a reduction or decrease of the amount, rate, action function, or process of a substance by at least 5%, at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, at least 90%, at least 95%, at least 98%, or at least 99%.

The term "inhibitor" as used herein refers to a second molecule that binds to a first molecule thereby decreasing the first molecule's activity. Enzyme inhibitors are molecules that bind to enzymes thereby decreasing enzyme activity. The binding of an inhibitor can stop a substrate from entering the active site of the enzyme and/or hinder the enzyme from catalyzing its reaction. Inhibitor binding is either reversible or irreversible. Irreversible inhibitors usually react with the enzyme and change it chemically, for example, by modifying key amino acid residues needed for enzymatic activity. In contrast, reversible inhibitors bind non-covalently and produce different types of inhibition depending on whether these inhibitors bind the enzyme, the enzyme-substrate complex, or both. Enzyme inhibitors often are evaluated by their specificity and potency.

The term "injury," as used herein, refers to damage or harm to a structure or function of the body caused by an outside agent or force, which can be physical or chemical.

The term "interleukin (IL)" as used herein refers to a cytokine secreted by, and acting on, leukocytes. Interleukins regulate cell growth, differentiation, and motility, and stimulates immune responses, such as inflammation. Examples of interleukins include interleukin-1 (IL-1), interleukin 2 (IL-2), interleukin-1α (IL-1α), interleukin-1β (IL-1β), interleukin-6 (IL-6), interleukin-8 (IL-8), interleukin-10 (IL-10) and interleukin-12 (IL-12).

The term "interleukin-1" or "IL-1" as used herein refers to a cytokine derived primarily form mononuclear phagocytes, which enhances the proliferation of T helper cells and growth and differentiation of B cells. When secreted in large quantities, IL-1 is a mediator of inflammation, entering the bloodstream and causing fever, inducing synthesis of acute phase proteins (including, but not limited to, ceruloplasmin, complement factor-3, haptoglobin, α-globulins, lipopolysaccharide binding protein, and the like) and initiating metabolic wasting. There are two distinct forms of interleukin-1, alpha (IL-1α) and beta (IL-1β), both of which perform the same functions, but represent different proteins.

The term "interleukin-6 or "IL-6" as used herein refers to a cytokine derived from macrophages and endothelial cells that increases synthesis and secretion of immunoglobulins by B lymphocytes. IL-6 also induces acute phase proteins (including, but not limited to, ceruloplasmin, complement factor-3, haptoglobin, α-globulins, lipopolysaccharide binding protein, and the like). In hepatocytes, IL-6 induces acute-phase reactants (including, but not limited to, erythrocyte sedimentation rate (ESR), C-reactive protein (CRP), fibrinogen, ferritin, and the like).

The term "interleukin-10" or "IL-10" as used herein refers to a cytokine derived from helper T cell lymphocytes ($TH_2$) that inhibits gamma-interferon (IFN-γ) and IL-2 secretion by T cell lymphocytes ($TH_1$) and inhibits mononuclear cell inflammation.

The term "kinase" as used herein refers to a type of enzyme that transfers phosphate groups from high-energy donor molecules to specific target molecules or substrates. High-energy donor groups can include, but are not limited, to GTP and ATP.

The term "left ventricular volume" are used herein to refers to the volume of blood in the left ventricle of the heart. The term "left ventricular diastolic volume" as used herein refers to the volume of blood in the left ventricle during the period in which the ventricles are relaxing. Normal values range from 56-104 mL for women and 67-155 mL for men. The term "left ventricular systolic volume" as used herein refers to the volume of blood in the left ventricle during the period in which the ventricles are contracting. Normal values range from 19-49 mL for women and 22-58 mL for men.

The term "lymphocyte" refers to a small white blood cell formed in lymphatic tissue throughout the body and in normal adults making up about 22-28% of the total number of leukocytes in the circulating blood that plays a large role in defending the body against disease. Individual lymphocytes are specialized in that they are committed to respond to a limited set of structurally related antigens. This commitment, which exists before the first contact of the immune system with a given antigen, is expressed by the presence on the lymphocyte's surface membrane of receptors specific for determinants (epitopes) on the antigen. Each lymphocyte possesses a population of receptors, all of which have identical combining sites. One set, or clone, of lymphocytes differs from another clone in the structure of the combining region of its receptors and thus differs in the epitopes that it can recognize. Lymphocytes differ from each other not only in the specificity of their receptors, but also in their functions.

Two broad classes of lymphocytes are recognized: the B-lymphocytes (B-cells), which are precursors of antibody-secreting cells, and T-lymphocytes (T-cells).

B-Lymphocytes

B-lymphocytes are derived from hematopoietic cells of the bone marrow. A mature B-cell can be activated with an antigen that expresses epitopes that are recognized by its cell surface. The activation process may be direct, dependent on cross-linkage of membrane Ig molecules by the antigen (cross-linkage-dependent B-cell activation), or indirect, via interaction with a helper T-cell, in a process referred to as cognate help. In many physiological situations, receptor cross-linkage stimuli and cognate help synergize to yield more vigorous B-cell responses. (Paul, W. E., "Chapter 1: The immune system: an introduction," Fundamental Immunology, $4^{th}$ Edition, Ed. Paul, W. E., Lippicott-Raven Publishers, Philadelphia (1999)).

Cross-linkage dependent B-cell activation requires that the antigen express multiple copies of the epitope complementary to the binding site of the cell surface receptors because each B-cell expresses Ig molecules with identical variable regions. Such a requirement is fulfilled by other antigens with repetitive epitopes, such as capsular polysaccharides of microorganisms or viral envelope proteins. Cross-linkage-dependent B-cell activation is a major protective immune response mounted against these microbes. (Paul, W. E., "Chapter 1: The immune system: an introduction," Fundamental Immunology, 4th Edition, Ed. Paul, W. E., Lippicott-Raven Publishers, Philadelphia (1999)).

Cognate help allows B-cells to mount responses against antigens that cannot cross-link receptors and, at the same time, provides costimulatory signals that rescue B cells from inactivation when they are stimulated by weak cross-linkage events. Cognate help is dependent on the binding of antigen by the B-cell's membrane immunoglobulin (Ig), the endocytosis of the antigen, and its fragmentation into peptides within the endosomal/lysosomal compartment of the cell. Some of the resultant peptides are loaded into a groove in a specialized set of cell surface proteins known as class II major histocompatibility complex (MHC) molecules. The resultant class II/peptide complexes are expressed on the cell surface and act as ligands for the antigen-specific receptors of a set of T-cells designated as CD4+ T-cells. The CD4+ T-cells bear receptors on their surface specific for the B-cell's class II/peptide complex. B-cell activation depends not only on the binding of the T cell through its T cell receptor (TCR), but this interaction also allows an activation ligand on the T-cell (CD40 ligand) to bind to its receptor on the B-cell (CD40) signaling B-cell activation. In addition, T helper cells secrete several cytokines that regulate the growth and differentiation of the stimulated B-cell by binding to cytokine receptors on the B cell. (Paul, W. E., "Chapter 1: The immune system: an introduction," Fundamental Immunology, 4th Edition, Ed. Paul, W. E., Lippicott-Raven Publishers, Philadelphia (1999)).

During cognate help for antibody production, the CD40 ligand is transiently expressed on activated CD4+ T helper cells, and it binds to CD40 on the antigen-specific B cells, thereby tranducing a second costimulatory signal. The latter signal is essential for B cell growth and differentiation and for the generation of memory B cells by preventing apoptosis of germinal center B cells that have encountered antigen. Hyperexpression of the CD40 ligand in both B and T cells is implicated in the pathogenic autoantibody production in human SLE patients. (Desai-Mehta, A. et al., "Hyperexpression of CD40 ligand by B and T cells in human lupus and its role in pathogenic autoantibody production," J. Clin. Invest., 97(9): 2063-2073 (1996)).

T-Lymphocytes

T-lymphocytes derive from precursors in hematopoietic tissue, undergo differentiation in the thymus, and are then seeded to peripheral lymphoid tissue and to the recirculating pool of lymphocytes. T-lymphocytes or T cells mediate a wide range of immunologic functions. These include the capacity to help B cells develop into antibody-producing cells, the capacity to increase the microbicidal action of monocytes/macrophages, the inhibition of certain types of immune responses, direct killing of target cells, and mobilization of the inflammatory response. These effects depend on their expression of specific cell surface molecules and the secretion of cytokines (Paul, W. E., "Chapter 1: The immune system: an introduction," Fundamental Immunology, 4th Edition, Ed. Paul, W. E., Lippicott-Raven Publishers, Philadelphia (1999)).

T cells differ from B cells in their mechanism of antigen recognition. Immunoglobulin, the B cell's receptor, binds to individual epitopes on soluble molecules or on particulate surfaces. B-cell receptors see epitopes expressed on the surface of native molecules. Antibody and B-cell receptors evolved to bind to and to protect against microorganisms in extracellular fluids. In contrast, T cells recognize antigens on the surface of other cells and mediate their functions by interacting with, and altering, the behavior of these antigen-presenting cells (APCs). There are three main types of antigen-presenting cells in peripheral lymphoid organs that can activate T cells: dendritic cells, macrophages and B cells. The most potent of these are the dendritic cells, whose only function is to present foreign antigens to T cells. Immature dendritic cells are located in tissues throughout the body, including the skin, gut, and respiratory tract. When they encounter invading microbes at these sites, they endocytose the pathogens and their products, and carry them via the lymph to local lymph nodes or gut associated lymphoid organs. The encounter with a pathogen induces the dendritic cell to mature from an antigen-capturing cell to an antigen-presenting cell (APC) that can activate T cells. APCs display three types of protein molecules on their surface that have a role in activating a T cell to become an effector cell: (1) MHC proteins, which present foreign antigen to the T cell receptor; (2) costimulatory proteins which bind to complementary receptors on the T cell surface; and (3) cell-cell adhesion molecules, which enable a T cell to bind to the antigen-presenting cell (APC) for long enough to become activated. ("Chapter 24: The adaptive immune system," Molecular Biology of the Cell, Alberts, B. et al., Garland Science, NY, 2002).

T-cells are subdivided into two distinct classes based on the cell surface receptors they express. The majority of T cells express T cell receptors (TCR) consisting of $\alpha$ and $\beta$ chains. A small group of T cells express receptors made of $\gamma$ and $\delta$ chains. Among the $\alpha/\beta$ T cells are two important sublineages: those that express the coreceptor molecule CD4 (CD4+ T cells); and those that express CD8 (CD8+ T cells). These cells differ in how they recognize antigen and in their effector and regulatory functions.

CD4+ T cells are the major regulatory cells of the immune system. Their regulatory function depends both on the expression of their cell-surface molecules, such as CD40 ligand whose expression is induced when the T cells are activated, and the wide array of cytokines they secrete when activated.

T cells also mediate important effector functions, some of which are determined by the patterns of cytokines they secrete. The cytokines can be directly toxic to target cells and can mobilize potent inflammatory mechanisms.

In addition, T cells particularly CD8+ T cells, can develop into cytotoxic T-lymphocytes (CTLs) capable of efficiently lysing target cells that express antigens recognized by the CTLs. (Paul, W. E., "Chapter 1: The immune system: an introduction," Fundamental Immunology, 4th Edition, Ed. Paul, W. E., Lippicott-Raven Publishers, Philadelphia (1999)).

T cell receptors (TCRs) recognize a complex consisting of a peptide derived by proteolysis of the antigen bound to a specialized groove of a class II or class I MHC protein. The CD4+ T cells recognize only peptide/class II complexes while the CD8+ T cells recognize peptide/class I complexes. (Paul, W. E., "Chapter 1: The immune system: an introduction," Fundamental Immunology, 4th Edition, Ed. Paul, W. E., Lippicott-Raven Publishers, Philadelphia (1999)).

The TCR's ligand (i.e., the peptide/MHC protein complex) is created within antigen-presenting cells (APCs). In general, class II MHC molecules bind peptides derived from proteins that have been taken up by the APC through an endocytic process. These peptide-loaded class II molecules are then expressed on the surface of the cell, where they are available to be bound by CD4+ T cells with TCRs capable of recognizing the expressed cell surface complex. Thus, CD4+ T cells are specialized to react with antigens derived from extracellular sources. (Paul, W. E., "Chapter 1: The immune system: an introduction," Fundamental Immunology, 4$^{th}$ Edition, Ed. Paul, W. E., Lippicott-Raven Publishers, Philadelphia (1999)).

In contrast, class I MHC molecules are mainly loaded with peptides derived from internally synthesized proteins, such as viral proteins. These peptides are produced from cytosolic proteins by proteolysis by the proteosome and are translocated into the rough endoplasmic reticulum. Such peptides, generally nine amino acids in length, are bound into the class I MHC molecules and are brought to the cell surface, where they can be recognized by CD8+ T cells expressing appropriate receptors. This gives the T cell system, particularly CD8+ T cells, the ability to detect cells expressing proteins that are different from, or produced in much larger amounts than, those of cells of the remainder of the organism (e.g., vial antigens) or mutant antigens (such as active oncogene products), even if these proteins in their intact form are neither expressed on the cell surface nor secreted. (Paul, W. E., "Chapter 1: The immune system: an introduction," Fundamental Immunology, 4$^{th}$ Edition, Ed. Paul, W. E., Lippicott-Raven Publishers, Philadelphia (1999)).

T cells can also be classified based on their function as helper T cells; T cells involved in inducing cellular immunity; suppressor T cells; and cytotoxic T cells.

Helper T Cells

Helper T cells are T cells that stimulate B cells to make antibody responses to proteins and other T cell-dependent antigens. T cell-dependent antigens are immunogens in which individual epitopes appear only once or a limited number of times such that they are unable to cross-link the membrane immunoglobulin (Ig) of B cells or do so inefficiently. B cells bind the antigen through their membrane Ig, and the complex undergoes endocytosis. Within the endosomal and lysosomal compartments, the antigen is fragmented into peptides by proteolytic enzymes and one or more of the generated peptides are loaded into class II MHC molecules, which traffic through this vesicular compartment. The resulting peptide/class II MHC complex is then exported to the B-cell surface membrane. T cells with receptors specific for the peptide/class II molecular complex recognize this complex on the B-cell surface. (Paul, W. E., "Chapter 1: The immune system: an introduction," Fundamental Immunology, 4$^{th}$ Edition, Ed. Paul, W. E., Lippicott-Raven Publishers, Philadelphia (1999)).

B-cell activation depends both on the binding of the T cell through its TCR and on the interaction of the T-cell CD40 ligand (CD40L) with CD40 on the B cell. T cells do not constitutively express CD40L. Rather, CD40L expression is induced as a result of an interaction with an APC that expresses both a cognate antigen recognized by the TCR of the T cell and CD80 or CD86. CD80/CD86 is generally expressed by activated, but not resting, B cells so that the helper interaction involving an activated B cell and a T cell can lead to efficient antibody production. In many cases, however, the initial induction of CD40L on T cells is dependent on their recognition of antigen on the surface of APCs that constitutively express CD80/86, such as dendritic cells. Such activated helper T cells can then efficiently interact with and help B cells. Cross-linkage of membrane Ig on the B cell, even if inefficient, may synergize with the CD40L/CD40 interaction to yield vigorous B-cell activation. The subsequent events in the B-cell response, including proliferation, Ig secretion, and class switching (of the Ig class being expressed) either depend or are enhanced by the actions of T cell-derived cytokines (Paul, W. E., "Chapter 1: The immune system: an introduction," Fundamental Immunology, 4$^{th}$ Edition, Ed. Paul, W. E., Lippicott-Raven Publishers, Philadelphia (1999)).

CD4+ T cells tend to differentiate into cells that principally secrete the cytokines IL-4, IL-5, IL-6, and IL-10 ($T_{H2}$ cells) or into cells that mainly produce IL-2, IFN-γ, and lymphotoxin ($T_{H1}$ cells). The $T_{H2}$ cells are very effective in helping B-cells develop into antibody-producing cells, whereas the $T_{H1}$ cells are effective inducers of cellular immune responses, involving enhancement of microbicidal activity of monocytes and macrophages, and consequent increased efficiency in lysing microorganisms in intracellular vesicular compartments. Although the CD4+ T cells with the phenotype of $T_{H2}$ cells (i.e., IL-4, IL-5, IL-6 and IL-10) are efficient helper cells, $T_{H1}$ cells also have the capacity to be helpers. (Paul, W. E., "Chapter 1: The immune system: an introduction," Fundamental Immunology, 4$^{th}$ Edition, Ed. Paul, W. E., Lippicott-Raven Publishers, Philadelphia (1999)).

T Cells Involved in Induction of Cellular Immunity

T cells also may act to enhance the capacity of monocytes and macrophages to destroy intracellular microorganisms. In particular, interferon-gamma (IFN-γ) produced by helper T cells enhances several mechanisms through which mononuclear phagocytes destroy intracellular bacteria and parasitism including the generation of nitric oxide and induction of tumor necrosis factor (TNF) production. The $T_{H1}$ cells are effective in enhancing the microbicidal action because they produce IFN-γ. By contrast, two of the major cytokines produced by $T_{H2}$ cells, IL-4 and IL-10, block these activities. (Paul, W. E., "Chapter 1: The immune system: an introduction," Fundamental Immunology, 4$^{th}$ Edition, Ed. Paul, W. E., Lippicott-Raven Publishers, Philadelphia (1999)).

Suppressor or Regulatory T (Treg) Cells

A controlled balance between initiation and downregulation of the immune response is important to maintain immune homeostasis. Both apoptosis and T cell anergy (a tolerance mechanism in which the T cells are intrinsically functionally inactivated following an antigen encounter (Scwartz, R. H., "T cell anergy," Annu Rev. Immunol., 21: 305-334 (2003)) are important mechanisms that contribute to the downregulation of the immune response. A third mechanism is provided by active suppression of activated T cells by suppressor or regulatory CD4+ T (Treg) cells. (Reviewed in Kronenberg, M. et al., "Regulation of immunity by self-reactive T cells," Nature 435: 598-604 (2005)). CD4+ Tregs that constitutively express the IL-2 receptor alpha (IL-2Ra) chain (CD4+CD25+) are a naturally occurring T cell subset that are anergic and suppressive. (Taams, L. S. et 1., "Human anergic/suppressive CD4+CD25+ T cells: a highly differentiated and apoptosis-prone population," Eur. J. Immunol., 31: 1122-1131 (2001)). Depletion of CD4$^+$CD25$^+$ Tregs results in systemic autoimmune disease in mice. Furthermore, transfer of these Tregs prevents development of autoimmune disease. Human CD4$^+$CD25$^+$ Tregs, similar to their murine counterpart, are generated in the thymus and are characterized by the ability to suppress proliferation of responder T cells through a cell-cell contact-dependent mechanism, the inability to produce IL-2, and the anergic phenotype in vitro. Human CD4$^+$CD25$^+$ T cells can be split into suppressive (CD25$^{high}$) and nonsuppressive (CD25$^{low}$) cells, according to the level of CD25 expression.

A member of the forkhead family of transcription factors, FOXP3, has been shown to be expressed in murine and human CD4+CD25+ Tregs and appears to be a master gene controlling CD4+CD25+ Treg development. (Battaglia, M. et al., "Rapamycin promotes expansion of functional CD4+ CD25+Foxp3+ regulator T cells of both healthy subjects and type 1 diabetic patients," J. Immunol., 177: 8338-8347 (200)).

Cytotoxic T Lymphocytes (CTL)

The CD8+ T cells that recognize peptides from proteins produced within the target cell have cytotoxic properties in that they lead to lysis of the target cells. The mechanism of CTL-induced lysis involves the production by the CTL of perforin, a molecule that can insert into the membrane of target cells and promote the lysis of that cell. Perforin-mediated lysis is enhanced by a series of enzymes produced by activated CTLs, referred to as granzymes. Many active CTLs also express large amounts of fas ligand on their surface. The interaction of fas ligand on the surface of CTL with fas on the surface of the target cell initiates apoptosis in the target cell, leading to the death of these cells. CTL-mediated lysis appears to be a major mechanism for the destruction of virally infected cells.

The term "lactate dehydrogenase" or "LDH" as used herein refers to a group of enzymes which include, but are not limited to, L-1 dehydrogenase and D-1 dehydrogenase. LDH functions include, but are not limited to, transfer of hydrogen to ferrictytochrome c or to cytochrome $b_2$, transfer of hydrogen to $NAD^+$, and the like. An increased amount of LDH in the blood may be a sign of tissue damage (e.g., heart tissue damage).

The term "macrophage inflammatory protein 1" or "MIP1" as used herein refers to a cytokine composed of several gene products that has been identified in activated T cells, macrophages, and fibroblasts. MIP1 exerts an effect, for example, on neutrophils, monocytes and hematopoietic cells and its functions include, but are not limited to, regulating inflammation and cell growth.

The term "macrophage inflammatory protein 2" or "MIP2" as used herein refers to platelet products including, but not limited to, platelet factor 4 and 3-thromboglobulin that have effects on a number of cell types including, but not limited to, neutrophils, fibroblasts, hematopoietic cells and melanoma cells. MIP2 functions include, but are not limited to, regulating inflammation and cell growth.

The term "MK2i peptide" or "MK2i" or "MMI-0100" as used interchangeably herein refers to a peptide of amino acid sequence YARAAARQARAKALARQLGVAA (SEQ ID NO: 1) comprising a fusion protein in which a protein transduction domain (PTD; YARAAARQARA; SEQ ID NO: 2) is operatively linked to a therapeutic domain (KALARQLGVAA; SEQ ID NO: 3).

The term "MK2 kinase" or "MK2" as used herein refers to mitogen-activated protein kinase-activated protein kinase 2 (also referred to as "MAPKAPK2", "MAPKAP-K2", "MK2"), which is a member of the serine/threonine (Ser/Thr) protein kinase family.

The term "modify" as used herein means to change, vary, adjust, temper, alter, affect or regulate to a certain measure or proportion in one or more particulars.

The term "modulate" as used herein means to regulate, alter, adapt, or adjust to a certain measure or proportion.

The term "normoxia" as used herein refers to a normal level of oxygen; a normal oxygen state.

The term "necrosis" refers to the premature death of cells and living tissue induced by external factors, such as infection, toxins or trauma. Necrotic tissue undergoes chemical reactions different from those of apoptotic tissue. Necrosis typically begins with cell swelling, chromatin digestion, disruption of the plasma membrane and of organelle membranes. Damage to the lysosome membrane can trigger release of lysosomal enzymes, destroying other parts of the cell. Late necrosis is characterized by extensive DNA hydrolysis, vacuolation of the endoplasmic reticulum, organelle breakdown and cell lysis. The release of intracellular content after plasma membrane rupture is the cause of inflammation in necrosis. Released lysosomal enzymes can trigger a chain reaction of further cell death. Necrosis of a sufficient amount of contiguous tissue can result in tissue death or gangrene.

The term "neutrophils" or "polymorphonuclear neutrophils (PMNs)" as used herein refers to the most abundant type of white blood cells in mammals, which form an essential part of the innate immune system. They form part of the polymorphonuclear cell family (PMNs) together with basophils and eosinophils. Neutrophils are normally found in the blood stream. During the beginning (acute) phase of inflammation, particularly as a result of bacterial infection and some cancers, neutrophils are one of the first-responders of inflammatory cells to migrate toward the site of inflammation. They migrate through the blood vessels, then through interstitial tissue, following chemical signals such as interleukin-8 (IL-8) and C5a in a process called chemotaxis, the directed motion of a motile cell or part along a chemical concentration gradient toward environmental conditions it deems attractive and/or away from surroundings it finds repellent.

The term "nucleic acid" is used herein to refer to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleotide" is used herein to refer to a chemical compound that consists of a heterocyclic base, a sugar, and one or more phosphate groups. In the most common nucleotides, the base is a derivative of purine or pyrimidine, and the sugar is the pentose deoxyribose or ribose. Nucleotides are the monomers of nucleic acids, with three or more bonding together in order to form a nucleic acid. Nucleotides are the structural units of RNA, DNA, and several cofactors, including, but not limited to, CoA, FAD, DMN, NAD, and NADP. Purines include adenine (A), and guanine (G); pyrimidines include cytosine (C), thymine (T), and uracil (U).

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity."

(a) The term "reference sequence" refers to a sequence used as a basis for sequence comparison. A reference sequence may be a subset or the entirety of a specified sequence; for example, as a segment of a full-length cDNA or gene sequence, or the complete cDNA or gene sequence.

(b) The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237-244 (1988); Higgins and Sharp, *CABIOS* 5:151-153 (1989); Corpet, et al., Nucleic Acids Research 16:10881-90 (1988); Huang, et al., Computer Applications in the *Biosciences*, 8:155-65 (1992), and Pearson, et al., *Methods in Molecular Biology*, 24:307-331 (1994). The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., *Nucleic Acids Res.* 25:3389-3402 (1997). Software for performing BLAST analyses is publicly available, e.g., through the National Center for Biotechnology-Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits then are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. BLAST searches assume that proteins may be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs may be employed to reduce such low-complexity alignments. For example, the SEG (Wooten and Federhen, *Comput. Chem.*, 17:149-163 (1993)) and XNU (Claverie and States, *Comput. Chem.*, 17:191-201 (1993)) low-complexity filters may be employed alone or in combination.

(c) The term "sequence identity" or "identity" in the context of two nucleic acid or polypeptide sequences is used herein to refer to the residues in the two sequences that are the same when aligned for maximum correspondence over a specified comparison window. When percentage of sequence identity is used in reference to proteins it is recognized that residue positions that are not identical often differ by conservative amino acid substitutions, i.e., where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4:11-17 (1988) e.g., as implemented in the program PC/GENE (Intelligenetics, Mountain View, Calif., USA).

(d) The term "percentage of sequence identity" is used herein mean the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70% sequence identity, at least 80% sequence identity, at least 90% sequence identity and at least 95% sequence identity, compared to a reference sequence using one of the alignment programs described using standard parameters. One of skill will recognize that these values may be adjusted appropriately to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or at least 70%, at least 80%, at least 90%, or at least 95%. Another indication that nucleotide sequences are substantially identical is if two molecules hybridize to each other under stringent conditions. However, nucleic acids that do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid.

As used herein, the terms "oral" or "orally" refer to the introduction into the body by mouth whereby absorption occurs in one or more of the following areas of the body: the mouth, stomach, small intestine, lungs (also specifically referred to as inhalation), and the small blood vessels under the tongue (also specifically referred to as sublingually). The term "pharmaceutical composition" as used herein refers to a preparation comprising a pharmaceutical product, drug, metabolite, or active ingredient.

The term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord), intrasternal injection, or infusion techniques. A parenterally administered composition of the described invention is delivered using a needle, e.g., a surgical needle. The term "surgical needle" as used herein, refers to any needle adapted for delivery of fluid (i.e., capable of flow) compositions of the described invention into a selected anatomical structure. Injectable preparations, such as sterile injectable aqueous or oleaginous suspensions, can be formulated according to the known art using suitable dispersing or wetting agents and suspending agents.

As used herein the term "pharmaceutically acceptable carrier" refers to any substantially non-toxic carrier conventionally useable for administration of pharmaceuticals in which the isolated polypeptide of the present invention will remain stable and bioavailable. The pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition.

The term "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

The term "phosphorylated-MK2 kinase", "phospho-MK2" or "p-MK2" as used herein refers to phosphorylated mitogen-activated protein kinase-activated protein kinase 2 (also referred to as "MAPKAPK2", "MAPKAP-K2", "MK2"), which is a member of the serine/threonine (Ser/Thr) protein kinase family.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids.

The terms "polypeptide" and "protein" also are used herein in their broadest sense to refer to a sequence of subunit amino acids, amino acid analogs, or peptidomimetics. The subunits are linked by peptide bonds, except where noted. The polypeptides described herein may be chemically synthesized or recombinantly expressed. Polypeptides of the described invention also can be synthesized chemically. Synthetic polypeptides, prepared using the well-known techniques of solid phase, liquid phase, or peptide condensation techniques, or any combination thereof, can include natural and unnatural amino acids. Amino acids used for peptide synthesis may be standard Boc (N-α-amino protected N-α-t-butyloxycarbonyl) amino acid resin with the standard deprotecting, neutralization, coupling and wash protocols of the original solid phase procedure of Merrifield (1963, *J. Am. Chem. Soc.* 85:2149-2154), or the base-labile N-α-amino protected 9-fluorenylmethoxycarbonyl (Fmoc) amino acids first described by Carpino and Han (1972, *J. Org. Chem.* 37:3403-3409). Both Fmoc and Boc N-α-amino protected amino acids can be obtained from Sigma, Cambridge Research Biochemical, or other chemical companies familiar to those skilled in the art. In addition, the polypeptides can be synthesized with other N-α-protecting groups that are familiar to those skilled in this art. Solid phase peptide synthesis may be accomplished by techniques familiar to those in the art and provided, for example, in Stewart and Young, 1984, *Solid Phase Synthesis*, Second Edition, Pierce Chemical Co., Rockford, Ill.; Fields and Noble, 1990, *Int. J. Pept. Protein Res.* 35:161-214, or using automated synthesizers. The polypeptides of the invention may comprise D-amino acids (which are resistant to L-amino acid-specific proteases in vivo), a combination of D- and L-amino acids, and various "designer" amino acids (e.g., β-methyl amino acids, C-α-methyl amino acids, and N-α-methyl amino acids, etc.) to convey special properties. Synthetic amino acids include ornithine for lysine, and norleucine for leucine or isoleucine. In addition, the polypeptides can have peptidomimetic bonds, such as ester bonds, to prepare peptides with novel properties. For example, a peptide may be generated that incorporates a reduced peptide bond, i.e., R1-$CH_2$—NH—R2, where R1 and R2 are amino acid residues or sequences. A reduced peptide bond may be introduced as a dipeptide subunit. Such a polypeptide would be resistant to protease activity, and would possess an extended half-live in vivo. Accordingly, these terms also apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, the protein is specifically reactive to antibodies elicited to the same protein but consisting entirely of naturally occurring amino acids.

The terms "polypeptide", "peptide" and "protein" also are inclusive of modifications including, but not limited to, glycosylation, lipid attachment, sulfation, gamma-carboxylation of glutamic acid residues, hydroxylation, and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural process and by entirely synthetic methods, as well. In some embodiments, the peptide is of any length or size.

The terms "preserve", "preserved", "preserving" or "preservation" as used herein refer to maintaining, keeping safe from harm or injury, protecting, sparing or maintaining function.

The terms "prevent", "prevented", "preventing" or "prevention" as used herein refer to the keeping, hindering or averting of an event, act, or action from happening, occurring or arising.

The term "reduce" or "reducing" as used herein refers to the limiting of an occurrence of a disorder in individuals at risk of developing the disorder.

The term "similar" is used interchangeably with the terms analogous, comparable, or resembling, meaning having traits or characteristics in common.

The term "solution" as used herein refers to a homogeneous mixture of two or more substances. It is frequently, though not necessarily, a liquid. In a solution, the molecules of the solute (or dissolved substance) are uniformly distributed among those of the solvent.

The terms "soluble" and "solubility" refer to the property of being susceptible to being dissolved in a specified fluid (solvent). The term "insoluble" refers to the property of a material that has minimal or limited solubility in a specified solvent. In a solution, the molecules of the solute (or dissolved substance) are uniformly distributed among those of the solvent.

The term "stimulate" in any of its grammatical forms as used herein refers to inducing activation or increasing activity.

The term "suspension" as used herein refers to a dispersion (mixture) in which a finely-divided species is combined with another species, with the former being so finely divided and mixed that it doesn't rapidly settle out. In everyday life, the most common suspensions are those of solids in liquid.

As used herein, the terms "subject" or "individual" or "patient" are used interchangeably to refer to a member of an animal species of mammalian origin, including humans. The term "a subject in need thereof" is used to refer to a subject having, or at risk of progression to heart failure, including a subject having an AMI that leads to a disease manifestation of left ventricular remodeling.

The phrase "subject in need of such treatment" as used herein refers to a patient who suffers from a disease, disorder, condition, or pathological process. In some embodiments, the term "subject in need of such treatment" also is used to refer to a patient who (i) will be administered at least one polypeptide of the invention; (ii) is receiving at least one polypeptide of the invention; or (iii) has received at least one polypeptide of the invention, unless the context and usage of the phrase indicates otherwise.

The term "substantially similar" as used herein means that a first value, aspect, trait, feature, number, or amount is of at least 70%, at least 75%, at least 80%, at least 85%, at least 90%, or at least 95% of a second value, aspect, trait, feature, number, or amount. For example, polypeptide substantially similar to MMI-0100 (YARAAARQARAKALARQLGVAA (SEQ ID NO: 1)) would have at least 70% amino acid sequence identity, at least 75% amino acid sequence identity, at least 80% amino acid sequence identity, at least 90% sequence identity, or at least 95% amino acid sequence identity to amino acid sequence YARAAARQARAKALARQLGVAA (SEQ ID NO: 1).

The term "substitution" is used herein to refer to a situation in which a base or bases are exchanged for another base or bases in a DNA sequence. Substitutions may be synonymous substitutions or nonsynonymous substitutions. As used herein, "synonymous substitutions" refer to substitutions of one base for another in an exon of a gene coding for a protein, such that the amino acid sequence produced is not modified. The term "nonsynonymous substitutions" as used herein refer to substitutions of one base for another in an exon of a gene coding for a protein, such that the amino acid sequence produced is modified.

The term "symptom" as used herein refers to a phenomenon that arises from and accompanies a particular disease or disorder and serves as an indication of it.

The term "syndrome," as used herein, refers to a pattern of symptoms indicative of some disease or condition.

The term "therapeutic agent" as used herein refers to a drug, molecule, nucleic acid, protein, metabolite, composition or other substance that provides a therapeutic effect. The term "active" as used herein refers to the ingredient, component or constituent of the compositions of the described invention responsible for the intended therapeutic effect. The terms "therapeutic agent" and "active agent" are used interchangeably herein. The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50 which describes the dose in a particular dosage that is therapeutically effective for a particular disease manifestation in 50% of a population.

The terms "therapeutic amount", "therapeutically effective amount", an "amount effective", or "pharmaceutically effective amount" of an active agent is used interchangeably to refer to an amount that is sufficient to provide the intended benefit of treatment. An effective amount of the active agent(s) that can be employed according to the described invention generally ranges from about 0.25 mg/kg body weight to about 160 mg/kg body weight per dose, with three doses given per day. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a physician using standard methods. Additionally, the terms "therapeutic amount", "therapeutically effective amount" and "pharmaceutically effective amount" includes prophylactic or preventative amounts of the compositions of the described invention. In prophylactic or preventative applications of the described invention, pharmaceutical compositions or medicaments are administered to a patient susceptible to, or otherwise at risk of, a disease, disorder or condition in an amount sufficient to eliminate or reduce the risk, lessen the severity, or delay the onset of the disease, disorder or condition, including biochemical, histologic and/or behavioral symptoms of the disease, disorder or condition, its complications, and intermediate pathological phenotypes presenting during development of the disease, disorder or condition. It is generally preferred that a maximum dose be used, that is, the highest safe dose according to some medical judgment. The terms "dose" and "dosage" are used interchangeably herein.

The term "therapeutic effect" as used herein refers to a consequence of treatment, the results of which are judged to be desirable and beneficial. A therapeutic effect can include, directly or indirectly, the arrest, reduction, or elimination of a disease manifestation. A therapeutic effect can also include, directly or indirectly, the arrest reduction or elimination of the progression of a disease manifestation.

For any therapeutic agent described herein the therapeutically effective amount may be initially determined from preliminary in vitro studies and/or animal models. A therapeutically effective dose may also be determined from human data. The applied dose may be adjusted based on the relative bioavailability and potency of the administered compound. Adjusting the dose to achieve maximal efficacy based on the methods described above and other well-known methods is within the capabilities of the ordinarily skilled artisan.

General principles for determining therapeutic effectiveness, which may be found in Chapter 1 of Goodman and Gilman's The Pharmacological Basis of Therapeutics, 10th Edition, McGraw-Hill (New York) (2001), incorporated herein by reference, are summarized below.

Pharmacokinetic principles provide a basis for modifying a dosage regimen to obtain a desired degree of therapeutic efficacy with a minimum of unacceptable adverse effects. In situations where the drug's plasma concentration can be measured and related to the therapeutic window, additional guidance for dosage modification can be obtained.

Drug products are considered to be pharmaceutical equivalents if they contain the same active ingredients and are identical in strength or concentration, dosage form, and route of administration. Two pharmaceutically equivalent drug products are considered to be bioequivalent when the rates and extents of bioavailability of the active ingredient in the two products are not significantly different under suitable test conditions.

The term "therapeutic window" refers to a concentration range that provides therapeutic efficacy without unacceptable toxicity. Following administration of a dose of a drug, its effects usually show a characteristic temporal pattern. A lag period is present before the drug concentration exceeds the minimum effective concentration ("MEC") for the desired effect. Following onset of the response, the intensity of the effect increases as the drug continues to be absorbed and distributed. This reaches a peak, after which drug elimination results in a decline in the effect's intensity that disappears when the drug concentration falls back below the MEC. Accordingly, the duration of a drug's action is determined by the time period over which concentrations exceed the MEC. The therapeutic goal is to obtain and maintain concentrations within the therapeutic window for the desired response with a minimum of toxicity. Drug response below the MEC for the desired effect will be subtherapeutic, whereas for an adverse effect, the probability of toxicity will increase above the MEC. Increasing or decreasing drug dosage shifts the response curve up or down the intensity scale and is used to modulate the drug's effect. Increasing the dose also prolongs a drug's duration of action but at the risk of increasing the likelihood of adverse effects. Accordingly, unless the drug is nontoxic, increasing the dose is not a useful strategy for extending a drug's duration of action.

Instead, another dose of drug should be given to maintain concentrations within the therapeutic window. In general, the lower limit of the therapeutic range of a drug appears to be approximately equal to the drug concentration that produces about half of the greatest possible therapeutic effect, and the upper limit of the therapeutic range is such that no more than about 5% to about 10% of patients will experience a toxic effect. These figures can be highly variable, and some patients may benefit greatly from drug concentrations that exceed the therapeutic range, while others may suffer significant toxicity at much lower values. The therapeutic goal is to maintain steady-state drug levels within the therapeutic window. For most drugs, the actual concentrations associated with this desired range are not and need not be known, and it is sufficient to understand that efficacy and toxicity are generally concentration-dependent, and how drug dosage and frequency of administration affect the drug level. For a small number of drugs where there is a small (two- to three-fold) difference between concentrations resulting in efficacy and toxicity, a plasma-concentration range associated with effective therapy has been defined.

In this case, a target level strategy is reasonable, wherein a desired target steady-state concentration of the drug (usually in plasma) associated with efficacy and minimal toxicity is chosen, and a dosage is computed that is expected to achieve this value. Drug concentrations subsequently are measured and dosage is adjusted if necessary to approximate the target more closely.

In most clinical situations, drugs are administered in a series of repetitive doses or as a continuous infusion to maintain a steady-state concentration of drug associated with the therapeutic window. To maintain the chosen steady-state or target concentration ("maintenance dose"), the rate of drug administration is adjusted such that the rate of input equals the rate of loss. If the clinician chooses the desired concentration of drug in plasma and knows the clearance and bioavailability for that drug in a particular patient, the appropriate dose and dosing interval can be calculated.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

The term "tumor necrosis factor alpha (a)" or "TNF-α" (also known as cachectin and TNFSF2) as used herein refers to a pleiotropic molecule that plays a central role in inflammation, apoptosis, and immune system development. TNF-α is produced by a wide variety of immune and epithelial cell types. Human TNF-α consists of a 35 amino acid cytoplasmic domain, a 21 amino acid transmembrane segment, and a 177 amino acid extracellular domain. Cleavage of membrane bound TNF-α by TACE/ADAM17 releases a 55 kDa soluble trimeric form of TNF-α. TNF-α trimers bind the ubiquitous TNF RI and the hematopoietic cell-restricted TNF RII, both of which are also expressed as homotrimers. TNF-α regulates lymphoid tissue development through control of apoptosis. It also promotes inflammatory responses by inducing the activation of vascular endothelial cells and macrophages. TNF-α is a key cytokine in the development of several inflammatory disorders. It contributes to the development of type 2 diabetes through its effects on insulin resistance and fatty acid metabolism.

The terms "variants", "mutants", and "derivatives" are used herein to refer to nucleotide or polypeptide sequences with substantial identity to a reference nucleotide or polypeptide sequence. The differences in the sequences may be the result of changes, either naturally or by design, in sequence or structure. Natural changes may arise during the course of normal replication or duplication in nature of the particular nucleic acid sequence. Designed changes may be specifically designed and introduced into the sequence for specific purposes. Such specific changes may be made in vitro using a variety of mutagenesis techniques. Such sequence variants generated specifically may be referred to as "mutants" or "derivatives" of the original sequence.

A skilled artisan likewise can produce polypeptide variants of polypeptide YARAAARQARAKALARQLGVAA (SEQ ID NO: 1) having single or multiple amino acid substitutions, deletions, additions or replacements, but functionally equivalent to SEQ ID NO: 1. These variants may include inter alia: (a) variants in which one or more amino acid residues are substituted with conservative or non-conservative amino acids; (b) variants in which one or more amino acids are added; (c) variants in which at least one amino acid includes a substituent group; (d) variants in which amino acid residues from one species are substituted for the corresponding residue in another species, either at conserved or non-conserved positions; and (d) variants in which a target protein is fused with another peptide or polypeptide such as a fusion partner, a protein tag or other chemical moiety, that may confer useful properties to the target protein, for example, an epitope for an antibody. The techniques for obtaining such variants, including, but not limited to, genetic (suppressions, deletions, mutations, etc.), chemical, and enzymatic techniques, are known to the skilled artisan. As used herein, the term "mutation" refers to a change of the DNA sequence within a gene or chromosome of an organism resulting in the creation of a new character or trait not found in the parental type, or the process by which such a change occurs in a chromosome, either through an alteration in the nucleotide sequence of the DNA coding for a gene or through a change in the physical arrangement of a chromosome. Three mechanisms of mutation include substitution (exchange of one base pair for another), addition (the insertion of one or more bases into a sequence), and deletion (loss of one or more base pairs).

The term "vehicle" as used herein refers to a substance that facilitates the use of a drug or other material that is mixed with it.

According to one embodiment, the described invention provides a pharmaceutical composition comprising a therapeutic amount of a Mitogen-Activated Protein Kinase-Activated Protein Kinase 2 (MK2) inhibitor comprising an MK2 polypeptide inhibitor or a functional equivalent thereof, and a pharmaceutically acceptable carrier. According to another embodiment, the MK2 polypeptide inhibitor is a polypeptide MMI-0100 of amino acid sequence YARAAARQARAKALARQLGVAA (SEQ ID NO: 1).

According to one embodiment, the described invention provides a kit comprising a pharmaceutical composition and a packaging material. According to another embodiment, the kit further comprises a means for administering the pharmaceutical composition. According to another embodiment, the pharmaceutical composition comprises a therapeutic amount of a Mitogen-Activated Protein Kinase-Activated Protein Kinase 2 (MK2) inhibitor comprising an MK2 polypeptide inhibitor or a functional equivalent thereof. According to another embodiment, the packaging material is an instruction. According to another embodiment, the composition of the kit further comprises a pharmaceutically acceptable excipient.

According to one embodiment, the described invention provides a method for inhibiting kinase activity of a kinase. According to another embodiment, the kinase activity is MK2 kinase activity.

According to one embodiment, the described invention provides a method for reducing fibroblast proliferation, extracellular matrix deposition, or a combination thereof in a tissue of a subject. According to another embodiment, the tissue is cardiac tissue.

According to one embodiment, the described invention provides a method for preserving heart function or improving cardiac function after myocardial infarction (MI). Cardiac function can be measured by techniques known to one skilled in the art. Such measurements include, but are not limited to, echocardiography, ejection fraction, fractional shortening, ventricular volume and end diastolic diameter. Preserving heart function includes, without limitation, maintaining ejection fraction, maintaining fractional shortening, and decreasing left ventricular dilation compared to an untreated control subject.

According to one embodiment, the described invention provides a method for attenuating cardiac dilation after MI.

According to one embodiment, the described invention provides a method for protecting cardiomyocytes after MI. Protecting cardiomyocytes includes, but is not limited to, reducing cardiac fibrosis, muscle sparing, and preserving systolic function. Protecting cardiomyocytes can be determined by techniques available to one of skill in the art. Such techniques include, but are not limited to, echocardiography.

According to one embodiment, the described invention provides a method for reducing at least one pathology selected from the group consisting of an aberrant deposition of an extracellular matrix protein, an aberrant promotion of fibroblast proliferation in the heart, an aberrant induction of myofibroblast differentiation, and an aberrant promotion of attachment of myofibroblasts to an extracellular matrix, compared to a normal healthy control subject.

According to one embodiment, the described invention provides a method for reducing fibrosis after MI. According to another embodiment, the reduction in fibrosis is 50%. According to another embodiment, the reduction in fibrosis is greater than 50%. According to another embodiment, the reduction in fibrosis is greater than 50%.

According to one embodiment, the described invention provides a method for inhibiting apoptosis. According to one embodiment, the method comprises inhibiting caspase 3/7 activity. According to another embodiment the described invention provides a method for enhancing lactate dehydrogenase (LDH) release. According to another embodiment, the described invention provides a method for inhibiting apoptosis.

According to one embodiment, the described invention provides a method for inhibiting heterogeneous nuclear ribonucleoprotein A0 (HNRNPA0) expression, activation or a combination thereof.

According to one embodiment, the described invention provides a method for enhancing fibroblast cell death. Cell death includes, but is not limited, necrosis and apoptosis. According to another embodiment, the described invention provides a method for decreasing fibroblast viability. According to another embodiment, the fibroblast is a cardiac fibroblast. According to another embodiment, the cardiac fibroblast is a myofibroblast.

According to one embodiment, the functional equivalent of the MK2 polypeptide inhibitor MMI-0100 of amino acid sequence YARAAARQARAKALARQLGVAA (SEQ ID NO: 1) has a substantial sequence identity to the amino acid sequence YARAAARQARAKALARQLGVAA (SEQ ID NO: 1).

According to one embodiment, the functional equivalent of the MK2 polypeptide inhibitor MMI-0100 of amino acid sequence YARAAARQARAKALARQLGVAA (SEQ ID NO: 1) has at least 70 percent sequence identity to the amino acid sequence YARAAARQARAKALARQLGVAA (SEQ ID NO: 1). According to another embodiment, the functional equivalent of the MK2 polypeptide inhibitor MMI-0100 of amino acid sequence YARAAARQARAKALARQLGVAA (SEQ ID NO: 1) has at least 75 percent sequence identity to the amino acid sequence YARAAARQARAKALARQLGVAA (SEQ ID NO: 1). According to another embodiment, the functional equivalent of the MK2 polypeptide inhibitor MMI-0100 of amino acid sequence YARAAARQARAKALARQLGVAA (SEQ ID NO: 1) has at least 80 percent sequence identity to the amino acid sequence YARAAARQARAKALARQLGVAA (SEQ ID NO: 1). According to another embodiment, the functional equivalent of the MK2 polypeptide inhibitor MMI-0100 of amino acid sequence YARAAARQARAKALARQLGVAA (SEQ ID NO: 1) has at least 85 percent sequence identity to the amino acid sequence YARAAARQARAKALARQLGVAA (SEQ ID NO: 1). According to another embodiment, the functional equivalent of the MK2 polypeptide inhibitor MMI-0100 of amino acid sequence YARAAARQARAKALARQLGVAA (SEQ ID NO: 1) has at least 90 percent sequence identity to the amino acid sequence YARAAARQARAKALARQLGVAA (SEQ ID NO: 1). According to another embodiment, the functional equivalent of the MK2 polypeptide inhibitor MMI-0100 of amino acid sequence YARAAARQARAKALARQLGVAA (SEQ ID NO: 1) has at least 95 percent sequence identity to the amino acid sequence YARAAARQARAKALARQLGVAA (SEQ ID NO: 1).

According to one embodiment, the MMI-0100 peptide (YARAAARQARAKALARQLGVAA (SEQ ID NO: 1)) of the described invention comprises a fusion protein in which a cell penetrating peptide (CPP; YARAAARQARA; SEQ ID NO: 2) is operatively linked to a therapeutic domain (TD; KALARQLGVAA; SEQ ID NO: 3) in order to enhance therapeutic efficacy.

Examples of polypeptides functionally equivalent to the therapeutic domain (TD; KALARQLGVAA; SEQ ID NO: 3) of the polypeptide YARAAARQARAKALARQLGVAA (SEQ ID NO: 1) include, but are not limited to, a polypeptide of amino acid sequence KALARQLAVA (SEQ ID NO: 9), a polypeptide of amino acid sequence KALARQLGVA (SEQ ID NO: 10), a polypeptide of amino acid sequence KALARQLGVAA (SEQ ID NO: 11), a polypeptide of amino acid sequence KALNRQLGVAA (SEQ ID NO: 12), a polypeptide of amino acid sequence KAANRQLGVAA (SEQ ID NO: 13), a polypeptide of amino acid sequence KALNAQLGVAA (SEQ ID NO: 14), a polypeptide of amino acid sequence KALNRALGVAA (SEQ ID NO: 15), a polypeptide of amino acid sequence KALNRQAGVAA (SEQ ID NO: 16), a polypeptide of amino acid sequence KALNRQLAVA (SEQ ID NO: 17), a polypeptide of amino acid sequence KALNRQLAVAA (SEQ ID NO: 18), a polypeptide of amino acid sequence KALNRQLGAAA (SEQ ID NO: 19), and a polypeptide of amino acid sequence KALNRQLGVA (SEQ ID NO: 20).

Examples of polypeptides functionally equivalent to the cell penetrating peptide (CPP; YARAAARQARA; SEQ ID NO: 2) of the polypeptide YARAAARQARAKALARQLGVAA (SEQ ID NO: 1) include, but are not limited to, a polypeptide of amino acid sequence WLRRIKAWLRRIKA (SEQ ID NO: 21), a polypeptide of amino acid sequence WLRRIKA (SEQ ID NO: 22), a polypeptide of amino acid sequence YGRKKRRQRRR (SEQ ID NO: 23), a polypeptide of amino acid sequence WLRRIKAWLRRI (SEQ ID NO: 24), a polypeptide of amino acid sequence FAKLAARLYR (SEQ ID NO: 25), a polypeptide of amino acid sequence KAFAKLAARLYR (SEQ ID NO: 26), and a polypeptide of amino acid sequence HRRIKAWLKKI (SEQ ID NO: 27).

According to one embodiment, the pharmaceutical composition inhibits a kinase activity of a kinase. According to another embodiment, the kinase activity is MK2 kinase activity.

According to one embodiment, kinase inhibition may, for example, be effective to reduce fibroblast proliferation, extracellular matrix deposition, or a combination thereof in a tissue of a subject. According to another embodiment, the tissue is cardiac tissue.

According to one embodiment, the kinase inhibition may, for example, be effective to improve cardiac function after myocardial infarction (MI). Cardiac function can be measured by techniques known to one skilled in the art. Such measurements include, but are not limited to, echocardiography, ejection fraction, fractional shortening, ventricular volume and end diastolic diameter. Improved cardiac function includes, but is not limited to, increased ejection fraction, increased fractional shortening, and decreased left ventricular dilation, compared to an untreated control subject.

According to one embodiment, the kinase inhibition may, for example, be effective to attenuate cardiac dilation after MI.

According to one embodiment, the kinase inhibition may, for example, be effective to protect cardiomyocytes after MI. Protection of cardiomyocytes includes, but is not limited to, a reduction in cardiac fibrosis, muscle sparing, and preservation of systolic function. Protection of cardiomyocytes can be determined by techniques available to one of skill in the art. Such techniques include, but are not limited to, echocardiography.

According to one embodiment, the kinase inhibition may, for example, be effective to reduce at least one pathology selected from the group consisting of an aberrant deposition of an extracellular matrix protein, an aberrant promotion of fibroblast proliferation in the heart, an aberrant induction of myofibroblast differentiation, and an aberrant promotion of attachment of myofibroblasts to an extracellular matrix, compared to a normal healthy control subject.

According to one embodiment, the kinase inhibition may, for example, be effective to reduce fibrosis. According to another embodiment, the reduction in fibrosis is 50%. According to another embodiment, the reduction in fibrosis is less than 50%. According to another embodiment, the reduction in fibrosis is greater than 50%.

According to one embodiment, the kinase inhibition may, for example, be effective to inhibit caspase 3/7 activity. According to another embodiment, the inhibition may, for example, be effective to enhance lactate dehydrogenase (LDH) release. According to another embodiment, the inhibition may, for example, be effective to inhibit apoptosis.

According to one embodiment, the kinase inhibition may, for example, be effective to inhibit heterogeneous nuclear ribonucleoprotein A0 (HNRNPA0) expression.

According to one embodiment, the kinase inhibition may, for example, be effective to enhance fibroblast cell death. Cell death includes, but is not limited, necrosis and apoptosis. According to another embodiment, the inhibition may, for example, be effective to decrease fibroblast viability. According to another embodiment, the fibroblast is a cardiac fibroblast. According to another embodiment, the cardiac fibroblast is a myofibroblast.

According to some embodiments, inhibitory profiles of MMI inhibitors in vivo depend on dosages, routes of administration, and cell types responding to the inhibitors.

According to another embodiment, the pharmaceutical composition inhibits at least 50% of the kinase activity of the kinase. According to another embodiment, the pharmaceutical composition inhibits at least 65% of the kinase activity of the kinase. According to another embodiment, the pharmaceutical composition inhibits at least 75% of the kinase activity of that kinase. According to another embodiment, the pharmaceutical composition inhibits at least 80% of the kinase activity of that kinase. According to another embodiment, the pharmaceutical composition inhibits at least 85% of the kinase activity of that kinase. According to another embodiment, the pharmaceutical composition inhibits at least 90% of the kinase activity of that kinase. According to another embodiment, the pharmaceutical composition inhibits at least 95% of the kinase activity of that kinase.

According to some embodiments, the pharmaceutical composition inhibits a kinase activity of Mitogen-Activated Protein Kinase-Activated Protein Kinase 2 (MK2 kinase). According to some other embodiments, the pharmaceutical composition inhibits at least 50% of the kinase activity of MK2 kinase. According to some other embodiments, the pharmaceutical composition inhibits at least 65% of the kinase activity of MK2 kinase. According to another embodiment, the pharmaceutical composition inhibits at least 75% of the kinase activity of MK2 kinase. According to another embodiment, the pharmaceutical composition inhibits at least 80% of the kinase activity of MK2 kinase. According to another embodiment, the pharmaceutical composition inhibits at least 85% of the kinase activity of MK2 kinase. According to another embodiment, the pharmaceutical composition inhibits at least 90% of the kinase activity of MK2 kinase. According to another embodiment, the pharmaceutical composition inhibits at least 95% of the kinase activity of MK2 kinase.

According to some other embodiments, the therapeutic amount of the therapeutic inhibitor peptide of the pharmaceutical composition is of an amount from about 0.000001 mg/kg body weight to about 100 mg/kg body weight. According to another embodiment, the therapeutic amount of the therapeutic inhibitory peptide of the pharmaceutical composition is of an amount from about 0.00001 mg/kg body weight to about 100 mg/kg body weight. According to another embodiment, the therapeutic amount of the therapeutic inhibitory peptide of the pharmaceutical composition is of an amount from about 0.0001 mg/kg body weight to about 100 mg/kg body weight. According to another embodiment, the therapeutic amount of the therapeutic inhibitory peptide of the pharmaceutical composition is of an amount from about 0.001 mg/kg body weight to about 10 mg/kg body weight. According to another embodiment, the therapeutic amount of the therapeutic inhibitory peptide of the pharmaceutical composition is of an amount from about 0.01 mg/kg body weight to about 10 mg/kg body weight. According to another embodiment, the therapeutic amount of the therapeutic inhibitory peptide of the pharmaceutical composition is of an amount from about 0.1 mg/kg (or 100 μg/kg) body weight to about 10 mg/kg body weight. According to another embodiment, the therapeutic amount of the therapeutic inhibitory peptide of the pharmaceutical composition is of an amount from about 1 mg/kg body weight to about 10 mg/kg body weight. According to another embodiment, the therapeutic amount of the therapeutic inhibitory peptide of the pharmaceutical composition is of an amount from about 10 mg/kg body weight to about 100 mg/kg body weight. According to another embodiment, the therapeutic amount of the therapeutic inhibitory peptide of the pharmaceutical composition is of an amount from about 2 mg/kg body weight to about 10 mg/kg body weight. According to another embodiment, the therapeutic amount of the therapeutic inhibitory peptide of the pharmaceutical composition is of an amount from about 3 mg/kg body weight to about 10 mg/kg body weight. According to another embodiment, the therapeutic amount of the therapeutic inhibitory peptide of the pharmaceutical composition is of an amount from about 4 mg/kg body weight to about 10 mg/kg body weight. According to another embodiment, the therapeutic amount of the therapeutic inhibitory peptide of the pharmaceutical composition is of an amount from about 5 mg/kg body weight to about 10 mg/kg body weight. According to another embodiment, the therapeutic amount of the therapeutic inhibitory peptide of the pharmaceutical composition is of an amount from about 60 mg/kg body weight to about 100 mg/kg body weight. According to another embodiment, the therapeutic amount of the therapeutic inhibitory peptide of the pharmaceutical composition is of an amount from about 70 mg/kg body weight to about 100 mg/kg body weight. According to another embodiment, the therapeutic amount of the therapeutic inhibitory peptide of the pharmaceutical composition is of an amount from about 80 mg/kg body weight to about 100 mg/kg body weight. According to another embodiment, the therapeutic amount of the therapeutic inhibitory peptide of the pharmaceutical composition is of an amount from about 90 mg/kg body weight to about 100 mg/kg body weight. According to another embodiment, the therapeutic amount of the therapeutic inhibitor peptide of the pharmaceutical composition is of an amount from about 0.000001 mg/kg body weight to about 90 mg/kg body weight. According to another embodiment, the therapeutic amount of the therapeutic inhibitor peptide of the pharmaceutical composition is of an amount from about 0.000001 mg/kg body weight to about 80 mg/kg body weight. According to another embodiment, the therapeutic amount of the therapeutic inhibitor peptide of the pharmaceutical composition is of an amount from about 0.000001 mg/kg body weight to about 70 mg/kg body weight. According to another embodiment, the therapeutic amount of the therapeutic inhibitor peptide of the pharmaceutical composition is of an amount from about 0.000001 mg/kg body weight to about 60 mg/kg body weight. According to another embodiment, the therapeutic amount of the therapeutic inhibitor peptide of the pharmaceutical composition is of an amount from about 0.000001 mg/kg body weight to about 50 mg/kg body weight. According to another embodiment, the therapeutic amount of the therapeutic inhibitor peptide of the pharmaceutical composition is of an amount from about 0.000001 mg/kg body weight to about 40 mg/kg body weight. According to another embodiment, the therapeutic amount of the therapeutic inhibitor peptide is of an amount from about 0.000001 mg/kg body weight to about 30 mg/kg body weight. According to another embodiment, the therapeutic amount of the therapeutic inhibitor peptide of the pharmaceutical composition is of an amount from about 0.000001 mg/kg body weight to about 20 mg/kg body weight. According to another embodiment, the therapeutic amount of the therapeutic inhibitor peptide of the pharmaceutical composition is of an amount from about 0.000001 mg/kg body weight to about 10 mg/kg body weight. According to another embodiment, the therapeutic amount of the therapeutic inhibitor peptide of the pharmaceutical composition is of an amount from about 0.000001 mg/kg body weight to about 1 mg/kg body weight. According to another embodiment, the therapeutic amount of the therapeutic inhibitor peptide of the pharmaceutical composition is of an amount from about 0.000001 mg/kg body weight to about 0.1 mg/kg body weight. According to another embodiment, the therapeutic amount of the therapeutic inhibitor peptide of the pharmaceutical composition is of an amount from about 0.000001 mg/kg body weight to about 0.1 mg/kg body weight. According to another embodiment, the therapeutic amount of the therapeutic inhibitor peptide of the pharmaceutical composition is of an amount from about 0.000001 mg/kg body weight to about 0.01 mg/kg body weight. According to another embodiment, the therapeutic amount of the therapeutic inhibitor peptide of the pharmaceutical composition is of an amount from about 0.000001 mg/kg body weight to about 0.001 mg/kg body weight. According to another embodiment, the therapeutic amount of the therapeutic inhibitor peptide of the pharmaceutical composition is of an amount from about 0.000001 mg/kg body weight to about 0.0001 mg/kg body weight. According to another embodiment, the therapeutic amount of the therapeutic inhibitor peptide of the pharmaceutical composition is of an amount from about 0.000001 mg/kg body weight to about 0.00001 mg/kg body weight.

According to some other embodiments, the therapeutic dose of the therapeutic inhibitor peptide of the pharmaceutical composition ranges from 1 µg/kg/day to 25 µg/kg/day. According to some other embodiments, the therapeutic dose of the therapeutic inhibitor peptide of the pharmaceutical composition ranges from 1 µg/kg/day to 2 µg/kg/day. According to some other embodiments, the therapeutic dose of the therapeutic inhibitor peptide of the pharmaceutical composition ranges from 2 µg/kg/day to 3 µg/kg/day. According to some other embodiments, the therapeutic dose of the therapeutic inhibitor peptide of the pharmaceutical composition ranges from 3 µg/kg/day to 4 µg/kg/day. According to some other embodiments, the therapeutic dose of the therapeutic inhibitor peptide of the pharmaceutical ranges from 4 µg/kg/day to 5 µg/kg/day. According to some other embodiments, the therapeutic dose of the therapeutic inhibitor peptide of the pharmaceutical composition ranges from 5 µg/kg/day to 6 µg/kg/day. According to some other embodiments, the therapeutic dose of the therapeutic inhibitor peptide of the pharmaceutical composition ranges from 6 µg/kg/day to 7 µg/kg/day. According to some other embodiments, the therapeutic dose of the therapeutic inhibitor peptide of the pharmaceutical composition ranges from 7 µg/kg/day to 8 µg/kg/day. According to some other embodiments, the therapeutic dose of the therapeutic inhibitor peptide of the pharmaceutical composition ranges from 8 µg/kg/day to 9 µg/kg/day. According to some other embodiments, the therapeutic dose of the therapeutic inhibitor peptide of the pharmaceutical composition ranges from 9 µg/kg/day to 10 µg/kg/day. According to some other embodiments, the therapeutic dose of the therapeutic inhibitor peptide of the pharmaceutical composition ranges from 1 µg/kg/day to 5 µg/kg/day. According to some other embodiments, the therapeutic dose of the therapeutic inhibitor peptide of the pharmaceutical composition ranges from 5 µg/kg/day to 10 µg/kg/day. According to some other embodiments, the therapeutic dose of the therapeutic inhibitor peptide of the pharmaceutical composition ranges from 10 µg/kg/day to 15 µg/kg/day. According to some other embodiments, the therapeutic dose of the therapeutic inhibitor peptide of the pharmaceutical composition ranges from 15 µg/kg/day to 20 µg/kg/day. According to some other embodiments, the therapeutic dose of the therapeutic inhibitor peptide of the pharmaceutical composition ranges from 25 µg/kg/day to 30 µg/kg/day. According to some other embodiments, the therapeutic dose of the therapeutic inhibitor peptide of the pharmaceutical composition ranges from 30 µg/kg/day to 35 µg/kg/day. According to some other embodiments, the therapeutic dose of the therapeutic inhibitor peptide of the pharmaceutical composition ranges from 35 µg/kg/day to 40 µg/kg/day. According to some other embodiments, the therapeutic dose of the therapeutic inhibitor peptide of the pharmaceutical composition ranges from 40 µg/kg/day to 45 µg/kg/day. According to some other embodiments, the therapeutic dose of the therapeutic inhibitor peptide of the pharmaceutical composition ranges from 45 µg/kg/day to 50 µg/kg/day. According to some other embodiments, the therapeutic dose of the therapeutic inhibitor peptide of the pharmaceutical composition ranges from 50 µg/kg/day to 55 µg/kg/day. According to some other embodiments, the therapeutic dose of the therapeutic inhibitor peptide of the pharmaceutical composition ranges from 55 µg/kg/day to 60 µg/kg/day. According to some other embodiments, the therapeutic dose of the therapeutic inhibitor peptide of the pharmaceutical composition ranges from 60 µg/kg/day to 65 µg/kg/day. According to some other embodiments, the therapeutic dose of the therapeutic inhibitor peptide of the pharmaceutical composition ranges from 65 µg/kg/day to 70 µg/kg/day. According to some other embodiments, the therapeutic dose of the therapeutic inhibitor peptide of the pharmaceutical composition ranges from 70 µg/kg/day to 75 µg/kg/day. According to some other embodiments, the therapeutic dose of the therapeutic inhibitor peptide of the pharmaceutical composition ranges from 80 µg/kg/day to 85 µg/kg/day. According to some other embodiments, the therapeutic dose of the therapeutic inhibitor peptide of the pharmaceutical composition ranges from 85 µg/kg/day to 90 µg/kg/day. According to some other embodiments, the therapeutic dose of the therapeutic inhibitor peptide of the pharmaceutical composition ranges from 90 µg/kg/day to 95 µg/kg/day. According to some other embodiments, the therapeutic dose of the therapeutic inhibitor peptide of the pharmaceutical composition ranges from 95 µg/kg/day to 100 µg/kg/day.

According to some embodiments, the polypeptide of the invention comprises D-amino acids (which are resistant to L-amino acid-specific proteases in vivo), a combination of D- and L-amino acids, and various "designer" amino acids (e.g., β-methyl amino acids, C-α-methyl amino acids, and N-α-methyl amino acids, etc.) to convey special properties. Examples of synthetic amino acid substitutions include ornithine for lysine, and norleucine for leucine or isoleucine.

According to some embodiments, the polypeptide may be linked to other compounds to promote an increased half-life in vivo, such as polyethylene glycol or dextran. Such linkage can be covalent or non-covalent as is understood by those of skill in the art. According to some other embodiments, the polypeptide may be encapsulated in a micelle such as a micelle made of poly(ethyleneglycol)-block-poly(polypropylenglycol) or poly(ethyleneglycol)-block-polylactide. According to some other embodiments, the polypeptide may be encapsulated in degradable nano- or micro-particles composed of degradable polyesters including, but not limited to, polylactic acid, polyglycolide, and polycaprolactone.

According to one embodiment, the carrier of the composition of the described invention includes a release agent, such as a sustained release or delayed release carrier. In such embodiments, the carrier can be any material capable of sustained or delayed release of the polypeptide to provide a more efficient administration, e.g., resulting in less frequent and/or decreased dosage of the polypeptide, improving ease of handling, and extending or delaying effects on diseases, disorders, conditions, syndromes, and the like, being treated, prevented or promoted. Non-limiting examples of such carriers include liposomes, microsponges, microspheres, or microcapsules of natural and synthetic polymers and the like. Liposomes may be formed from a variety of phospholipids, including, but not limited to, cholesterol, stearylamines or phosphatidylcholines.

Methods for synthesis and preparation of small peptides are well known in the art and are disclosed, for example, in U.S. Pat. Nos. 5,352,461; 5,503,852; 6,071,497; 6,331,318; 6,428,771 and U.S. Publication No. 20060040953. U.S. Pat. Nos. 6,444,226 and 6,652,885 describe preparing and providing microparticles of diketopiperazines in aqueous suspension to which a solution of active agent is added in order to bind the active agent to the particle. These patents further describe a method of removing a liquid medium by lyophilization to yield microparticles comprising an active agent. Altering the solvent conditions of such suspension to promote binding of the active agent to the particle is disclosed in U.S. Application No. 60/717,524; Ser. No. 11/532,063; and Ser. No. 11/532,065; U.S. Pat. No. 6,440,463; and U.S. application Ser. Nos. 11/210,709 and 11/208,087. Each of these patents and patent applications is incorporated by reference herein.

According to one embodiment, MMI-0100 (YARAAAR-QARAKALARQLGVAA; SEQ ID NO: 1) and its functional equivalents of the present invention can be dried by a method of spraying drying as disclosed in, for example, U.S. application Ser. No. 11/678,046 (incorporated by reference herein).

According to one embodiment, the polypeptide of the invention may be applied in a variety of solutions. A suitable formulation is sterile, dissolves sufficient amounts of the polypeptides, and is not harmful for the proposed application. For example, the compositions of the described invention may be formulated as aqueous suspensions wherein the active ingredient(s) is (are) in admixture with excipients suitable for the manufacture of aqueous suspensions.

Such excipients include, without limitation, suspending agents (e.g., sodium carboxymethylcellulose, methylcellulose, hydroxy-propylmethylcellulose, sodium alginate, polyvinylpyrrolidone, gum tragacanth, and gum acacia), dispersing or wetting agents including, a naturally-occurring phosphatide (e.g., lecithin), or condensation products of an alkylene oxide with fatty acids (e.g., polyoxyethylene stearate), or condensation products of ethylene oxide with long chain aliphatic alcohols (e.g., heptadecaethyl-eneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate).

Compositions of the described invention also may be formulated as oily suspensions by suspending the active ingredient in a vegetable oil (e.g., arachis oil, olive oil, sesame oil or coconut oil) or in a mineral oil (e.g., liquid paraffin). The oily suspensions may contain a thickening agent (e.g., beeswax, hard paraffin or cetyl alcohol). Compositions of the described invention also may be formulated in the form of dispersible powders and granules suitable for preparation of an aqueous suspension by the addition of water. The active ingredient in such powders and granules is provided in admixture with a dispersing or wetting agent, suspending agent, and one or more preservatives. Suitable dispersing or wetting agents and suspending agents are exemplified by those already mentioned above. Additional excipients also may be present.

According to one embodiment, the described invention provides administering the pharmaceutical composition to a subject. The step of administering comprises administering the composition orally, topically, parenterally, buccally, sublingually, by inhalation, or rectally.

According to one embodiment the administering step comprises administering the composition as a single dose post-injury.

According to one embodiment, the administering step comprises administering the composition orally. According to another embodiment, the administering step comprises administering the composition topically. According to another embodiment, the administering step comprises administering the composition parenterally. According to another embodiment, the administering step comprises administering the composition buccally. According to another embodiment, the administering step comprises administering the composition sublingually. According to another embodiment, the administering step comprises administering the composition by inhalation. According to another embodiment, the administering step comprises administering the composition rectally.

According to one embodiment, the composition is in the form of a tablet, a pill, a gel, an injectable solution, an aerosol, a troche, a lozenge, an aqueous suspension, an oily suspension, a dispersible powder, a granule, a bead, an emulsion, an implant, a cream, a patch, a capsule, a syrup, a suppository or an insert. According to one embodiment, the composition is in the form of a tablet. According to another embodiment, the composition is in the form of a pill. According to another embodiment, the composition is in the form of a gel. According to another embodiment, the composition is in the form of an injectable solution. According to another embodiment, the composition is in the form of an aerosol. According to another embodiment, the composition is in the form of a troche. According to another embodiment, the composition is in the form of a lozenge. According to another embodiment, the composition is in the form of an aqueous suspension. According to another embodiment, the composition is in the form an oily suspension. According to another embodiment, the composition is in the form of a dispersible powder. According to another embodiment, the composition is in the form of a granule. According to another embodiment, the composition is in the form of a bead. According to another embodiment, the composition is in the form of an emulsion. According to another embodiment, the composition is in the form of an implant. According to another embodiment, the composition is in the form of a cream. According to another embodiment, the composition is in the form of a patch. According to another embodiment, the composition is in the form of a capsule. According to another embodiment, the composition is in the form of a syrup. According to another embodiment, the composition is in the form of a suppository. According to another embodiment, the composition is in the form of an insert.

The compositions of the described invention can be administered orally, topically, parenterally, buccally, sublingually, by inhalation or insufflation (either through the mouth or through the nose), rectally, or by any means known to the skilled artisan. According to some embodiments, the composition of the described invention is a liquid solution, a suspension, an emulsion, a tablet, a pill, a capsule, a sustained release formulation, a delayed release formulation, a powder, or a suppository. The composition can be formulated with traditional binders and carriers such as triglycerides.

The composition can be administered in pharmaceutically acceptable solutions, which may routinely contain pharmaceutically acceptable concentrations of salt, buffering agents, preservatives, compatible carriers, adjuvants, and optionally other therapeutic agents.

The compositions of the described invention may be in a form suitable for oral use, for example, as tablets, troches, lozenges, aqueous or oily suspensions, dispersible powders or granules, emulsions, hard or soft capsules or syrups or elixirs. For oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like.

Moreover, when desired or needed, suitable binders, lubricants, disintegrating agents and coloring agents also may be incorporated in the mixture. Powders and tablets may be comprised of from about 5 to about 95 percent of the composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like.

Pharmaceutical compositions intended for oral use can be prepared according to any known method, and such compositions may contain one or more agents selected from the group consisting of sweetening agents, flavoring agents, coloring agents, and preserving agents in order to provide pharmaceutically elegant and palatable preparations.

Tablets may contain the active ingredient(s) in admixture with non-toxic pharmaceutically-acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch or alginic acid; binding agents, for example, starch, gelatin or acacia; and lubricating agents, for example, magnesium stearate, stearic acid or talc.

The tablets may be uncoated or they may be coated by known techniques, for example, to delay disintegration and absorption in the gastrointestinal tract and thereby provide a sustained action over a longer period, to protect the composition from oxidation or photodegradation; or for controlled release. For example, a time delay material such as glyceryl monostearate or glyceryl distearate can be employed.

Compositions of the described invention also may be formulated for oral use as hard gelatin capsules, where the active ingredient(s) is(are) mixed with an inert solid diluent, for example, calcium carbonate, calcium phosphate or kaolin, or soft gelatin capsules wherein the active ingredient(s) is (are) mixed with water or an oil medium, for example, peanut oil, liquid paraffin, or olive oil.

Liquid form preparations include solutions, suspensions and emulsions wherein the active ingredient(s) is (are) in admixture with excipients suitable for the manufacture of aqueous suspensions and emulsions. Such excipients are suspending agents, for example, sodium carboxymethylcellulose, methylcellulose, hydroxypropylmethylcellulose, sodium alginate, polyvinylpyrrolidone, gum tragacanth, and gum acacia; dispersing or wetting agents may be a naturally-occurring phosphatide such as lecithin, or condensation products of an alkylene oxide with fatty acids, for example, polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. As an example may be mentioned water or water-propylene glycol solutions for parenteral injections or addition of one or more coloring agents, one or more flavoring agents, and one or more sweetening agents, such as sucrose or saccharin and pacifiers for oral solutions, suspensions and emulsions.

Compositions of the described invention may be formulated as oily suspensions by suspending the active ingredient in a vegetable oil, for example arachis oil, olive oil, sesame oil or coconut oil, or in a mineral oil, such as liquid paraffin. The oily suspensions may contain a thickening agent, for example, beeswax, hard paraffin or cetyl alcohol. Sweetening agents, such as those set forth above, and flavoring agents may be added to provide a palatable oral preparation. These compositions can be preserved by the addition of an antioxidant such as ascorbic acid.

Compositions of the described invention may be formulated in the form of dispersible powders and granules suitable for preparation of an aqueous suspension by the addition of water. The active ingredient in such powders and granules is provided in admixture with a dispersing or wetting agent, suspending agent, and one or more preservatives. Suitable dispersing or wetting agents and suspending agents are exemplified by those already mentioned above. Additional excipients, for example, sweetening, flavoring and coloring agents also can be present.

The compositions of the invention also may be in the form of an emulsion. An emulsion is a two-phase system prepared by combining two immiscible liquid carriers, one of which is disbursed uniformly throughout the other and consists of globules that have diameters equal to or greater than those of the largest colloidal particles. The globule size must be such that the system achieves maximum stability. Usually, separation of the two phases will not occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil. Thus, the compositions of the invention may be in the form of an oil-in-water emulsion. The oily phase can be a vegetable oil, for example, olive oil or arachis oil, or a mineral oil, for example a liquid paraffin, or a mixture thereof. Suitable emulsifying agents may be naturally-occurring gums, for example, gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate. The emulsions also may contain sweetening and flavoring agents.

The compositions of the invention also may be formulated as syrups and elixirs. Syrups and elixirs may be formulated with sweetening agents, for example, glycerol, propylene glycol, sorbitol or sucrose. Such formulations also may contain a demulcent, a preservative, and flavoring and coloring agents. Demulcents are protective agents employed primarily to alleviate irritation, particularly mucous membranes or abraded tissues. A number of chemical substances possess demulcent properties. These substances include the alginates, mucilages, gums, dextrins, starches, certain sugars, and polymeric polyhydric glycols. Others include acacia, agar, benzoin, carbomer, gelatin, glycerin, hydroxyethyl cellulose, hydroxypropyl cellulose, hydroxypropyl methylcellulose, propylene glycol, sodium alginate, tragacanth, hydrogels and the like.

For buccal administration, the compositions of the described invention may take the form of tablets or lozenges formulated in a conventional manner.

There are three general methods of tablet preparation: the wet-granulation method; the dry-granulation method; and direct compression. The method of preparation and the added ingredients are selected to give the tablet formulation the desirable physical characteristics allowing the rapid compression of tablets. After compression, the tablets must have a number of additional attributes such as appearance, hardness, disintegration ability, appropriate dissolution characteristics, and uniformity, which also are influenced both by the method of preparation and by the added materials present in the formulation.

According to one embodiment, the tablet is a compressed tablet (CT). Compressed tablets are solid dosage forms formed with pressure and contain no special coating. Generally, they are made from powdered, crystalline, or granular materials, alone or in combination with binders, disintegrants, controlled-release polymers, lubricants, diluents and colorants. According to another embodiment, the tablet is a sugar-coated tablet. These are compressed tablets containing a sugar coating. Such coatings may be colored and are beneficial in covering up drug substances possessing objectionable tastes or odors and in protecting materials sensitive to oxidation. According to another embodiment, the tablet is a film-coated tablet. These Compressed tablets are covered with a thin layer or film of a water-soluble material. Numerous polymeric substances with film-forming properties may be used. According to another embodiment, the tablet is an enteric-coated tablet. These Compressed tablets are coated with substances that resist solution in gastric fluid but disintegrate in the intestine. According to another embodiment, the tablet is a multiple compressed tablet. These tablets are made by more than one compression cycle. Layered tablets are prepared by compressing additional tablet granulation on a previously compressed granulation. The operation may be repeated to produce multilayered tablets of two or three layers. Press-coated tablets (dry-coated) are prepared by feeding previously compressed tablets into a special tableting machine and compressing another granulation layer around the preformed tablets. According to another embodiment, the tablet is a controlled-release tablet. Compressed tablets can be formulated to release the drug slowly over a prolonged period of time. Hence, these dosage forms have been referred to as prolonged-release or sustained-release dosage forms. According to another embodiment, the tablet is a tablet for solution. These Compressed tablets may be used to prepare solutions or to impart given characteristics to solutions. According to some such embodiments, the tablet is an effervescent tablet. In addition to the drug, these tablets contain sodium bicarbonate and an organic acid such as tartaric acid or citric acid. In the presence of water, these additives react, liberating carbon dioxide that acts as a disintegrator and produce effervescence. According to another embodiment, the tablet is a buccal and or sublingual tablet. These are small, flat, oval tablets intended for buccal administration and that by inserting into the buccal pouch may dissolve or erode slowly. According to another embodiment, the tablet is a molded tablet or tablet triturate.

According to one embodiment, the tablet comprises a compressed core comprising at least one component of the described formulation and a membrane forming composition. Formulations utilizing membrane forming compositions are known to those of skill in the art (see, for example, Remington's Pharmaceutical Sciences, 20th Ed., 2000). Such membrane forming compositions may include, for example, a polymer, such as, but not limited to, cellulose ester, cellulose ether, and cellulose ester-ether polymers, an amphiphilic triblock copolymer surfactant, such as ethylene oxide-propylene oxideethylene oxide, and a solvent, such as acetone, which forms a membrane over the core. The compressed core may contain a bi-layer core including a drug layer and a push layer.

The term "non-oral administration" represents any method of administration in which a composition is not provided in a solid or liquid oral dosage form, wherein such solid or liquid oral dosage form is traditionally intended to substantially release and or deliver the drug in the gastrointestinal tract beyond the mouth and/or buccal cavity. Such solid dosage forms include conventional tablets, capsules, caplets, etc., which do not substantially release the drug in the mouth or in the oral cavity. It is appreciated that many oral liquid dosage forms such as solutions, suspensions, emulsions, etc., and some oral solid dosage forms may release some of the drug in the mouth or in the oral cavity during the swallowing of these formulations. However, due to their very short transit time through the mouth and the oral cavities, the release of drug from these formulations in the mouth or the oral cavity is considered de minimis or insubstantial. Accordingly, it is understood that the term "non-oral" includes parenteral, transdermal, inhalation, implant, and vaginal or rectal formulations and administrations. Further, implant formulations are to be included in the term "non-oral," regardless of the physical location of implantation. Particularly, implantation formulations are known which are specifically designed for implantation and retention in the gastrointestinal tract. Such implants are also considered to be non-oral delivery formulations, and therefore are encompassed by the term "non-oral."

The compositions of the described invention may be in the form of suppositories for rectal administration of the composition, such as for treating pediatric fever. The terms "rectal" or "rectally" as used herein refer to introduction into the body through the rectum where absorption occurs through the walls of the rectum. These compositions can be prepared by mixing the drug with a suitable nonirritating excipient such as cocoa butter and polyethylene glycols which are solid at ordinary temperatures but liquid at the rectal temperature and will therefore melt in the rectum and release the drug. When formulated as a suppository the compositions of the invention may be formulated with traditional binders and carriers, such as triglycerides.

According to one embodiment, the tablet is a compressed suppository or insert. For preparing suppositories, a low melting wax such as a mixture of fatty acid glycerides, such as cocoa butter, is first melted, and the active ingredient is dispersed homogeneously therein by stirring or similar mixing. The molten homogeneous mixture is then poured into convenient sized molds, allowed to cool and thereby solidify.

The compositions of the described invention may be in the form of a sterile injectable aqueous or oleaginous suspension. Injectable preparations, such as sterile injectable aqueous or oleaginous suspensions, may be formulated according to the known art using suitable dispersing or wetting agents and suspending agents.

The sterile injectable preparation may also be a sterile injectable solution or suspension in a nontoxic parenterally acceptable diluent or solvent, for example, as a solution in 1,3-butanediol. A solution generally is considered as a homogeneous mixture of two or more substances; it is frequently, though not necessarily, a liquid. In a solution, the molecules of the solute (or dissolved substance) are uniformly distributed among those of the solvent. A suspension is a dispersion (mixture) in which a finely-divided species is combined with another species, with the former being so finely divided and mixed that it does not rapidly settle out. In everyday life, the most common suspensions are those of solids in liquid water. Among the acceptable vehicles and solvents that may be employed are water, Ringer's solution, and isotonic sodium chloride solution. In addition, sterile, fixed oils are conventionally employed as a solvent or suspending medium. For parenteral application, particularly suitable vehicles consist of solutions, preferably oily or aqueous solutions, as well as suspensions, emulsions, or implants. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension also may contain suitable stabilizers or agents, which increase the solubility of the compounds to allow for the preparation of highly concentrated solutions. Alternatively, the active compounds may be in powder form for constitution with a suitable vehicle, e.g., sterile pyrogen-free water, before use.

The active agent, when it is desirable to deliver it locally, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form.

The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Suitable liquid or solid pharmaceutical preparation forms are, for example, microencapsulated, and if appropriate, with one or more excipients, encochleated, coated onto microscopic gold particles, contained in liposomes, pellets for implantation into the tissue, or dried onto an object to be rubbed into the tissue. Such pharmaceutical compositions also may be in the form of granules, beads, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, or solubilizers are customarily used as described above. The pharmaceutical compositions are suitable for use in a variety of drug delivery systems. For a brief review of methods for drug delivery, see Langer 1990 Science 249, 1527-1533, which is incorporated herein by reference.

Injectable depot forms are made by forming microencapsulated matrices of a described inhibitor in biodegradable polymers such as polylactide-polyglycolide. Depending upon the ratio of inhibitor to polymer and the nature of the particular polymer employed, the rate of drug release may be controlled. Such long acting formulations may be formulated with suitable polymeric or hydrophobic materials (for example, as an emulsion in an acceptable oil) or ion exchange resins, or as sparingly soluble derivatives, for example, as a sparingly soluble salt. Examples of other biodegradable polymers include poly(orthoesters) and poly(anhydrides). Depot injectable formulations also are prepared by entrapping the inhibitor of the described invention in liposomes or microemulsions, which are compatible with body tissues.

The locally injectable formulations may be sterilized, for example, by filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono- or diglycerides. In addition, fatty acids such as oleic acid are used in the preparation of injectables.

Formulations for parenteral administration include aqueous and non-aqueous sterile injection solutions that may contain anti-oxidants, buffers, bacteriostats and solutes, which render the formulation isotonic with the blood of the intended recipient; and aqueous and non-aqueous sterile suspensions, which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

The pharmaceutical agent or a pharmaceutically acceptable ester, salt, solvate or prodrug thereof may be mixed with other active materials that do not impair the desired action, or with materials that supplement the desired action. Solutions or suspensions used for parenteral, intradermal, subcutaneous, intrathecal, or topical application may include, but are not limited to, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation may be enclosed in ampoules, disposable syringes or multiple dose vials made of glass or plastic. Administered intravenously, particular carriers are physiological saline or phosphate buffered saline (PBS).

The compositions of the described invention may be in the form of a dispersible dry powder for delivery by inhalation or insufflation (either through the mouth or through the nose). Dry powder compositions may be prepared by processes known in the art, such as lyophilization and jet milling, as disclosed in International Patent Publication No. WO 91/16038 and as disclosed in U.S. Pat. No. 6,921,527, the disclosures of which are incorporated by reference. The composition of the described invention is placed within a suitable dosage receptacle in an amount sufficient to provide a subject with a unit dosage treatment. The dosage receptacle is one that fits within a suitable inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. Nos. 4,227,522; 4,192,309; and 4,105,027. Suitable containers also include those used in conjunction with Glaxo's Ventolin® Rotohaler brand powder inhaler, Fison's Spinhaler® brand powder inhaler. Another suitable unit-dose container which provides a superior moisture barrier is formed from an aluminum foil plastic laminate. The pharmaceutical-based powder is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler® (U.S. Pat. Nos. 4,627,432; 4,811,731; and 5,035,237). According to one embodiment, a MicroDose Dry Powder Inhaler (DPI) comprising a piezoelectric vibrator to deaggregate the drug powder packaged in either moisture-resistant aluminum or plastic blisters, which are pierced with small needles prior to dosing to create openings into the flow channel of the device is employed. (MicroDose DPI Drug Delivery, www.ondrugdelivery, Ltd., pp. 26-29 (August 2007). Each of these references is incorporated herein by reference.

The compositions of the described invention also may be deliverable transdermally. The transdermal compositions may take the form of creams, lotions, aerosols and/or emulsions and can be included in a transdermal patch of the matrix or reservoir type as are conventional in the art for this purpose. The term "topical" refers to administration of an inventive composition at, or immediately beneath, the point of application. The phrase "topically applying" describes application onto one or more surfaces(s) including epithelial surfaces.

Topical administration may also involve the use of transdermal administration such as transdermal patches or iontophoresis devices which are prepared according to techniques and procedures well known in the art. The terms "transdermal delivery system", transdermal patch" or "patch" refer to an adhesive system placed on the skin to deliver a time released dose of a drug(s) by passage from the dosage form through the skin to be available for distribution via the systemic circulation. Transdermal patches are a well-accepted technology used to deliver a wide variety of pharmaceuticals, including, but not limited to, scopolamine for motion sickness, nitroglycerin for treatment of angina pectoris, clonidine for hypertension, estradiol for postmenopausal indications, and nicotine for smoking cessation. Patches suitable for use in the described invention include, but are not limited to, (1) the matrix patch; (2) the reservoir patch; (3) the multi-laminate drug-inadhesive patch; and (4) the monolithic drug-in-adhesive patch; TRANSDERMAL AND TOPICAL DRUG DELIVERY SYSTEMS, pp. 249-297 (Tapash K. Ghosh et al. eds., 1997), hereby incorporated herein by reference. These patches are well known in the art and generally available commercially.

The compositions of the described invention may further include conventional excipients, i.e., pharmaceutically acceptable organic or inorganic carrier substances suitable for parenteral application which do not deleteriously react with the active compounds. Suitable pharmaceutically acceptable carriers include, but are not limited to, water, salt solutions, alcohol, vegetable oils, polyethylene glycols, gelatin, lactose, amylose, magnesium stearate, talc, silicic acid, viscous paraffin, perfume oil; fatty acid monoglycerides and diglycerides, petroethral fatty acid esters, hydroxymethylcellulose, polyvinylpyrrolidone, etc.

The compositions may be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, suitable vehicles include solutions, such as oily or aqueous solutions, as well as suspensions, emulsions, or implants. Aqueous suspensions may contain substances which increase the viscosity of the suspension and include, for example, but not limited to, sodium carboxymethyl cellulose, sorbitol and/or dextran. Optionally, the suspension also may contain stabilizers. These compositions also may contain adjuvants including preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It also may be desirable to include isotonic agents, for example, sugars, sodium chloride and the like. Prolonged absorption of the injectable pharmaceutical form may be brought about by the use of agents delaying absorption, for example, aluminum monostearate and gelatin.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

The composition, if desired, also may contain minor amounts of wetting or emulsifying agents or pH buffering agents. Oral formulations can include standard carriers such as pharmaceutical grades of mannitol, lactose, starch, magnesium stearate, sodium saccharine, cellulose, magnesium carbonate, etc. Examples of suitable buffering agents include, without limitation: acetic acid and a salt (1%-2% w/v); citric acid and a salt (1%-3% w/v); boric acid and a salt (0.5%-2.5% w/v); and phosphoric acid and a salt (0.8%-2% w/v). Suitable preservatives include benzalkonium chloride (0.003%-0.03% w/v); chlorobutanol (0.3%-0.9% w/v); parabens (0.01%-0.25% w/v) and thimerosal (0.004%-0.02% w/v).

The pharmaceutical compositions within the described invention contain a therapeutically effective amount of an MK2 inhibitor compound and optionally other therapeutic agents included in a pharmaceutically-acceptable carrier. The components of the pharmaceutical compositions also are capable of being commingled in a manner such that there is no interaction which would substantially impair the desired pharmaceutical efficiency.

The therapeutically effective amount of the MK2 inhibitor compound may be provided in particles. The particles may contain the therapeutic agent(s) in a core surrounded by a coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, etc., and any combination thereof. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules that contain the therapeutic agent(s) in a solution or in a semi-solid state. The particles may be of virtually any shape.

Both non-biodegradable and biodegradable polymeric materials may be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels as described by Sawhney et al in Macromolecules (1993) 26, 581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. In order to prolong the effect of a drug, it often is desirable to slow the absorption of the drug from subcutaneous, intrathecal, or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Use of long-term sustained release formulations may be particularly suitable for treatment of chronic conditions. Long-term sustained release formulations are well-known to those of ordinary skill in the art and include some of the release systems described above.

Depending upon the structure, the MK2 inhibitor compound, and optionally at least one other therapeutic agent, may be administered per se (neat) or, depending upon the structure of the inhibitor, in the form of a pharmaceutically acceptable salt. The MK2 inhibitor compound may form pharmaceutically acceptable salts with organic or inorganic acids, or organic or inorganic bases. When used in medicine the salts should be pharmaceutically acceptable, but non-pharmaceutically acceptable salts conveniently may be used to prepare pharmaceutically acceptable salts thereof.

By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zurich, Switzerland: 2002).

The salts may be prepared in situ during the final isolation and purification of the compounds described within the present invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides, such as methyl, ethyl, propyl, and butyl chlorides, bromides and iodides; dialkyl sulfates like dimethyl, diethyl, dibutyl and diamyl sulfates; long chain halides, such as decyl, lauryl, myristyl and stearyl chlorides, bromides and iodides; arylalkyl halides, such as benzyl and phenethyl bromides, and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts may be also obtained using standard procedures well known in the art, for example by reacting with a sufficiently basic compound such as an amine with a suitable acid affording a physiologically acceptable anion. Alkali metal (for example, sodium, potassium or lithium) or alkaline earth metal (for example calcium or magnesium) salts of carboxylic acids may also be made.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which can independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning The publications discussed herein are provided solely for their disclosure prior to the filing date of the present application. Nothing herein is to be construed as an admission that the described invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g., amounts, temperatures, etc.) but some experimental errors and deviations should be accounted for. Unless indicated otherwise, parts are by weight, molecular weight is weight average molecular weight, temperature is in degrees Centigrade, and pressure is at or near atmospheric.

Materials and Methods

MMI-0100 Drug Development

For synthesis of MMI-0100 (YARAAARQARAKALARQLGVAA; SEQ ID NO: 1), approximately 1 kg of Fmoc-Ala-Wang Resin was transferred into a 50 L glass solid phase synthesis reaction vessel equipped with a mechanical stirrer. The resin was allowed to swell in dimethylformide (DMF) for no less than (NLT) 2 hours before draining the DMF. The resin beads then were washed with consecutive rinses of DMF. The N-terminal protecting group (i.e. Fmoc) was removed (de-blocking step) by treatment with 20% piperidine in DMF and the resin was washed with DMF. The next amino acid in the sequence was coupled in the presence of 1-hydroxybenzotriazole (HOBt) and diisopropylcarbodiimide (DIC). Generally, 2.5-3.5 molar equivalents of Fmoc-amino acid (Fmoc-AA) to the synthesis scale were used for coupling. The Fmoc-AA was dissolved in DMF and activated by the addition of HOBt and DIC. The completion of each coupling was monitored by the Ninhydrin test. If a coupling was incomplete, a second coupling with the same amino acid was performed by using the symmetrical anhydride method. Generally, 3.0-6.0 molar equivalents of Fmoc-AA to the synthesis scale were used for coupling. The Fmoc-AA was dissolved in dichloromethane (DCM) and a minimal volume of DMF and activated through the addition of DIC in a molar ratio of Fmoc-AA/DIC=1.0/0.5. When the full peptide sequence was completed, the peptide resin was rinsed thoroughly with successive washes of DMF and MeOH. The resin then was dried under vacuum for NLT 3 hours. Typical recovery of the total dried peptide resin was approximately 2,800 grams, representing a peptide resin yield of ~65%.

Approximately 370-500 grams of peptide resin then were transferred into a suitably sized glass bottle equipped with a magnetic stir bar. The flask containing the peptide resin was cooled in an ice/water bath or in a refrigerator for no longer than 30 minutes. The trifluoroacetic acid (TFA) cocktail (a mixture of TFA, TIS, and water in the ratio of 95 mL:2.5 mL:2.5 mL) was pre-chilled in an ice/water bath for no longer than 30 minutes. Approximately 8-12 mL of TFA cleavage cocktail per gram of resin was added to this vessel. As soon as the peptide resin and TFA cocktail were combined, the ice/water bath was removed and the reaction mixture was stirred at room temperature for 2-3 hours. The reaction mixture then was filtered through a coarse glass filter and the resin was washed two times with 0.5-1.0 mL of TFA per gram of resin per wash. The combined filtrate was collected and the resin was discarded. The filtrate was then added to ether that was pre-chilled in a refrigerator for less than 30 minutes, in a ratio of 1 mL of filtrate per 10 mL ether, to precipitate the cleaved peptide. The peptide-ether mixture was equilibrated to room temperature for no longer than 30 minutes. The precipitated peptide was collected on a medium glass filter. The precipitate was washed thoroughly with cold ether three times, using enough ether to at least cover all the precipitate on the filter. The ether then was eluted through the same medium glass filter. The crude peptide was transferred into a plastic bottle and was placed in a desiccator connected to a mechanical vacuum pump to dry for no later than 12 hours. After drying, the crude peptide was stored at 5±3° C. The cleavage procedure was repeated multiple times until all the peptide resin was cleaved. A typical batch recovery of total dried crude peptide was approximately 1,250 grams, representing a cleavage yield of approximately 110%.

The crude peptide from cleavage was prepared for high-performance liquid chromatography (HPLC) purification by dissolving the peptide in HPLC buffer at a final crude peptide concentration of 20 mg/mL. The peptide solution was filtered through a 1 μm glass filter membrane and loaded onto a C18 reverse phase column, which was operated by a preparative HPLC system. The column was washed and equilibrated. A linear gradient was used to elute the crude peptide from the column. Following each crude purification, the fractions were analyzed by an analytical HPLC system using a Kromasil C18, 5 μm, 100 Å 4.6×250 mm column. Fractions generated from the initial purification were pooled based on the HPLC purity and impurity profile of each fraction. Peptide pools were stored at 2-8° C. until further processing. This process was repeated until all of the crude peptide was purified through the HPLC column and met the Main Pool purity criteria. A salt exchange to acetate salt was performed by HPLC. The final peptide solution was filtered through a 0.22 μm filter and loaded onto a tray lyophilizer. The peptide was pre-frozen at 40° C. for no longer than 720 minutes before starting the lyophilization cycle. The lyophilization took approximately 5 days. Approximately 50-55% final yield resulted from the purification and lyophilization steps.

Cell Permeant Peptide Synthesis and Delivery.

The MMI-0100 peptide (MW=2283.67 g/mol; YARAAARQARAKALARQLGVAA; SEQ ID NO: 1) was synthesized using standard Fmoc chemistry as previously described [Ward B, Seal B L, Brophy C M, Panitch A. Design of a bioactive cell-penetrating peptide: when a transduction domain does more than transduce. J Peptide Sci. 2009; 15:668-74]. MMI-0100 was prepared and delivered daily intraperitoneally in PBS (50 μg/kg), as previously described [Vittal R, Fisher A, Gu H, Mickler E A, Panitch A, Lander C, et al. Peptide-mediated Inhibition of MK2 Ameliorates Bleomycin-Induced Pulmonary Fibrosis. Am J Respir Cell Mol Biol. 2013]. In cell line studies, the peptide was dissolved in DMSO before adding to the cell media (final [0.5%] to target peptide intracellularly), as previously described [Ward B C, Kavalukas S, Brugnano J, Barbul A, Panitch A. Peptide inhibitors of MK2 show promise for inhibition of abdominal adhesions. The Journal of surgical research. 2011; 169:e27-36], to give a final MMI-0100 concentration of 20 μM or 100 μm.

Animals and Myocardial Infarction (MI) Model.

Eight to ten week old C57BL/6 mice (25-30 g) were obtained from Charles River (Wilmington, Mass.) and maintained for at least 7 days with free access to standard rodent food and water. Myocardial infarction was induced by permanent ligation of the left anterior descending (LAD) coronary artery as described previously [Maejima Y, Kyoi S, Zhai P, Liu T, Li H, Ivessa A, et al. Mst1 inhibits autophagy by promoting the interaction between Beclin1 and Bcl-2. Nature Medicine. 2013; 19:1478-88; Qian L, Huang Y, Spencer C I, Foley A, Vedantham V, Liu L, et al. In vivo reprogramming of murine cardiac fibroblasts into induced cardiomyocytes. Nature. 2012; 485:593-8]. Post-surgery, mice were immediately treated with lidocaine (6 mg/kg IM) and atropine (0.04-0.10 mg/kg IM) upon surgical closure, followed by lidocaine and atropine every 2-4 hours for the first 24 hours to prevent arrhythmias. Post-anesthesia, mice were given 0.1 mg/kg buprenorphine every 12 hours for the first 48 hours. Within the first hour post-MI, 50 μg/kg/day MMI-0100 peptide (or PBS control) was given intraperitoneally and repeated for a total of 14 days. In parallel, control groups underwent: 1) a sham operation that included every step except the coronary artery ligation; 2) Daily MMI-0100 intraperitoneally for 14 days. Cardiac function was measured by conscious echocardiography using a Vevo 2100 ultrasound biomicrscopy system (VisualSonics, Inc., Toronto, Canada) at baseline, 1, 7, and 14 days, as previously described [Oakley R H, Ren R, Cruz-Topete D, Bird G S, Myers P H, Boyle M C, et al. Essential role of stress hormone signaling in cardiomyocytes for the prevention of heart disease. Proc Natl Acad Scie USA. 2013; 110:17035-40; Willis M S, Homeister J W, Rosson G B, Annayev Y, Holley D, Holly S P, et al. Functional redundancy of SWI/SNF catalytic subunits in maintaining vascular endothelial cells in the adult heart. Circulation Res. 2012; 111:e111-22; Willis M S, Schisler J C, Li L, Rodriguez J E, Hilliard E G, Charles P C, et al. Cardiac muscle ring finger-1 increases susceptibility to heart failure in vivo. Circulation Res. 2009; 105:80-8].

Histological Analysis of Fibrosis.

Mice were euthanized by isoflurane and cervical dislocation at day 14, fixed in fresh 4% paraformaldehyde for 24 hours, paraffin embedded, processed, and stained with standard hematoxylin and eosin (H&E) and Masson's trichrome (MT). Starting at the ligation with fully faced tissue, 14-15 levels were cut on each block at 50 μm (one slide for H&E, one for MT, and 3 unstained; 50 μm skipped and then repeated). Controls were similarly cut starting at a comparable level. The area of fibrosis was analyzed in 3-4 blindly chosen hearts, each heart at 14-15 levels (point of ligation to apex), 3 sections at each level. Analysis of collagen was performed blinded to treatment on these 42-45 sections per heart. Slides were scanned using an Aperio Scanscope (Aperio Technologies, Vista, Calif.) and analyzed using Aperio Imagescope. The Algorithm Positive Pixel Count v9 was used to measure the Masson's trichrome staining of collagen (representing both fibrosis and collagen in extracellular matrix), hue value (0.66) and hue width (0.1) were used analyzed the tissue outlined using the pen tool. Each section was analyzed and exported. The N positive/N total value (representing the % collagen of the entire section) was used to determine a weighted average for each slide.

Cell Culture of Primary Cardiac Fibroblast Cells and Cardiomyocyte Cell Lines.

H9C2 is a myoblast cell line derived from rat myocardium obtained from ATCC® (CRL-1446, ATCC, Manassas, Va.) and cultured according to the recommended protocols. Briefly, cells were maintained at 37° C. with 5% $CO_2$ in DMEM supplemented with 10% fetal bovine serum and antibiotics (100 U/ml penicillin, 100 mg/ml streptomycin) and split at a ratio of 1:4 using 0.05% trypsin every 36 hours. HL-1 cells were obtained from Dr. William Claycomb and cultured according to the published protocols [Claycomb W C, Lanson N A, Jr., Stallworth B S, Egeland D B, Delcarpio J B, Bahinski A, et al. HL-1 cells: a cardiac muscle cell line that contracts and retains phenotypic characteristics of the adult cardiomyocyte. Proc. Natl Acad. Sci. USA. 1998; 95:2979-84; White S M, Constantin P E, Claycomb W C. Cardiac physiology at the cellular level: use of cultured HL-1 cardiomyocytes for studies of cardiac muscle cell structure and function. Am. J. Physiol. Heart Circul. Physiol. 2004; 286:H823-9]. Briefly, cells were cultured in Claycomb medium (JRH Biosciences, USA) supplemented with 10% fetal bovine serum (JRH Biosciences), 2 mM L-glutamine (Gibco, Grand Island, N.Y.), 100 μM norepinephrine (Sigma, USA), 100 U/mL penicillin, and 100 μg/mL streptomycin (Gibco) in flasks precoated with fibronectin and gelatin (Sigma), then incubated at 37° C. in 5% CO2. Cells were split at a ratio of 1:4 using 0.05% trypsin every 48 hours. Primary cardiac fibroblasts were obtained from 2-4-day-old Sprague Dawley rats, according to previously described protocols (cat. #L K003300, Worthington Biochemical Corp., Lakewood, N.J.) [Toraason M, Luken M E, Breitenstein M, Krueger J A, Biagini R E. Comparative toxicity of allylamine and acrolein in cultured myocytes and fibroblasts from neonatal rat heart. Toxicology. 1989; 56:107-17; LaFramboise W A, Scalise D, Stoodley P, Graner S R, Guthrie R D, Magovern J A, et al. Cardiac fibroblasts influence cardiomyocyte phenotype in vitro. Am. J. Physiol. Cell Physiol. 2007; 292:C1799-808]. Harvested fibroblasts were seeded in 10 cm FALCON polystyrene dishes (B D Biosciences), and incubated for 45 min in DMEM with 10% fetal bovine serum and antibiotics. Cardiomyocytes that did not attach to the noncoated plates were rinsed away and the remaining fibroblasts were given fresh medium, grown to confluence, trypsinized (0.05%) and passaged twice before being used in experiments.

Induction of Hypoxia and Determination of Cell Death In Vitro and Effects of MMI-0100 Given at the Start of Ischemia Time.

Cells were rinsed in PMS and grown in DMEM (cat. #11966-025, Gibco) for 2 hours prior to initiating hypoxia (simulated ischemia). Hypoxia was induced by placing cells in a hypoxia chamber (HERACELL 150i, Thermo Scientific) in a mixture of 5% $CO_2$/95% $N_2$ to attain a 1% oxygen concentration, according to the manufacturer's instruction. Three experimental groups were tested for each cell type: 1) Final[0.5% DMSO; Negative Control]; 2) 20 μM MMI-0100 peptide [in a final 0.5% DMSO]; and 3) 100 μM MMI-0100 peptide [in a final 0.5% DMSO] at 3 time points. The MMI-0100 peptide was added to the cells at the start of the ischemia time. Cells were cultured in 12 well plates. At the time of performing the experiments, all cultures were approximately 70-90% confluent. Three different time points were adopted for each of the three cell lines according to the severity of cell death under hypoxia determined by LDH release: for H9C2 cell line: 8 hr; 16 hr; 24 hr; for HL-1 cell line: 4 hr; 8 hr; 12 hr; for cardiac fibroblast cell line: 16 hr; 32 hr; 48 hr.

Cell death was first determined using an LDH release assay (cat. #630117, Clontech), according to the manufacturer's instructions. Briefly, after MMI-0100 peptide treatment and challenge with hypoxia (or normoxia controls) conditions, 100 μl of culture media was assayed for LDH release using LDH assay kits; in parallel 100 μl of the Catalyst and the Dye were assayed and read at 490 nm (CLARIOstar, BMG LABTECH GmbH, Ortenberg, Germany). All data was run in triplicate and presented as a percentage of parallel cells treated with a final of 1% Triton-X-100. Caspase 3/7 activity was next determined using a commercial Caspase 3/7 activity kit (Cat. #G8091, Promega, Madison, Wis. 53711) in a 384 well plate (Cat. #781903, Greiner bio-one) according to the manufacturer's instructions. Briefly, cells were harvested in 35 μl ice cold Passive Lysis Buffer (cat. #E194A, Promega), rocked for 5 min at RT, then stored at −80 C. The resulting cell lysates were centrifuged at 10,000×g for 10 min. The resulting cell lysates (25 μl, with 0.6 ug total protein) and Caspase-Glo 3/7 Reagent were added to each well in a 1:1 ratio and the luminescence was read (CLARIOstar, BMG LABTECH GmbH).

Immunoblot Analysis of MK2 Activity.

The left over cell lysates from the Caspase activity assay were used for the Western blots. Cell lysate was first fractionated by SDS-4-10% polyacrylamide gel electrophoresis and transferred to PVDF membranes (cat. #162-0177, Bio-Rad, Berkeley, Calif.). After blocking with recommended blocking reagents for 1 h at the room temperature, the membranes were incubated overnight at 4° C. with primary antibodies in TBS-T, and then incubated with secondary antibodies conjugated with HRP in TBS-T. HNRNPA0, MAPK2, and phospho-MAPK2 proteins were detected using anti-HNRNPA0 (cat. #HPA036569, 1:1000, Sigma-Aldrich), anti-MAPKAPK2 (cat. #SAB4300553, Sigma-Aldrich), and anti-phospho-MAPKAPK2 (cat. #SAB4300241, 1:1000, Sigma-Aldrich). As a loading control, β-actin was detected using anti-βactin (cat. #A2228, 1:6000, Sigma-Aldrich). Goat anti-rabbit IgG (whole molecule)—Peroxidase antibody (cat. #A9169, 1:1000, Sigma-Aldrich) anti-Mouse IgG (Fab specific)—Peroxidase antibody produced in goat (cat. #A9917, 1:6000, Sigma-Aldrich) were used as secondary antibodies. Lumigen ECL Ultra (cat. #TMA-100, Lumigen, Southfield, Mich.) chemiluminescence was detected using the BioSpectrum Imaging System (Biospectrum 510, UVP, Upland, Calif.). Quantity One 1-D Analysis Software (cat. #170-9600, Bio-Rad Laboratories, Inc., Hercules, Calif.) was utilized for densitometry analysis.

Cytokine Analysis of Cell Media for TNFα, IL-1β, and IL-6.

Cytokine analysis to detect TNFα, IL-1β, and IL-6 was performed for either mouse (HL1) or rat (H9C2 and primary cardiac fibroblasts) using Luminex multiplex assays (LUM000, LUM401, LUM406, LUM410, LUR000, LUR401, LUR406, LUR410, R&D Systems, Inc., Minneapolis, Minn.) run on a Bio-Plex 200 (Bio-Rad, Hercules, Calif.) according to manufacturer's protocol. Standard curves were run in parallel with each experiment.

Statistical Analysis.

SigmaPlot (Systat Software, Inc., San Jose, Calif.) was used to determine significant statistical differences using a Log-rank (Mantel-Cox) test to determine differences in survival or a Kruskal-Wallis one-way ANOVA for both in vivo and in vitro studies at each terminal time point in experiments run in parallel. If significance was reached ($p<0.05$), a post-hoc all pairwise Multiple Comparison Procedures (Tukey Test) was performed between each of the groups to determine significance. Significance was defined as $p<0.05$.

Example 1: Treatment of Acute MI with MMI-0100 Peptide Improves Cardiac Function and Heart Failure Measures In Vivo In this study, acute myocardial infarction (AMI) was induced in eight to ten week old C57BL/6 mice by permanent ligation of the left anterior descending (LAD) coronary artery in order to determine whether treatment of AMI with MMI-0100 peptide can improve cardiac function and heart failure measures in vivo.

Figure 1A:
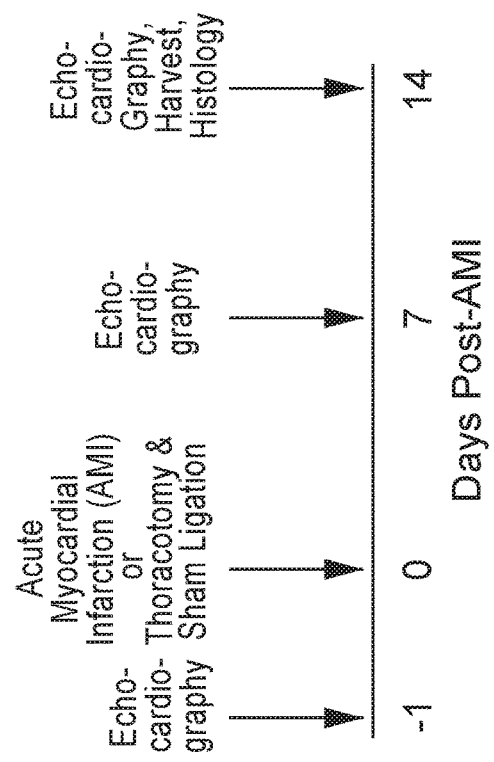
Figure 9B:
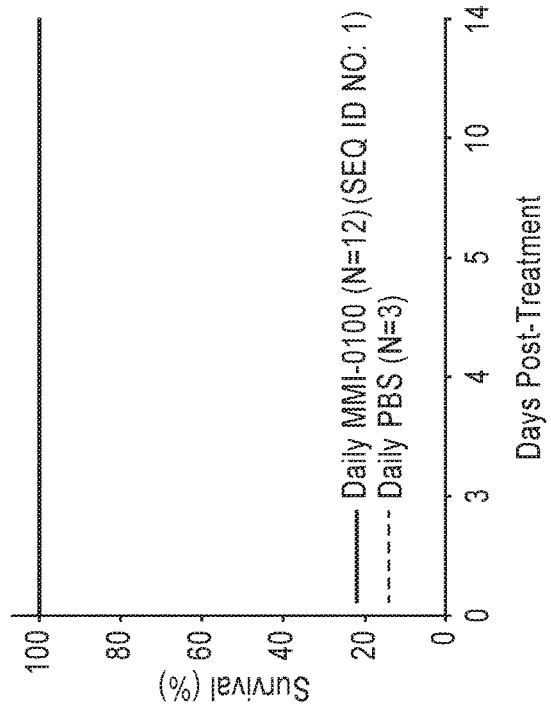
FIGS. 9A-B show survival analysis after permanent LAD coronary artery ligation and after 50 µg/kg/day MMI-0100 peptide in PBS intraperitoneal injection.
Figure 9A:
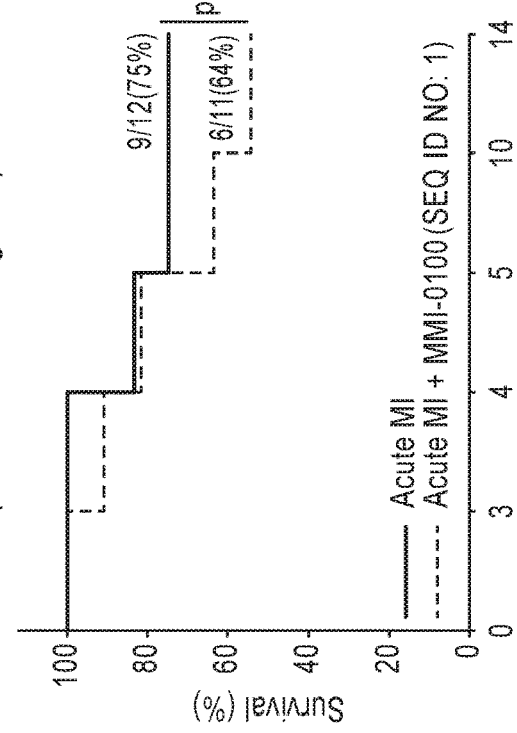

Echocardiography was used to follow cardiac function and morphometry prior to the surgical induction of an acute myocardial infarction (AMI) induced by thoracotomy and ligation of the left anterior descending coronary artery in C57BL/6 mice. Cardiac function was then followed at 7 and 14 days post-AMI (FIG. 1A). Mice were separated into three groups: (1) AMI treated with MMI-0100; (2) AMI untreated; and (3) a control group that underwent thoracotomy and sham ligation. Thirty minutes after the complete permanent LAD occlusion, the first dose of MMI-0100 was given at the previously established dose (50 mg/kg given daily [Muto A, Panitch A, Kim N, Park K, Komalavilas P, Brophy C M, et al Inhibition of Mitogen Activated Protein Kinase Activated Protein Kinase II with MMI-0100 reduces intimal hyperplasia ex vivo and in vivo. Vascular Pharmacol. 2012; 56:47-55]), illustrated in FIG. 1B. As expected, not all mice survived the AMI procedure, but no differences in survival were seen after AMI either with or without the MMI-0100 treatment (FIG. 9A).

Figure 1C:
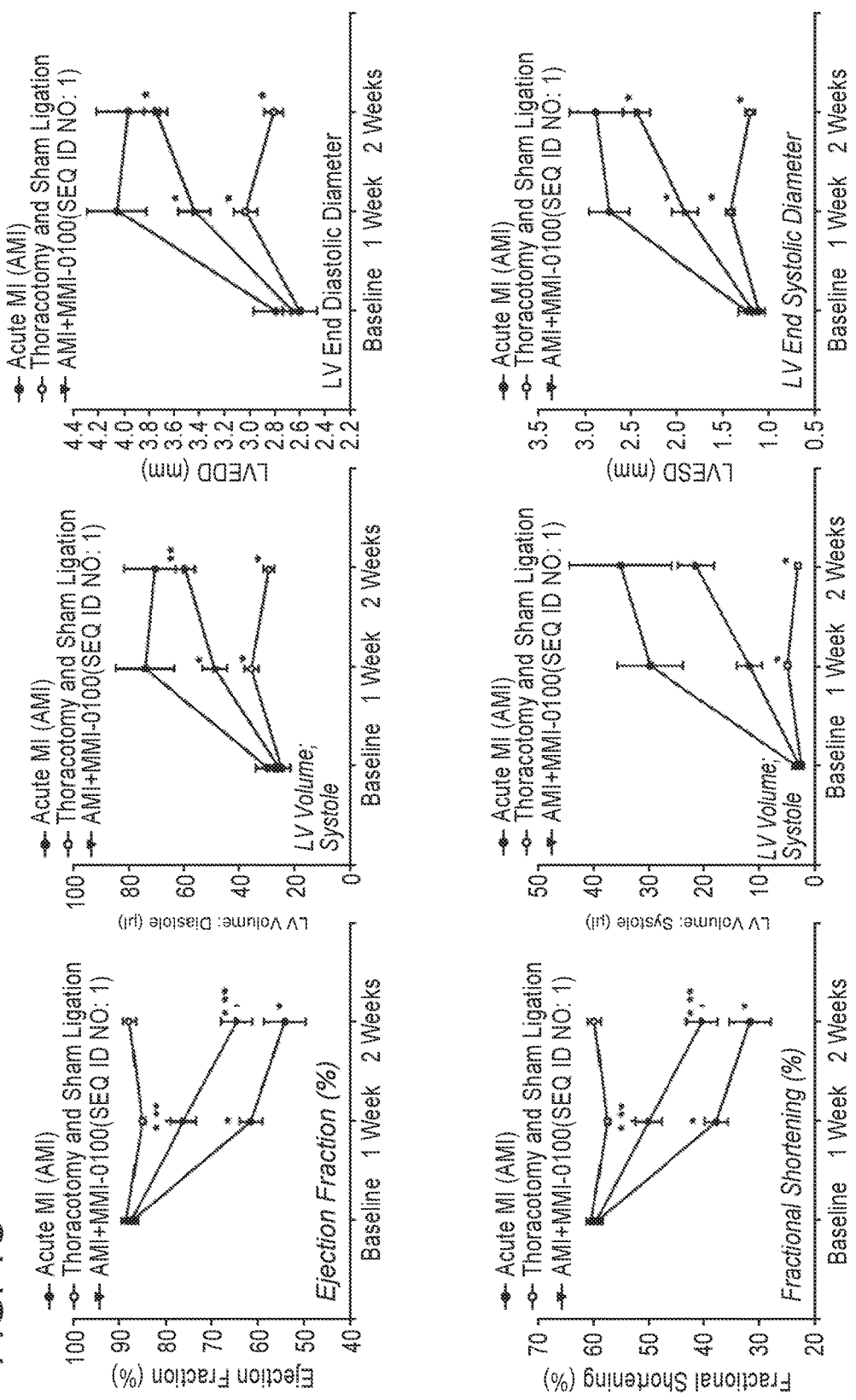

Cardiac function of mice in the AMI group had an ejection fraction depressed 25.9% ((87.6−64.9)/87.6*100) and fractional shortening depressed 36.6% ((55.7−35.3/55.7*100) after 2 weeks (FIG. 1C, left) compared to sham-operated control mice. Dilation of left ventricle, measured by left ventricular (LV) volume and LV end diastolic diameter was found at 1 week and plateaued at 2 weeks when compared to sham operated control mice (decreased 130% and 88.7% respectively) (FIG. 1C, middle & right columns). AMI mice treated with MMI-0100 demonstrated significant improvement compared to untreated AMI mice, having significantly greater function at 1 and 2 weeks after AMI, which translated into a decreased LV dilation (LVID; d decreased 29% (vs. 40% without MMI-0100) and LV Volume; d decreased 88% (vs. 130% without MMI-0100 (FIG. 1C). Representative M-mode echocardiographic images of all three groups are shown in FIG. 1D; fully quantified in Table 2. Treatment of mice with MMI-0100 alone did not have any effect on cardiac function (Table 3) or survival (FIGS. 9A-B).

Example 2: Treatment of Acute MI with MMI-0100 Treatment Decreases Cardiac Fibrosis In Vivo Myocardial infarction triggers an inflammatory reaction that results in the formation of a scar. Healing from myocardial infarction is associated with alterations in the left ventricle, including dilation and hypertrophy [Bujak M, Frangogiannis N G. The role of TGF-beta signaling in myocardial infarction and cardiac remodeling. Cardiovascular research. 2007; 74:184-95]. In the early stages of an acute MI, TGF-β has been proposed to play a role in deactivating macrophages and suppressing endothelial cell cytokine synthesis [Bujak M, Frangogiannis N G. The role of TGF-beta signaling in myocardial infarction and cardiac remodeling. Cardiovascular research. 2007; 74:184-95]. In later stages, TGF-β activates fibroblasts to deposit extracellular matrix (collagen) which contributes to left ventricular remodeling by promoting fibrosis in the non-infarcted myocardium, in addition to the myocardium directly affected by ischemia [Bujak M, Frangogiannis N G. The role of TGF-beta signaling in myocardial infarction and cardiac remodeling. Cardiovascular research. 2007; 74:184-95]. Consequences of this cardiac remodeling driven by TGF-β and fibrosis have been associated with myocardial stiffness and systolic and diastolic cardiac dysfunction, resulting in reduced cardiac output, heart failure, and arrhythmias [van den Borne S W, Diez J, Blankesteijn W M, Verjans J, Hofstra L, Narula J. Myocardial remodeling after infarction: the role of myofibroblasts. Nat Rev Cardiol. 2010; 7:30-7]. In this study, AMI mice were used to investigate how MMI-0100 affected myocardial remodeling after acute MI.

Figure 2A:
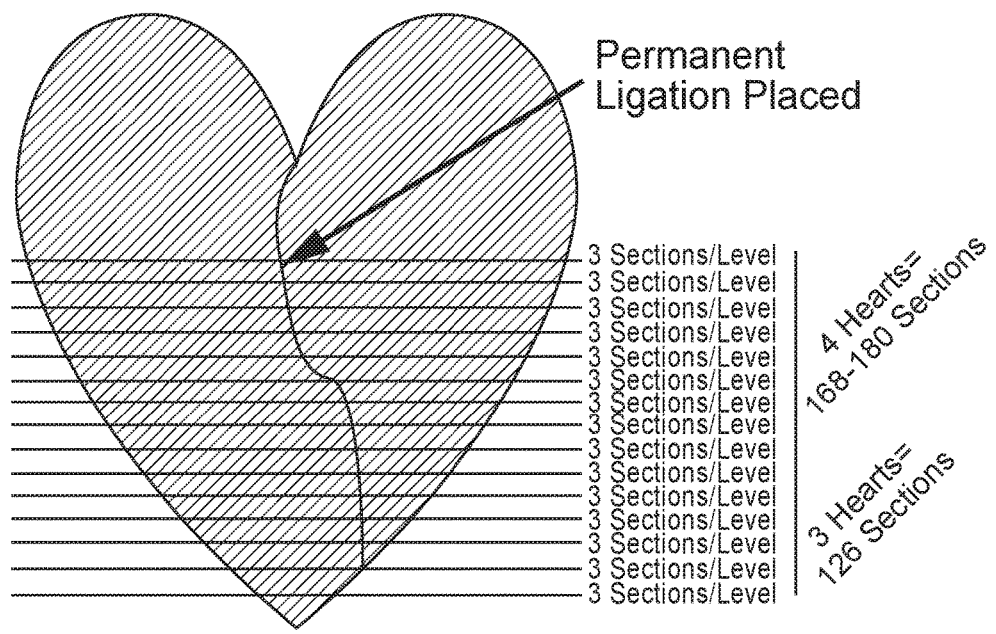

Acute myocardial infarction (AMI) was induced in eight to ten week old C57BL/6 mice by permanent ligation of the left anterior descending (LAD) coronary artery and treated as described in Example 1. Hearts were obtained from AMI mice and histologically analyzed for fibrosis in Masson's trichrome stained sections in a systemic manner (FIG. 2A). Based on 4 hearts, analyzed blinded to treatment and objectively using computer algorithms recognizing fibrosis based on hue, AMI mice which received MMI-0100 peptide exhibited 50% less fibrosis than did untreated mice (FIG. 2B). That is, based on weighted averages of 168-180 cross sectional areas taken from the point of ligation all the way through the apex, MMI-0100 reduced fibrosis to ~11% (FIG. 2B). Since Masson's trichrome is a stain designed to detect collagen, which is present to a small extent in normal healthy hearts, analysis was performed on three control groups: (1) thoracotomy and sham ligation; (2) no surgery and no drug; and (3) a group given MMI-0100 daily that did not undergo surgery. The extensive analysis of these hearts, paralleling the methods used in the experimental groups, showed that collagen was present in less than 1% of the heart area (normal extracellular matrix and basement membranes) (FIG. 2B). Taken together, these findings demonstrated that MMI-0100 peptide significantly reduced the fibrosis response by 50% during the remodeling process, even when given 30 minutes after the ischemic insult.

Based on the initial histology results in which a decrease in fibrosis was observed, a more detailed histological analysis was performed on hearts obtained from AMI mice. Representative histological sections from multiple individual hearts illustrated two general types of fibrosis sparing. First, fibrosis that occurs distant to the site of ischemia in AMI, illustrated in FIG. 2C with arrows, is not found to the same extent in the heart sections treated with MMI-0100 (FIG. 2D), although it is still present (See single arrow). Second, fibrosis at the site of infarction after AMI was generally complete (all fibrotic), whereas when MMI-0100 peptide was given, islands of viable myocytes (See asterisk, FIG. 2D, top panel) could be identified. When investigated at a higher magnification, the islands of myocyte sparing within the ischemic region scar were found routinely in hearts where MMI-0100 was given (FIG. 10D-F). In contrast, complete fibrosis was seen after AMI in all animals uniformly in multiple representative sections (FIG. 10A-C). The extent of the sparing varied, being more localized to the endocardium at times (FIG. 10D, 10F, arrows), while being more transmural in others (FIG. 10E, see asterisk corresponding to asterisk in FIG. 2D, top panel). Without being bound by theory, these findings suggest that the significant reduction in fibrosis by MMI-0100 results in critical muscle sparing at the site of ischemic insult, while at the same time reducing the distant non-ischemic site of fibrosis that contributes to the detrimental effects on cardiac function, which is consistent with the functional findings in the same hearts (FIGS. 1A-D).

Example 3: MMI-0100 Peptide Post-Hypoxia Inhibits Cardiomyocyte Apoptosis In Vitro by Inhibiting MK2 Activity In this study, the underlying mechanisms by which MMI-0100 peptide spares cardiomyocyte death within the ischemic region and reduces non-infarcted myocardial fibrosis were investigated by measuring activation of caspase 3/7 and LDH release; as well as heterogeneous nuclear ribonucleoprotein A0 (HNRNPA0), total MK2, and phosphorylated-MK2 (p-MK2) protein expression.

Cell lines derived from ventricular (H9C2) and atrial (HL1) cardiomyocytes were used to determine cell death in the presence of MMI-0100 peptide at doses previously shown to suppress MK2 activity (20 and 100 µm) [Muto A, Panitch A, Kim N, Park K, Komalavilas P, Brophy C M, et al Inhibition of Mitogen Activated Protein Kinase Activated Protein Kinase II with MMI-0100 reduces intimal hyperplasia ex vivo and in vivo. Vascular pharmacology. 2012;

56:47-55; Ward B C, Kavalukas S, Brugnano J, Barbul A, Panitch A. Peptide inhibitors of MK2 show promise for inhibition of abdominal adhesions. The Journal of surgical research. 2011; 169:e27-36]. Both HL1 and H9C2 cell lines have been established in models of acute myocardial infarction by culturing in anoxic (1% oxygen) conditions that induce cell death [Sun J, Sun G, Meng X, Wang H, Wang M, Qin M, et al. Ginsenoside RK3 Prevents Hypoxia-Reoxygenation Induced Apoptosis in H9c2 Cardiomyocytes via AKT and MAPK Pathway. Evidence-based complementary and alternative medicine: eCAM. 2013; 2013:690190; Zhang C, Lin G, Wan W, Li X, Zeng B, Yang B, et al. Resveratrol, a polyphenol phytoalexin, protects cardiomyocytes against anoxia/reoxygenation injury via the TLR4/NF-kappaB signaling pathway. International journal of molecular medicine. 2012; 29:557-63; Bukowska A, Hammwohner M, Sixdorf A, Schild L, Wiswedel I, Rohl F W, et al. Dronedarone prevents microcirculatory abnormalities in the left ventricle during atrial tachypacing in pigs. British journal of pharmacology. 2012; 166:964-80; Liu S X, Zhang Y, Wang Y F, Li X C, Xiang M X, Bian C, et al. Upregulation of heme oxygenase-1 expression by hydroxysafflor yellow A conferring protection from anoxia/reoxygenation-induced apoptosis in H9C2 cardiomyocytes. International journal of cardiology. 2012; 160:95-101; Severino A, Campioni M, Straino S, Salloum F N, Schmidt N, Herbrand U, et al. Identification of protein disulfide isomerase as a cardiomyocyte survival factor in ischemic cardiomyopathy. Journal of the American College of Cardiology. 2007; 50:1029-37]. Activation of caspase 3/7 and LDH release were measured as markers of cell death in the presence of MMI-0100.

Figure 3B:
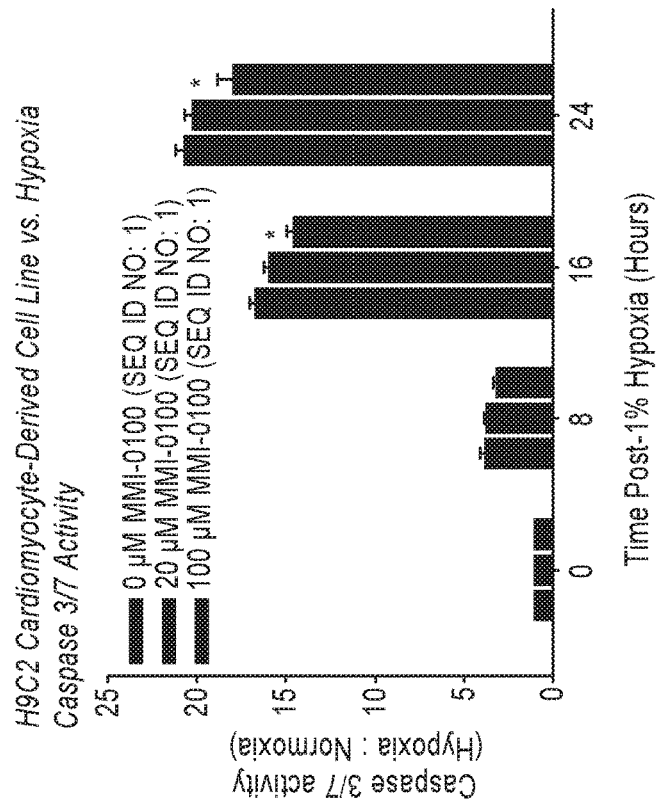
Figure 3A:
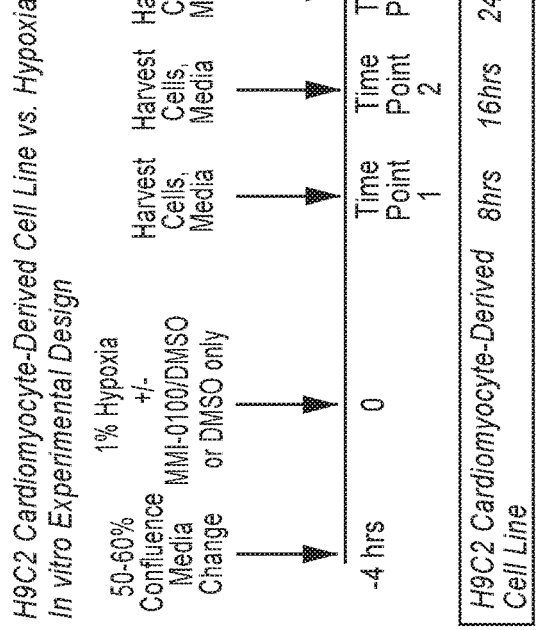
Figure 11A:
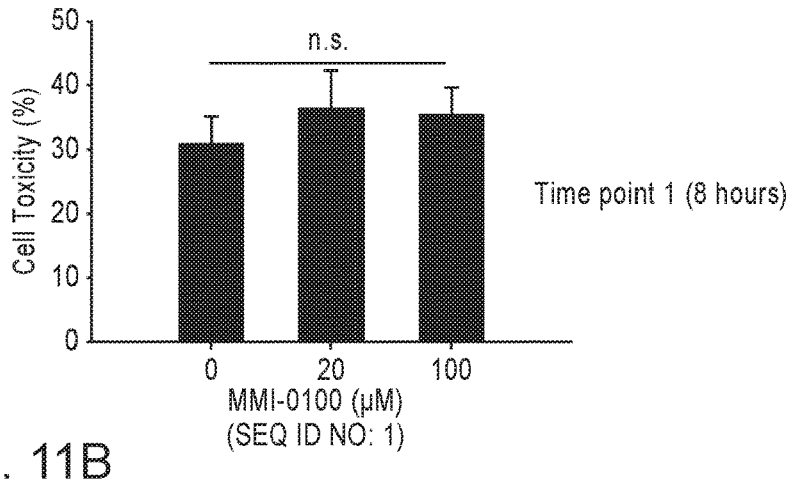
FIGS. 11A-C show that cardiomyocyte cell lines and primary cardiac fibroblasts treated with 20 or 100 mM MMI-0100 peptide have an enhanced LDH release during hypoxia challenge, compared to their response during normoxia (FIG. 3C, FIG. 5C, FIG. 7C). H9C2 cells (FIG. 11A.); HL1 cells (FIG. 11B.); and primary cardiac fibroblasts (C.) do not exhibit an enhanced LDH release at the primary time point tested with hypoxia (8, 4, and 16 hours, respectively). Significant increases in LDH are detected (compare to FIG. 3C, FIG. 5C, and FIG. 7C, respectively). A Kruskal-Wallis One-way ANOVA was performed at each terminal time point in experiments run in parallel. If significance was reached (p<0.05), a post-hoc all pairwise Multiple Comparison Procedures (Tukey Test) was performed between each of the groups to determine significance. *p<0.05 vs. 0 µM group (DMSO vehicle control).

When the ventricular H9C2 myocyte-derived cells were challenged with 1% hypoxia (FIG. 3A), caspase 3/7 activity increased <5 fold at 8 hours compared to cells harvested at the start of hypoxia challenge. At 16 and 24 hours, caspase 3/7 increased 15-20 fold (FIG. 3B), paralleling increased LDH release of 60-80% in the same cells (FIG. 3C). The 100 µM MMI-0100 inhibited caspase 3/7 activity at 16 and 24 hours. Without being bound by theory, this data suggests that MMI-0100 inhibited apoptotic pathways at this time point (FIG. 3B). Both 20 and 100 µM MMI-0100 significantly enhanced LDH release at 8 hours in cell challenged with 1% hypoxia, while only the 100 µM MMI-0100 concentration induced enhanced LDH release at 16 hours (FIG. 3B). Subsequent studies to determine the effect of MMI-0100 on LDH release in H9C2 cells in normoxic conditions demonstrated that MMI-0100 did not enhance LDH release in the absence of hypoxia at 8 hours (FIG. 11A). This data confirmed that MMI-0100 does not enhance LDH release directly, while parallel studies investigating MMI-0100 effects on the LDH assay itself found that MMI-0100 had no effect on the colorimetric assay itself (data not shown).

The effects of MMI-0100 peptide on heterogeneous nuclear ribonucleoprotein A0 (HNRNPA0), total MK2, and p-MK2 expression in H9C2 cells at all time-points tested in the caspase 3/7 activity and LDH release studies (FIGS. 4A-B) also were investigated. MMI-0100 at a concentration of 100 µM significantly inhibited HNRNPA0 expression after being induced by hypoxia (FIG. 4A). Total MK2 and p-MK2 protein levels were not changed by MMI-0100 peptide at either 20 or 100 µM concentrations (FIG. 4B).

Figure 11B:
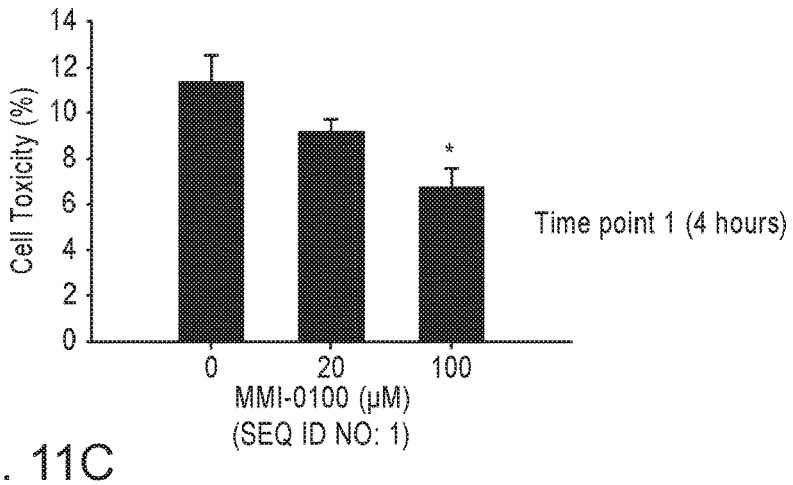
Figure 11C:
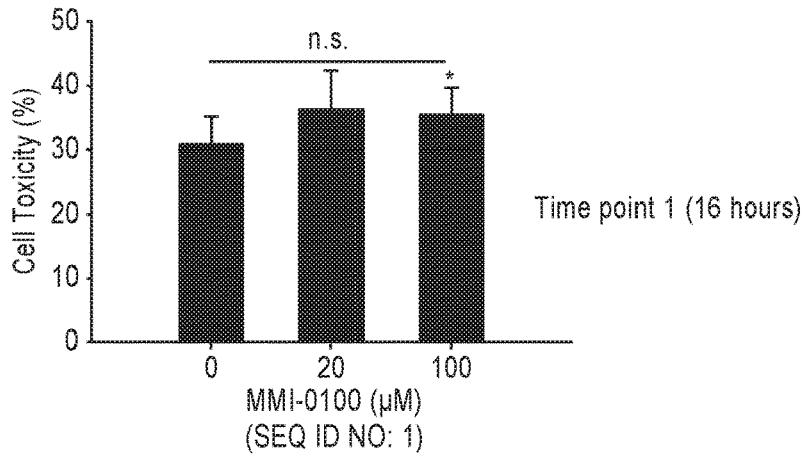
Figure 12:
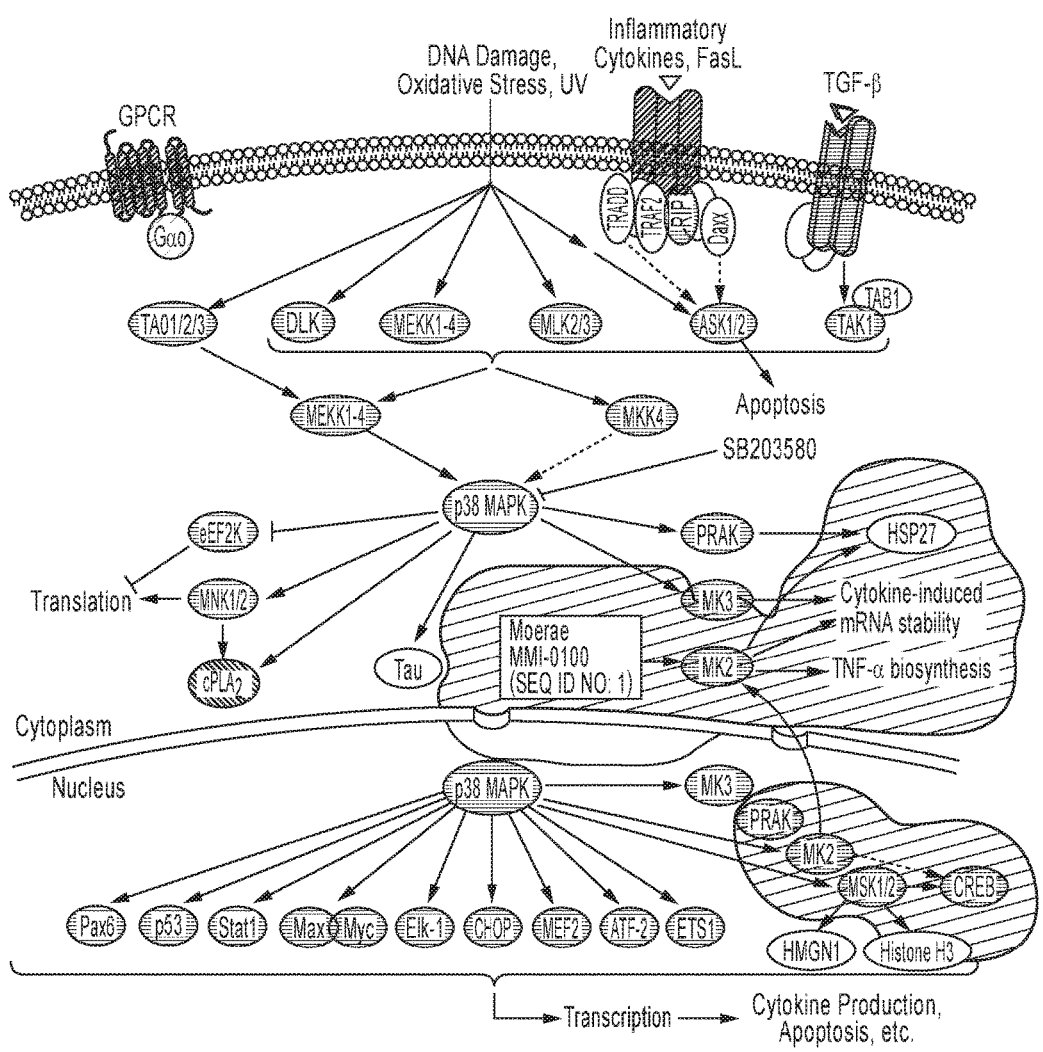
FIG. 12 shows a schematic of the p38 MAPK signaling pathway (taken from moeraematrix.com).
Figure 13:
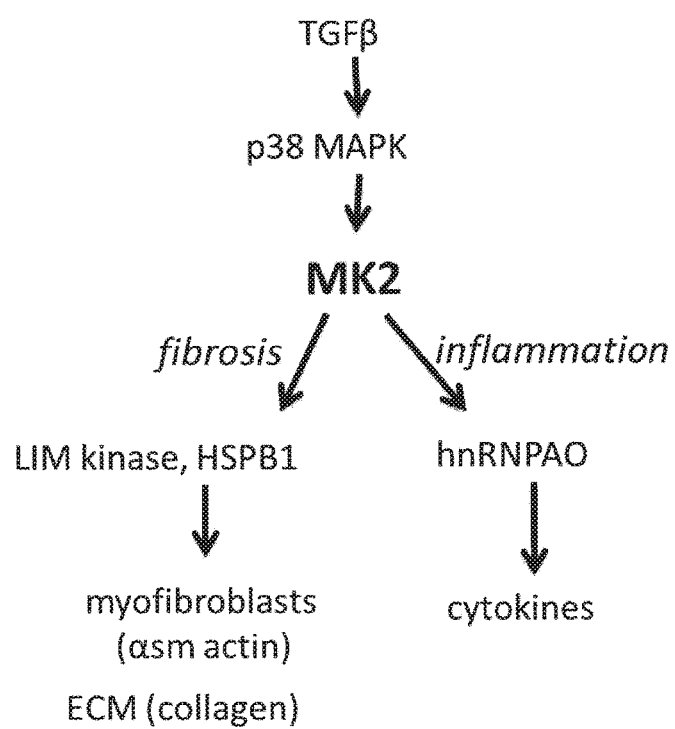
FIG. 13 shows a schematic of the Mapkap kinase 2 (MK2) pathway.

When the atrial HL1 myocyte-derived cells were challenged with 1% hypoxia (FIG. 5A), caspase 3/7 activity increased 6 fold by 4 hours compared to cells harvested at the start of hypoxia challenge (FIG. 5B). At 8 and 12 hours, caspase 3/7 increased approximately 10 fold (FIG. 5B); paralleling increases in LDH release of 20-60% in the same cells (FIG. 5C). MMI-0100 at a concentration of 100 µM inhibited caspase 3/7 activity at 12 hours. Without being bound by theory, this data suggests that MMI-0100 inhibited apoptotic pathways at this time point (FIG. 5B). Both 20 and 100 µM MMI-0100 significantly enhanced LDH release at 4 hours in cells challenged with 1% hypoxia, while only the 100 µM MMI-0100 had enhanced LDH release at 8 hours (FIG. 5C). Subsequent studies to determine the effect of MMI-0100 on LDH release of HL1 cells in normoxic conditions demonstrated that MMI-0100 did not enhance LDH release in the absence of hypoxia at 4 hours. MMI-0100 at a concentration of 100 µM unexpectedly inhibited LDH release in HL1 cells (FIG. 11B).

Figure 6A:
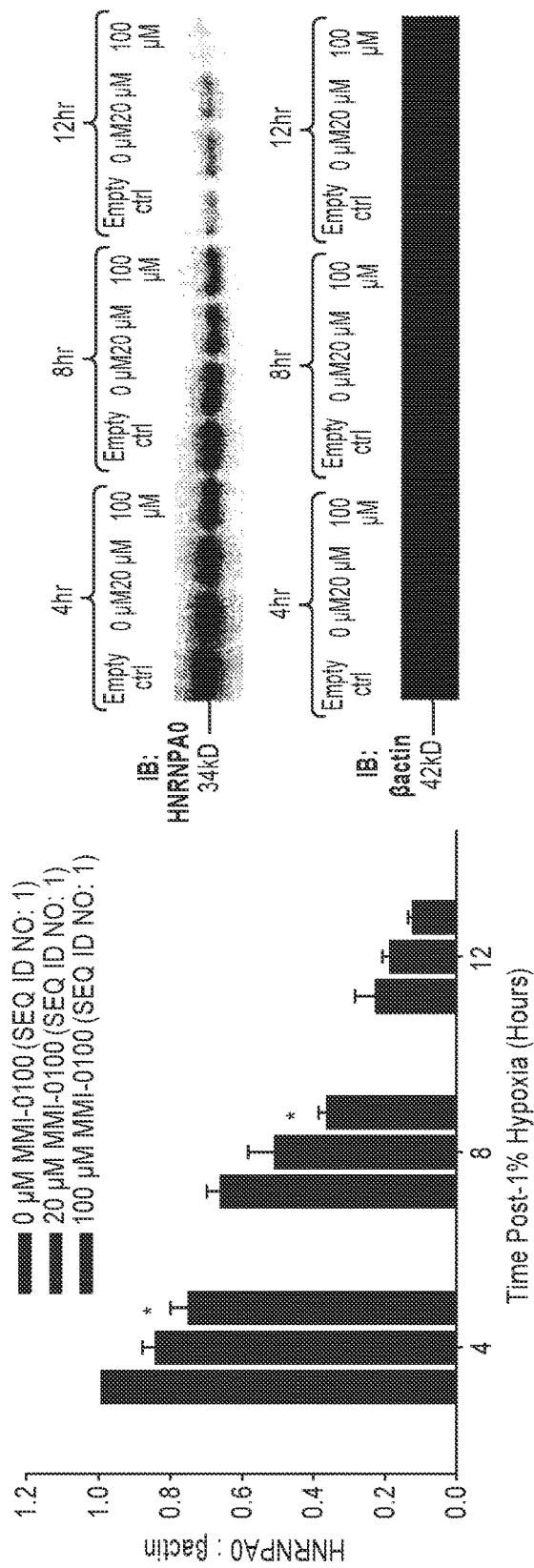
FIGS. 6A-B show that MMI-0100 peptide reduces MK2 activity in HL1 cardiomyocytes challenged with 1% hypoxia as measured by downstream HNRNPA0 protein expressed, but does not reduce phospho- or total MK2 levels.
Figure 6B:
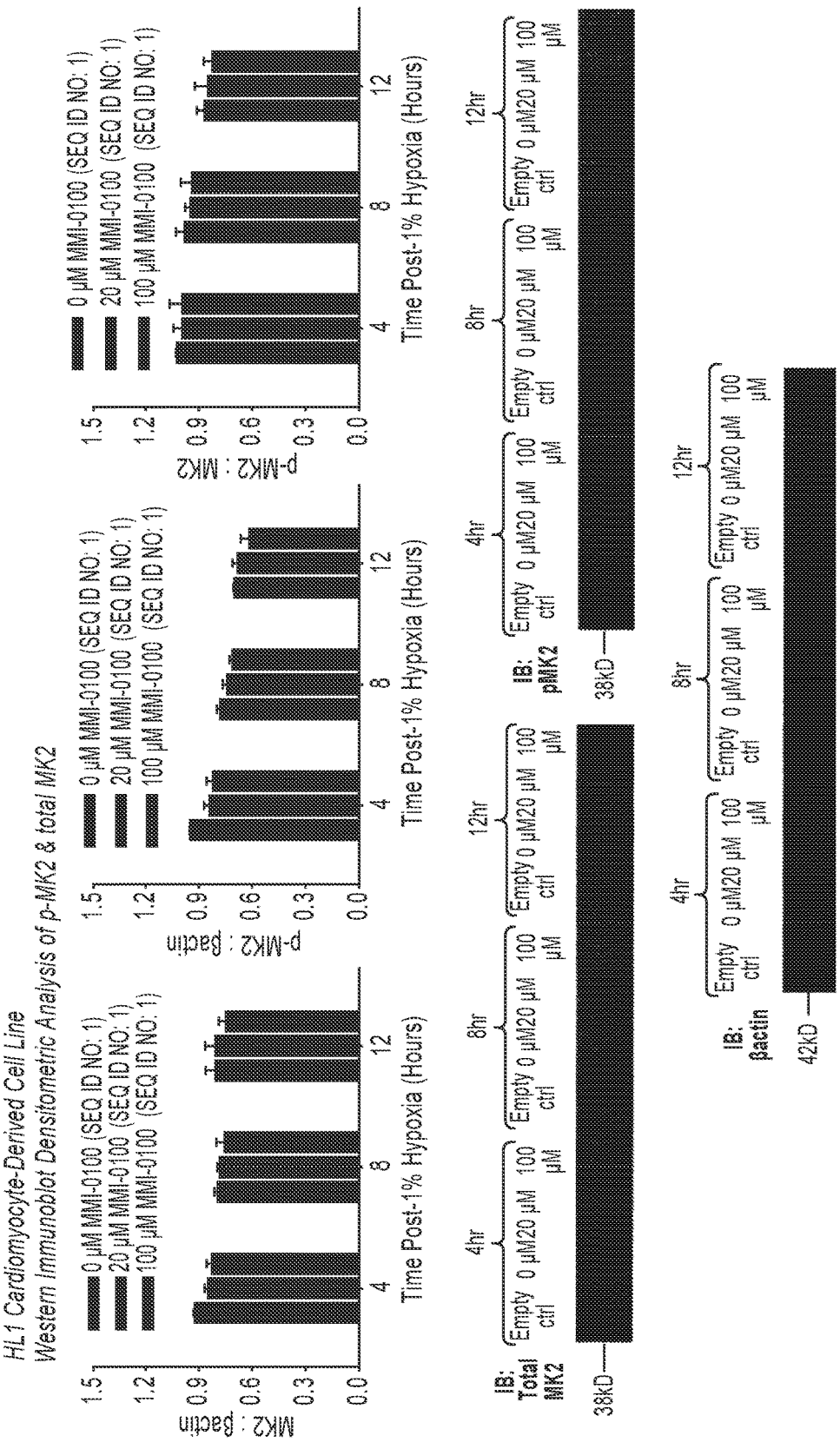

The effects of MMI-0100 on heterogeneous nuclear ribonucleoprotein A0 (HNRNPA0), total MK2, and p-MK2 expression in HL1 cells at all time-points tested in the caspase 3/7 activity and LDH release studies (FIGS. 5A-C) also were investigated. MMI-0100 at a concentration of 100 µM inhibited HNRNPA0 protein expression at 4 and 8 hours after being induced by hypoxia (FIG. 6A). Total MK2 and p-MK2 protein levels were not changed by MMI-0100 peptide at either 20 or 100 µM MMI-0100 concentrations (FIG. 6B). This data confirmed that MMI-0100 does not directly enhance LDH release.

Example 4: MMI-0100 Treatment Post-Hypoxia Enhances Primary Cardiac Fibroblast Cell Death In Vitro Despite Inhibiting MK2 Activity Fibroblasts are integral to the repair of the heart, contributing to the remodeling process after ischemia, fibrosis, and the progression of heart failure [Porter K E, Turner N A. Cardiac fibroblasts: at the heart of myocardial remodeling. Pharmacol Ther. 2009; 123:255-78]. By physical and biochemical interaction with cardiomyocytes and the extracellular matrix, fibroblasts are position to sense and respond to injury.

In this study, primary cardiac fibroblasts were isolated as previously described in models of acute MI in culture [Rupp H, Maisch B. Control of apoptosis of cardiovascular fibroblasts: a novel drug target. Herz. 1999; 24:225-31; Sangeetha M, Pillai M S, Philip L, Lakatta E G, Shivakumar K. NF-kappa B inhibition compromises cardiac fibroblast viability under hypoxia. Experimental cell research. 2011; 317:899-909; Chu W, Li X, Li C, Wan L, Shi H, Song X, et al. TGFBR3, a potential negative regulator of TGF-beta signaling, protects cardiac fibroblasts from hypoxia-induced apoptosis. Journal of cellular physiology. 2011; 226:2586-94; Leicht M, Briest W, Holzl A, Zimmer H G. Serum depletion induces cell loss of rat cardiac fibroblasts and increased expression of extracellular matrix proteins in surviving cells. Cardiovascular research. 2001; 52:429-37] and challenged with 1% hypoxia in the presence or absence of MMI-0100 peptide to determine the peptide's effects on cardiac fibroblast cell death. These studies were designed to parallel the cardiomyocyte studies (Example 3), with the exception that longer time points were used due to the relative resistance (compared to cardiomyocytes) of cardiac fibroblasts to apoptosis and LDH release.

Figure 8A:
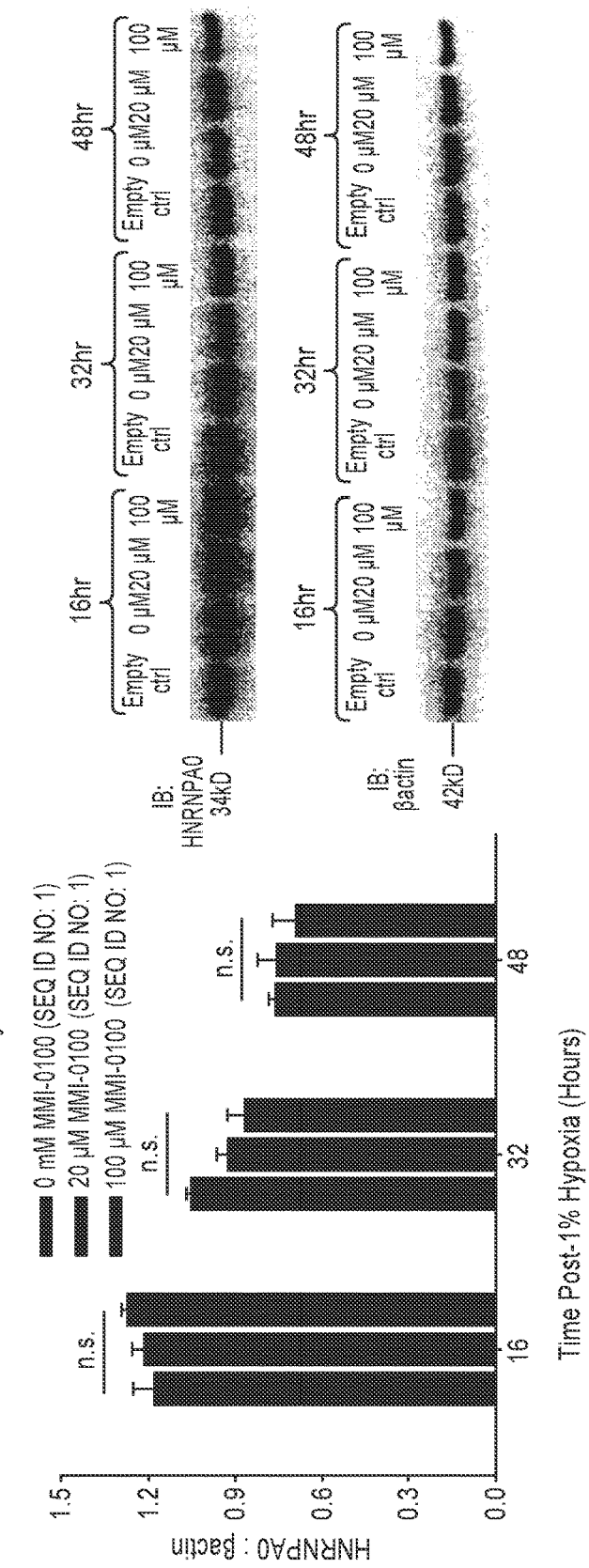
FIGS. 8A-B show that MMI-0100 peptide reduction of MK2 activity is not detected at the time points cell death is affected in primary cardiac fibroblasts challenged with 1% hypoxia, as measured by downstream HNRNPA0, phospho-MK2, and total MK2 protein levels.
Figure 8B:
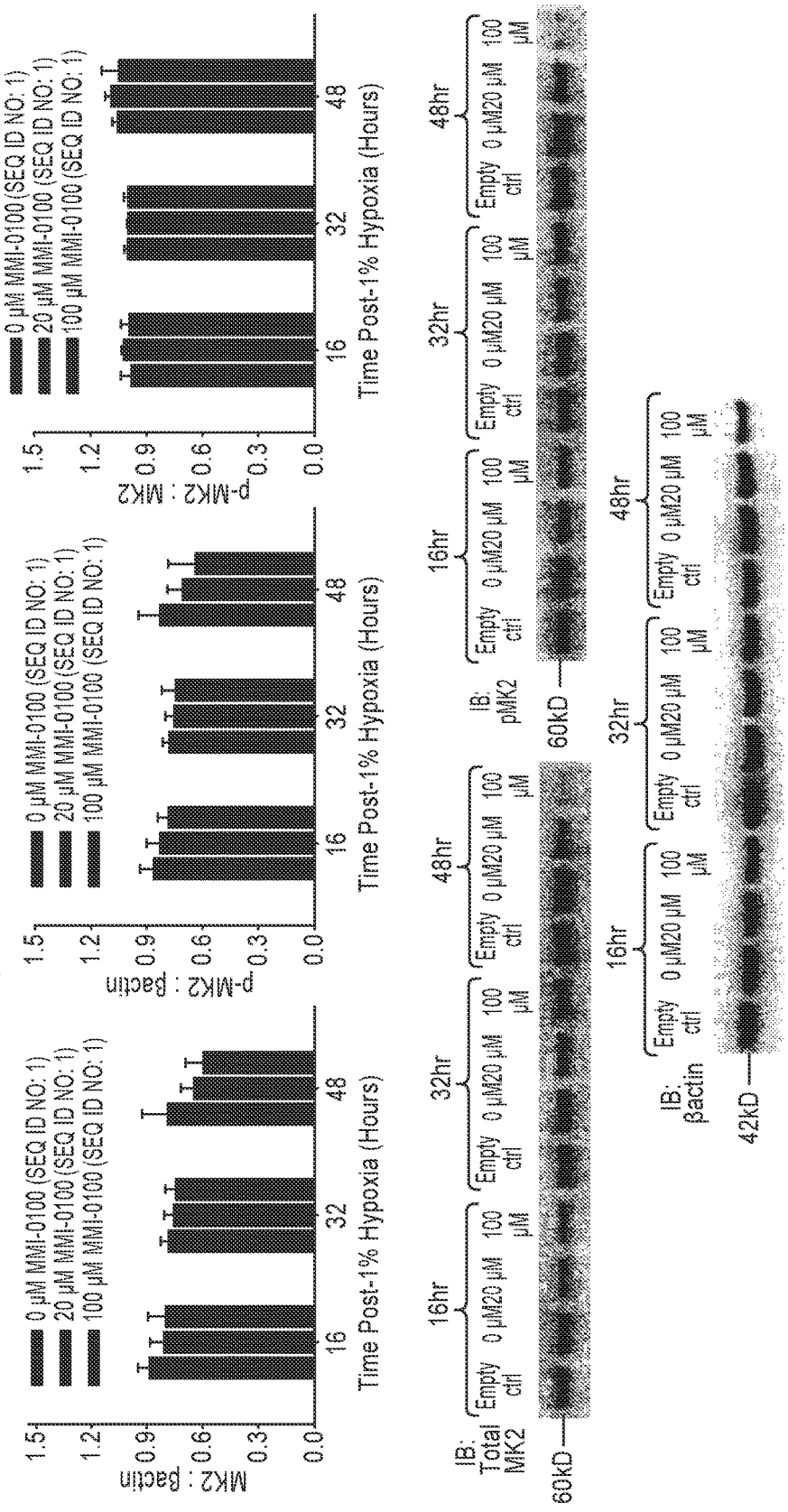

The results of this study are shown in FIGS. 7A-C. In contrast to the cardiomyocyte-derived cell lines tested above, 100 µM MMI-0100 peptide treatment significantly enhanced caspase 3/7 activity at 16 and 32 hours of hypoxia (FIG. 7B). LDH release was significantly enhanced in cultured primary cardiac fibroblasts at 16, 32, and 48 hours of hypoxia (FIG. 7C). Subsequent studies to determine the effect of MMI-0100 on LDH release of primary cardiac fibroblasts in normoxic conditions demonstrated that MMI-0100 did not enhance LDH release in the absence of hypoxia at 4 hours (FIG. 11B). MMI-0100 peptide did not change MK2 activity, as measured by HNRNPA0 protein levels at 16, 32, or 48 hours (FIG. 8A). Similarly, protein levels of MK2 and p-MK2 did not significantly differ in the presence of MMI-0100 compared to hypoxia alone (FIG. 8B). These data indicate that the MMI-0100 peptide enhances cell death of cardiac fibroblasts in the presence of hypoxia. Without being bound by theory, decreased fibroblast viability may be one mechanism by which a reduction of fibrosis occurs, leading to the decreased fibrosis seen in vivo (FIGS. 2A-E). This decrease in fibroblasts (and presumably fibrosis), in addition to the inhibited cardiac cell death afforded cardiomyocytes when treated with MMI-0100 (FIGS. 3A-C, FIGS. 4A-B, FIGS. 5A-C, FIGS. 6A-B), may offer two mechanisms by which MMI-0100 can improve cardiac function and attenuate cardiac dilation after AMI (FIGS. 1A-D).

Example 5: Cytokine Analysis of Culture Media for TNFα, IL-1β, and IL-6

The inflammatory activation of p38 MAPK in cardiac fibroblasts stimulates the release of IL-1α, TNFα, and MMP-3 [Tondera C, Laube M, Wimmer C, Kniess T, Mosch B, Grossmann K, et al. Visualization of cyclooxygenase-2 using a 2,3-diarylsubstituted indole-based inhibitor and confocal laser induced cryofluorescence microscopy at 20K in melanoma cells in vitro. Biochemical and biophysical research communications. 2013; 430:301-6]. These cytokines can stimulate cardiomyocyte contractility depression and cardiomyocyte secretion of IL-1, IL-6, and TNFα. Since IL-1, IL-6, and TNFα all directly depress cardiac function and mediate heart failure [El-Menyar A A. Cytokines and myocardial dysfunction: state of the art. J Card Fail. 2008; 14:61-74], these non-cell death induced effects are critical to the dysfunction found in acute MI.

In this study, cytokine analysis of TNFα, IL-1β, and IL-6 was performed for either mouse (HL1) or rat (H9C2 and primary cardiac fibroblast) culture media using Luminex multiplex assays (LUM000, LUM401, LUM406, LUM410, LUR000, LUR401, LUR406, LUR410, R&D Systems, Inc., Minneapolis, Minn.) analyzed on a Bio-Plex 200 (Bio-Rad, Hercules, Calif.) according to manufacturer's protocol.

Briefly, HL1, H9C2 or primary cardiac fibroblast cell culture media was mixed with cytokine capture antibodies coupled to specific bead sets in 96-well filter-bottomed microplates and incubated. After cytokines were bound to their corresponding capture antibody/bead, a Phycoerythrin (PE)-conjugated cytokine-specific detection antibody was used as a reporter. The amounts of cytokines bound are proportional to the PE signals generated for each bead set. Fluorescence levels generated by the beads and the PE-labeled antibody were analyzed on a Bio-Plex 200 using dual laser system as the beads pass through a flow cell. Real time quantitative data was generated for each signal. Standard curves were run in parallel with each experiment.

TNFα, IL-1β, and IL-6 were undetectable in the culture media of all cell types at all times tested (data not shown). Without being bound by theory, either these cytokines were released and utilized much earlier than assayed, or this may be a limitation of using single cell suspensions that do not replicate the cross talk between cells (e.g. cardiomyocytes and fibroblasts) that occurs in vivo and plays an important role in cardiac function.

Example 6: Interaction of MMI-0100 with Other Pharmacologically Relevant Enzymes, Receptors and Channels MMI-0100 was tested for its potential to inhibit 40 non-kinase enzyme assays, including phosphatases and proteases. Enzyme assays were performed in the presence and absence of 100 µM MMI-0100. Interaction at a target was considered significant if a greater than 50% inhibition of activity was measured in the presence of MMI-0100. No significant interaction of MMI-0100 was measured at any of the other pharmacological targets in the panel (data not shown).

In order to determine whether MMI-0100 interaction with pharmacologically relevant receptors would result in pharmacological activity, MMI-0100 was tested for its effects in relevant cell-based assays. Results of the cell-based assays confirmed that MMI-0100 has no substantial effect on pharmacologically relevant receptors in cellular functional assays (data not shown).

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method for treating ischemia-mediated apoptosis in a peri-infarct border zone in a subject that has suffered a myocardial infarction (MI), the method comprising administering to the subject in need of such treatment a therapeutic amount of a pharmaceutical composition comprising a polypeptide of amino acid sequence YARAAARQARAKALARQLGVAA (SEQ ID NO: 1) or a functional equivalent thereof selected from the group consisting of a polypeptide of amino acid sequence FAKLAARLYRKALARQLGVAA (SEQ ID NO: 4), KAFAKLAARLYRKALARQLGVAA (SEQ ID NO: 5), YARAAARQARAKALARQLAVA (SEQ ID NO: 6), YARAAARQARAKALARQLGVA (SEQ ID NO: 7) and HRRIKAWLKKIKALARQLGVAA (SEQ ID NO: 8); and a pharmaceutically acceptable carrier,
wherein
the MI is characterized by aberrant deposition of an extracellular matrix protein, an aberrant promotion of fibroblast proliferation in the heart, an aberrant induction of myofibroblast differentiation, an aberrant promotion of attachment of myofibroblasts to an extracellular matrix or a combination thereof;
wherein when tested in vitro under hypoxic conditions, the pharmaceutical composition is effective to inhibit apoptotic cell death of ventricular cardiomyocyte cells when measured at 16 and 24 hours and atrial cardiomyocyte cells when measured at 12 hours, compared to control cells harvested at initiation of hypoxia challenge;
and
the therapeutic amount of the pharmaceutical composition is effective to inhibit apoptotic cell death of cardiomyocytes in the peri-infarct zone, wherein without the therapeutic effect, ventricular remodeling can progress to heart failure.

2. The method according to claim 1, wherein the therapeutic amount is effective to enhance cell death of cardiac fibroblasts.

3. The method according to claim 1, wherein the therapeutic amount is effective to inhibit caspase activity.

4. The method according to claim 3, wherein the caspase activity is caspase 3/7 activity.

5. The method according to claim 1, wherein the therapeutic amount is effective to enhance lactate dehydrogenase (LDH) release.

6. The method according to claim 1, wherein the therapeutic amount is effective to inhibit heterogeneous nuclear ribonucleoprotein A0 (HNRNPA0) protein expression.

7. A method for improving cardiac function by treating ischemia-mediated apoptosis in a peri-infarct border zone after a myocardial infarction (MI) in a subject in need thereof, the method comprising administering to the subject in need thereof a therapeutic amount of a pharmaceutical composition comprising a polypeptide of amino acid sequence YARAAARQARAKALARQLGVAA (SEQ ID NO: 1) or a functional equivalent thereof selected from the group consisting of a polypeptide of amino acid sequence FAKLAARLYRKALARQLGVAA (SEQ ID NO: 4), KAFAKLAARLYRKALARQLGVAA (SEQ ID NO: 5), YARAAARQARAKALARQLAVA (SEQ ID NO: 6), YARAAARQARAKALARQLGVA (SEQ ID NO: 7) and HRRIKAWLKKIKALARQLGVAA (SEQ ID NO: 8); and a pharmaceutically acceptable carrier,
wherein
the therapeutic amount of the pharmaceutical composition is effective to inhibit apoptotic cell death of cardiomyocytes in the peri-infarct zone,
wherein when tested in vitro under hypoxic conditions, the pharmaceutical composition is effective to inhibit apoptotic cell death of ventricular cardiomyocyte cells when measured at 16 and 24 hours and atrial cardiomyocyte cells when measured at 12 hours, compared to control cells harvested at initiation of hypoxia challenge; and wherein without the therapeutic effect, ventricular remodeling can progress to heart failure.

8. The method according to claim 7, wherein the therapeutic amount is effective to enhance cell death of cardiac fibroblasts.

9. The method according to claim 7, wherein the therapeutic amount is effective to inhibit caspase activity.

10. The method according to claim 9, wherein the caspase activity is caspase 3/7 activity.

11. The method according to claim 7, wherein the therapeutic amount is effective to enhance lactate dehydrogenase (LDH) release.

12. The method according to claim 7, wherein the therapeutic amount is effective to inhibit heterogeneous nuclear ribonucleoprotein A0 (HNRNPA0) expression.

13. The method according to claim 1, wherein the therapeutic amount of the pharmaceutical composition is effective (i) to inhibit Mitogen Activated Protein Kinase Activated Protein Kinase II (MK2); and
(ii) to reduce cardiac fibrosis at a site of ischemic insult; or
(iii) to preserve cardiac muscle; or
(iv) to preserve systolic function; or
(v) to protect cardiomyocytes from an ischemic insult; or
(vi) a combination thereof.

14. The method according to claim 7, wherein the therapeutic amount of the pharmaceutical composition is effective (i) to inhibit Mitogen Activated Protein Kinase Activated Protein Kinase II (MK2); and
(ii) to reduce cardiac fibrosis at a site of ischemic insult; or
(iii) to preserve cardiac muscle; or
(iv) to preserve systolic function; or
(v) to protect cardiomyocytes from an ischemic insult; or
(vi) a combination thereof.

* * * * *

SEQUENCE LISTING

<160> NUMBER OF SEQ ID NOS: 27

<210> SEQ ID NO 1
<211> LENGTH: 22
<212> TYPE: PRT
<213> ORGANISM: Unknown
<220> FEATURE:
<223> OTHER INFORMATION: Mammal

<400> SEQUENCE: 1

Tyr Ala Arg Ala Ala Ala Arg Gln Ala Arg Ala Lys Ala Leu Ala Arg
1               5                   10                  15

Gln Leu Gly Val Ala Ala
            20

```
<210> SEQ ID NO 2
<211> LENGTH: 11
<212> TYPE: PRT
<213> ORGANISM: Unknown
<220> FEATURE:
<223> OTHER INFORMATION: Mammal

<400> SEQUENCE: 2

Tyr Ala Arg Ala Ala Ala Arg Gln Ala Arg Ala
1               5                   10

<210> SEQ ID NO 3
<211> LENGTH: 11
<212> TYPE: PRT
<213> ORGANISM: Unknown
<220> FEATURE:
<223> OTHER INFORMATION: Mammal

<400> SEQUENCE: 3

Lys Ala Leu Ala Arg Gln Leu Gly Val Ala Ala
1               5                   10

<210> SEQ ID NO 4
<211> LENGTH: 21
<212> TYPE: PRT
<213> ORGANISM: Unknown
<220> FEATURE:
<223> OTHER INFORMATION: Mammal

<400> SEQUENCE: 4

Phe Ala Lys Leu Ala Ala Arg Leu Tyr Arg Lys Ala Leu Ala Arg Gln
1               5                   10                  15

Leu Gly Val Ala Ala
            20

<210> SEQ ID NO 5
<211> LENGTH: 23
<212> TYPE: PRT
<213> ORGANISM: Unknown
<220> FEATURE:
<223> OTHER INFORMATION: Mammal

<400> SEQUENCE: 5

Lys Ala Phe Ala Lys Leu Ala Ala Arg Leu Tyr Arg Lys Ala Leu Ala
1               5                   10                  15

Arg Gln Leu Gly Val Ala Ala
            20

<210> SEQ ID NO 6
<211> LENGTH: 21
<212> TYPE: PRT
<213> ORGANISM: Unknown
<220> FEATURE:
<223> OTHER INFORMATION: Mammal

<400> SEQUENCE: 6

Tyr Ala Arg Ala Ala Ala Arg Gln Ala Arg Ala Lys Ala Leu Ala Arg
1               5                   10                  15

Gln Leu Ala Val Ala
            20

<210> SEQ ID NO 7
<211> LENGTH: 21
<212> TYPE: PRT
<213> ORGANISM: Unknown
<220> FEATURE:
```

```
<223> OTHER INFORMATION: Mammal

<400> SEQUENCE: 7

Tyr Ala Arg Ala Ala Ala Arg Gln Ala Arg Ala Lys Ala Leu Ala Arg
1               5                   10                  15

Gln Leu Gly Val Ala
            20

<210> SEQ ID NO 8
<211> LENGTH: 22
<212> TYPE: PRT
<213> ORGANISM: Unknown
<220> FEATURE:
<223> OTHER INFORMATION: Mammal

<400> SEQUENCE: 8

His Arg Arg Ile Lys Ala Trp Leu Lys Lys Ile Lys Ala Leu Ala Arg
1               5                   10                  15

Gln Leu Gly Val Ala Ala
            20

<210> SEQ ID NO 9
<211> LENGTH: 10
<212> TYPE: PRT
<213> ORGANISM: Unknown
<220> FEATURE:
<223> OTHER INFORMATION: Mammal

<400> SEQUENCE: 9

Lys Ala Leu Ala Arg Gln Leu Ala Val Ala
1               5                   10

<210> SEQ ID NO 10
<211> LENGTH: 10
<212> TYPE: PRT
<213> ORGANISM: Unknown
<220> FEATURE:
<223> OTHER INFORMATION: Mammal

<400> SEQUENCE: 10

Lys Ala Leu Ala Arg Gln Leu Gly Val Ala
1               5                   10

<210> SEQ ID NO 11
<211> LENGTH: 11
<212> TYPE: PRT
<213> ORGANISM: Unknown
<220> FEATURE:
<223> OTHER INFORMATION: Mammal

<400> SEQUENCE: 11

Lys Ala Leu Ala Arg Gln Leu Gly Val Ala Ala
1               5                   10

<210> SEQ ID NO 12
<211> LENGTH: 11
<212> TYPE: PRT
<213> ORGANISM: Unknown
<220> FEATURE:
<223> OTHER INFORMATION: Mammal

<400> SEQUENCE: 12

Lys Ala Leu Asn Arg Gln Leu Gly Val Ala Ala
1               5                   10
```

```
<210> SEQ ID NO 13
<211> LENGTH: 11
<212> TYPE: PRT
<213> ORGANISM: Unknown
<220> FEATURE:
<223> OTHER INFORMATION: Mammal

<400> SEQUENCE: 13

Lys Ala Ala Asn Arg Gln Leu Gly Val Ala Ala
1               5                   10

<210> SEQ ID NO 14
<211> LENGTH: 11
<212> TYPE: PRT
<213> ORGANISM: Unknown
<220> FEATURE:
<223> OTHER INFORMATION: Mammal

<400> SEQUENCE: 14

Lys Ala Leu Asn Ala Gln Leu Gly Val Ala Ala
1               5                   10

<210> SEQ ID NO 15
<211> LENGTH: 11
<212> TYPE: PRT
<213> ORGANISM: Unknown
<220> FEATURE:
<223> OTHER INFORMATION: Mammal

<400> SEQUENCE: 15

Lys Ala Leu Asn Arg Ala Leu Gly Val Ala Ala
1               5                   10

<210> SEQ ID NO 16
<211> LENGTH: 11
<212> TYPE: PRT
<213> ORGANISM: Unknown
<220> FEATURE:
<223> OTHER INFORMATION: Mammal

<400> SEQUENCE: 16

Lys Ala Leu Asn Arg Gln Ala Gly Val Ala Ala
1               5                   10

<210> SEQ ID NO 17
<211> LENGTH: 10
<212> TYPE: PRT
<213> ORGANISM: Unknown
<220> FEATURE:
<223> OTHER INFORMATION: Mammal

<400> SEQUENCE: 17

Lys Ala Leu Asn Arg Gln Leu Ala Val Ala
1               5                   10

<210> SEQ ID NO 18
<211> LENGTH: 11
<212> TYPE: PRT
<213> ORGANISM: Unknown
<220> FEATURE:
<223> OTHER INFORMATION: Mammal

<400> SEQUENCE: 18

Lys Ala Leu Asn Arg Gln Leu Ala Val Ala Ala
1               5                   10

<210> SEQ ID NO 19
```

```
<211> LENGTH: 11
<212> TYPE: PRT
<213> ORGANISM: Unknown
<220> FEATURE:
<223> OTHER INFORMATION: Mammal

<400> SEQUENCE: 19

Lys Ala Leu Asn Arg Gln Leu Gly Ala Ala Ala
1               5                   10

<210> SEQ ID NO 20
<211> LENGTH: 10
<212> TYPE: PRT
<213> ORGANISM: Unknown
<220> FEATURE:
<223> OTHER INFORMATION: Mammal

<400> SEQUENCE: 20

Lys Ala Leu Asn Arg Gln Leu Gly Val Ala
1               5                   10

<210> SEQ ID NO 21
<211> LENGTH: 14
<212> TYPE: PRT
<213> ORGANISM: Unknown
<220> FEATURE:
<223> OTHER INFORMATION: Mammal

<400> SEQUENCE: 21

Trp Leu Arg Arg Ile Lys Ala Trp Leu Arg Arg Ile Lys Ala
1               5                   10

<210> SEQ ID NO 22
<211> LENGTH: 7
<212> TYPE: PRT
<213> ORGANISM: Unknown
<220> FEATURE:
<223> OTHER INFORMATION: Mammal

<400> SEQUENCE: 22

Trp Leu Arg Arg Ile Lys Ala
1               5

<210> SEQ ID NO 23
<211> LENGTH: 11
<212> TYPE: PRT
<213> ORGANISM: Unknown
<220> FEATURE:
<223> OTHER INFORMATION: Mammal

<400> SEQUENCE: 23

Tyr Gly Arg Lys Lys Arg Arg Gln Arg Arg Arg
1               5                   10

<210> SEQ ID NO 24
<211> LENGTH: 12
<212> TYPE: PRT
<213> ORGANISM: Unknown
<220> FEATURE:
<223> OTHER INFORMATION: Mammal

<400> SEQUENCE: 24

Trp Leu Arg Arg Ile Lys Ala Trp Leu Arg Arg Ile
1               5                   10

<210> SEQ ID NO 25
<211> LENGTH: 10
```

```
<212> TYPE: PRT
<213> ORGANISM: Unknown
<220> FEATURE:
<223> OTHER INFORMATION: Mammal

<400> SEQUENCE: 25

Phe Ala Lys Leu Ala Ala Arg Leu Tyr Arg
1               5                   10

<210> SEQ ID NO 26
<211> LENGTH: 12
<212> TYPE: PRT
<213> ORGANISM: Unknown
<220> FEATURE:
<223> OTHER INFORMATION: Mammal

<400> SEQUENCE: 26

Lys Ala Phe Ala Lys Leu Ala Ala Arg Leu Tyr Arg
1               5                   10

<210> SEQ ID NO 27
<211> LENGTH: 11
<212> TYPE: PRT
<213> ORGANISM: Unknown
<220> FEATURE:
<223> OTHER INFORMATION: Mammal

<400> SEQUENCE: 27

His Arg Arg Ile Lys Ala Trp Leu Lys Lys Ile
1               5                   10
```